(12) United States Patent  (10) Patent No.: US 7,572,914 B2
Gangloff et al.  (45) Date of Patent: Aug. 11, 2009

(54) KINASE INHIBITORS

(75) Inventors: Anthony R. Gangloff, San Diego, CA (US); Jacek Nowakowski, San Diego, CA (US); Bheema R. Paraselli, San Diego, CA (US); Jeffrey A. Stafford, San Diego, CA (US); Michael G. Tennant, San Francisco, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 510 days.

(21) Appl. No.: 11/015,348

(22) Filed: Dec. 17, 2004

(65) Prior Publication Data

US 2005/0153966 A1 Jul. 14, 2005

Related U.S. Application Data

(60) Provisional application No. 60/531,202, filed on Dec. 19, 2003.

(51) Int. Cl.
*A61K 31/47* (2006.01)
*C07D 271/02* (2006.01)

(52) U.S. Cl. .................. 546/157; 546/158; 546/160; 514/312

(58) Field of Classification Search .............. 546/158, 546/167, 157; 514/312
See application file for complete search history.

(56) References Cited

U.S. PATENT DOCUMENTS

| | | | |
|---|---|---|---|
| 4,260,776 A | | 4/1981 | Harnisch |
| 5,491,147 A | | 2/1996 | Boyd et al. |
| 5,739,144 A | | 4/1998 | Warrellow et al. |
| 5,859,034 A | | 1/1999 | Warrellow et al. |
| 5,962,312 A | | 10/1999 | Plowman et al. |
| 5,972,676 A | | 10/1999 | Plowman et al. |
| 6,103,905 A | * | 8/2000 | Cuny et al. ............. 546/167 |
| 6,143,480 A | | 11/2000 | Obayashi et al. |
| 6,172,084 B1 | * | 1/2001 | Cuny et al. ............. 514/312 |
| 6,207,401 B1 | | 3/2001 | Plowman et al. |
| 6,352,858 B1 | | 3/2002 | Cowsert et al. |
| 6,455,559 B1 | | 9/2002 | Pevarello et al. |
| 6,528,509 B1 | | 3/2003 | Hale et al. |
| 6,593,357 B1 | | 7/2003 | Green et al. |
| 6,610,677 B2 | | 8/2003 | Davies et al. |
| 6,613,776 B2 | | 9/2003 | Knegtel et al. |
| 6,638,926 B2 | | 10/2003 | Davies et al. |
| 6,653,300 B2 | | 11/2003 | Bebbington et al. |
| 6,653,301 B2 | | 11/2003 | Bebbington et al. |
| 6,656,939 B2 | | 12/2003 | Bebbington et al. |
| 6,660,731 B2 | | 12/2003 | Bebbington et al. |
| 6,664,247 B2 | | 12/2003 | Bebbington et al. |
| 6,696,452 B2 | | 2/2004 | Davies et al. |
| 6,699,865 B2 | | 3/2004 | Hale et al. |
| 6,706,491 B1 | | 3/2004 | Chang et al. |
| 6,716,575 B2 | | 4/2004 | Plowman et al. |
| 6,727,251 B2 | | 4/2004 | Bebbington et al. |
| 6,743,791 B2 | | 6/2004 | Cao et al. |
| 6,770,643 B2 | | 8/2004 | Cox |
| 6,784,195 B2 | | 8/2004 | Hale et al. |
| 6,806,272 B2 | | 10/2004 | Bauer et al. |
| 6,831,091 B2 | | 12/2004 | Gant et al. |
| 6,841,579 B1 | | 1/2005 | Plowman et al. |
| 6,846,928 B2 | | 1/2005 | Bebbington et al. |
| 6,849,653 B2 | | 2/2005 | Clare et al. |
| 6,858,638 B2 | | 2/2005 | Damour et al. |
| 6,861,422 B2 | | 3/2005 | Hoffmann et al. |
| 6,872,533 B2 | | 3/2005 | Toland |
| 6,890,927 B2 | | 5/2005 | Bogle |
| 6,897,207 B2 | | 5/2005 | Cox |
| 6,916,798 B2 | | 7/2005 | Green et al. |
| 6,919,338 B2 | | 7/2005 | Mortlock et al. |
| 2002/0151573 A1 | | 10/2002 | Gant et al. |
| 2002/0151574 A1 | | 10/2002 | Hale et al. |
| 2003/0004161 A1 | | 1/2003 | Bebbington et al. |
| 2003/0004164 A1 | | 1/2003 | Bebbington et al. |
| 2003/0022885 A1 | | 1/2003 | Bebbington et al. |
| 2003/0036543 A1 | | 2/2003 | Bebbington et al. |
| 2003/0040536 A1 | | 2/2003 | Hale et al. |
| 2003/0055044 A1 | | 3/2003 | Davies et al. |
| 2003/0055068 A1 | | 3/2003 | Bebbington et al. |
| 2003/0064981 A1 | | 4/2003 | Knegtel et al. |

(Continued)

FOREIGN PATENT DOCUMENTS

DE 28 44 606 4/1980

(Continued)

OTHER PUBLICATIONS

Database Registry ACS; Oct. 20, 2000; XP002368779, retrieved from STN, Database accession No. 297763-91-8/RN abstract.

(Continued)

*Primary Examiner*—D. Margaret Seaman
(74) *Attorney, Agent, or Firm*—C. Amy Smith

(57) ABSTRACT

The invention relates to compounds of the following formula that may be used to inhibits kinases, as well as compositions of matter and kits comprising these compounds. The present invention also relates to methods for inhibiting kinases, as well as treatment methods using compounds according to the present invention.

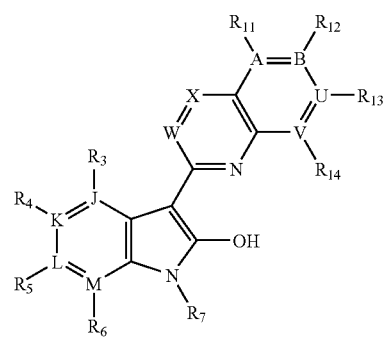

86 Claims, No Drawings

U.S. PATENT DOCUMENTS

| | | |
|---|---|---|
| 2003/0064982 A1 | 4/2003 | Davies et al. |
| 2003/0073687 A1 | 4/2003 | Bebbington et al. |
| 2003/0073692 A1 | 4/2003 | Pulici et al. |
| 2003/0078166 A1 | 4/2003 | Davies et al. |
| 2003/0078275 A1 | 4/2003 | Bebbington et al. |
| 2003/0083327 A1 | 5/2003 | Davies et al. |
| 2003/0092714 A1 | 5/2003 | Cao et al. |
| 2003/0105090 A1 | 6/2003 | Bebbington et al. |
| 2003/0105129 A1 | 6/2003 | Mortlock et al. |
| 2003/0109550 A1 | 6/2003 | Clare et al. |
| 2003/0109697 A1 | 6/2003 | Shepard et al. |
| 2003/0114432 A1 | 6/2003 | Clare et al. |
| 2003/0119856 A1 | 6/2003 | Cochran et al. |
| 2003/0125361 A1 | 7/2003 | Clare et al. |
| 2003/0171357 A1 | 9/2003 | Fancelli et al. |
| 2003/0171359 A1 | 9/2003 | Dahmann et al. |
| 2003/0187002 A1 | 10/2003 | Mortlock et al. |
| 2003/0187007 A1 | 10/2003 | Cao et al. |
| 2003/0208067 A1 | 11/2003 | Cao et al. |
| 2003/0225073 A1 | 12/2003 | Bebbington et al. |
| 2003/0225151 A1 | 12/2003 | Hale et al. |
| 2004/0002496 A1 | 1/2004 | Bebbington et al. |
| 2004/0009974 A1 | 1/2004 | Bebbington et al. |
| 2004/0009981 A1 | 1/2004 | Bebbington et al. |
| 2004/0009983 A1 | 1/2004 | Cox et al. |
| 2004/0010027 A1 | 1/2004 | Casuscelli et al. |
| 2004/0019046 A1 | 1/2004 | Pevarello et al. |
| 2004/0024040 A1 | 2/2004 | Green et al. |
| 2004/0029157 A1 | 2/2004 | Tatsuka et al. |
| 2004/0029857 A1 | 2/2004 | Hale et al. |
| 2004/0029885 A1 | 2/2004 | Bauer et al. |
| 2004/0049032 A1 | 3/2004 | Charrier et al. |
| 2004/0053931 A1 | 3/2004 | Cox et al. |
| 2004/0054179 A1 | 3/2004 | Yura et al. |
| 2004/0063715 A1 | 4/2004 | Paruch et al. |
| 2004/0082631 A1 | 4/2004 | Hale et al. |
| 2004/0097501 A1 | 5/2004 | Bebbington et al. |
| 2004/0097531 A1 | 5/2004 | Ledeboer et al. |
| 2004/0102360 A1 | 5/2004 | Barnett et al. |
| 2004/0102506 A1 | 5/2004 | Hale et al. |
| 2004/0106615 A1 | 6/2004 | Cochran et al. |
| 2004/0106667 A1 | 6/2004 | Damour et al. |
| 2004/0110741 A1 | 6/2004 | Bergmanis et al. |
| 2004/0116454 A1 | 6/2004 | Davies et al. |
| 2004/0147524 A1 | 7/2004 | Bauer |
| 2004/0157893 A1 | 8/2004 | Bebbington et al. |
| 2004/0167121 A1 | 8/2004 | Aronov |
| 2004/0167124 A1 | 8/2004 | Chen |
| 2004/0167141 A1 | 8/2004 | Bebbington et al. |
| 2004/0176380 A1 | 9/2004 | Hoffmann |
| 2004/0180881 A1 | 9/2004 | Berta |
| 2004/0198737 A1 | 10/2004 | Cox |
| 2004/0214814 A1 | 10/2004 | Bebbington |
| 2004/0220200 A1 | 11/2004 | Maltais |
| 2004/0224944 A1 | 11/2004 | Bebbington |
| 2004/0229875 A1 | 11/2004 | Cao |
| 2004/0235867 A1 | 11/2004 | Bilodeau |
| 2004/0235919 A1 | 11/2004 | Pevarello |
| 2004/0242559 A1 | 12/2004 | Ugolini |
| 2004/0242613 A1 | 12/2004 | Cardozo |
| 2004/0248853 A1 | 12/2004 | Dyckman |
| 2004/0254177 A1 | 12/2004 | Amici |
| 2004/0265852 A1 | 12/2004 | Plowman |
| 2005/0002938 A1 | 1/2005 | Plowman |
| 2005/0004110 A1 | 1/2005 | Bebbington |
| 2005/0004152 A1 | 1/2005 | Cochran |
| 2005/0004176 A1 | 1/2005 | Dyckman |
| 2005/0009876 A1 | 1/2005 | Bhagwat |
| 2005/0014760 A1 | 1/2005 | Hoffmann |
| 2005/0014761 A1 | 1/2005 | Hoffmann |
| 2005/0020583 A1 | 1/2005 | Pulici |
| 2005/0026984 A1 | 2/2005 | Bigot et al. |
| 2005/0026991 A1 | 2/2005 | Cholody et al. |
| 2005/0032839 A1 | 2/2005 | Fancelli et al. |
| 2005/0032869 A1 | 2/2005 | Berta et al. |
| 2005/0038023 A1 | 2/2005 | Bebbington et al. |
| 2005/0043323 A1 | 2/2005 | Vanotti et al. |
| 2005/0043346 A1 | 2/2005 | Vanotti et al. |
| 2005/0059657 A1 | 3/2005 | Cavicchioli |
| 2005/0059722 A1 | 3/2005 | Damour |
| 2005/0065169 A1 | 3/2005 | Wang |
| 2005/0065171 A1 | 3/2005 | Shakespeare |
| 2005/0070561 A1 | 3/2005 | Jung |
| 2005/0085490 A1 | 4/2005 | Wang |
| 2005/0085531 A1 | 4/2005 | Hodge |
| 2005/0107386 A1 | 5/2005 | Narla |
| 2005/0113460 A1 | 5/2005 | Glick |
| 2005/0124640 A1 | 6/2005 | Cardozo |
| 2005/0125852 A1 | 6/2005 | Caenepeel |
| 2005/0130977 A1 | 6/2005 | Lindsley |
| 2005/0137171 A1 | 6/2005 | Cherrier |
| 2005/0137199 A1 | 6/2005 | Jin |
| 2005/0137201 A1 | 6/2005 | Aronov |
| 2005/0143402 A1 | 6/2005 | Cheetham |
| 2005/0170442 A1 | 8/2005 | Kupcho |

FOREIGN PATENT DOCUMENTS

| | | |
|---|---|---|
| FR | 1 242 962 | 10/1960 |
| FR | 2818278 | 6/2002 |
| GB | 828 847 | 2/1960 |
| JP | 57209272 | 12/1982 |
| WO | WO 98/18782 A1 | 5/1988 |
| WO | WO 98/28281 A1 | 7/1998 |
| WO | WO 98/41512 A1 | 9/1998 |
| WO | WO 99/37788 | 7/1999 |
| WO | WO 01/07466 A1 | 2/2001 |
| WO | WO 01/21594 A1 | 3/2001 |
| WO | WO 01/21595 A1 | 3/2001 |
| WO | WO 01/21596 A1 | 3/2001 |
| WO | WO 01/21597 A1 | 3/2001 |
| WO | WO 01/32653 A1 | 5/2001 |
| WO | WO 01/47922 A2 | 7/2001 |
| WO | WO 01/47922 A3 | 7/2001 |
| WO | WO 01/55116 A2 | 8/2001 |
| WO | WO 01/55116 A3 | 8/2001 |
| WO | WO 01/56993 A2 | 8/2001 |
| WO | WO 01/56993 A3 | 8/2001 |
| WO | WO 01/57022 A2 | 8/2001 |
| WO | WO 01/57022 A3 | 8/2001 |
| WO | WO 01/98299 A1 | 12/2001 |
| WO | WO 02/00649 A1 | 1/2002 |
| WO | WO 02/12242 A2 | 2/2002 |
| WO | WO 02/22601 A1 | 3/2002 |
| WO | WO 02/22602 A2 | 3/2002 |
| WO | WO 02/22602 A3 | 3/2002 |
| WO | WO 02/22603 A1 | 3/2002 |
| WO | WO 02/22604 A1 | 3/2002 |
| WO | WO 02/22605 A1 | 3/2002 |
| WO | WO 02/22606 A1 | 3/2002 |
| WO | WO 02/22607 A1 | 3/2002 |
| WO | WO 02/22608 A1 | 3/2002 |
| WO | WO 02/48114 A1 | 6/2002 |
| WO | WO 02/50065 A2 | 6/2002 |
| WO | WO 02/50065 A3 | 6/2002 |
| WO | WO 02/50066 A2 | 6/2002 |
| WO | WO 02/50066 A3 | 6/2002 |
| WO | WO 02/057259 A2 | 7/2002 |
| WO | WO 02/057259 A3 | 8/2002 |
| WO | WO 02/059111 A2 | 8/2002 |
| WO | WO 02/059111 A3 | 8/2002 |
| WO | WO 02/059112 A2 | 8/2002 |
| WO | WO 02/059112 A3 | 8/2002 |
| WO | WO 02/062789 A1 | 8/2002 |

| | | |
|---|---|---|
| WO | WO 02/062804 A1 | 8/2002 |
| WO | WO 02/064586 A2 | 8/2002 |
| WO | WO 02/064586 A3 | 8/2002 |
| WO | WO 02/066461 A1 | 8/2002 |
| WO | WO 02/068415 A1 | 9/2002 |
| WO | WO 02/079192 | 10/2002 |
| WO | WO 02/083654 A1 | 10/2002 |
| WO | WO 02/096867 A2 | 12/2002 |
| WO | WO 02/096867 A3 | 12/2002 |
| WO | WO 02/096905 A1 | 12/2002 |
| WO | WO 03/000688 A1 | 1/2003 |
| WO | WO 03/008365 A2 | 1/2003 |
| WO | WO 03/009852 | 2/2003 |
| WO | WO 03/011287 A1 | 2/2003 |
| WO | WO 03/020276 A1 | 3/2003 |
| WO | WO 03/028720 A1 | 4/2003 |
| WO | WO 03/031606 A2 | 4/2003 |
| WO | WO 03/031606 A3 | 4/2003 |
| WO | WO 03/051358 A1 | 6/2003 |
| WO | WO 03/055491 A1 | 7/2003 |
| WO | WO 03/077921 A1 | 9/2003 |
| WO | WO 03/078402 A1 | 9/2003 |
| WO | WO 03/078423 | 9/2003 |
| WO | WO 03/078426 A1 | 9/2003 |
| WO | WO 03/078427 A1 | 9/2003 |
| WO | WO 03/087395 A2 | 10/2003 |
| WO | WO 03/087395 A3 | 10/2003 |
| WO | WO 03/091246 A1 | 11/2003 |
| WO | WO 03/092607 A2 | 11/2003 |
| WO | WO 03/092607 A3 | 11/2003 |
| WO | WO 03/097610 A1 | 11/2003 |
| WO | WO 03/106417 A1 | 12/2003 |
| WO | WO 03/106500 A1 | 12/2003 |
| WO | WO 03/107002 A1 | 12/2003 |
| WO | WO 2004/000833 A1 | 12/2003 |
| WO | WO 2004/005283 A1 | 1/2004 |
| WO | WO 2004/006838 A2 | 1/2004 |
| WO | WO 2004/007504 A1 | 1/2004 |
| WO | WO 2004/013144 A1 | 2/2004 |
| WO | WO 2004/013146 A1 | 2/2004 |
| WO | WO 2004/014374 A1 | 2/2004 |
| WO | WO 2004/037814 A1 | 5/2004 |
| WO | WO 2004/043953 A1 | 5/2004 |
| WO | WO 2004/055019 A1 | 7/2004 |
| WO | WO 2004/056812 A1 | 7/2004 |
| WO | WO 2004/056827 A2 | 7/2004 |
| WO | WO 2004/058752 A1 | 7/2004 |
| WO | WO 2004/058781 A1 | 7/2004 |
| WO | WO 2004/058782 A1 | 7/2004 |
| WO | WO 2004/066919 A2 | 8/2004 |
| WO | WO 2004/067516 A1 | 8/2004 |
| WO | WO 2004/070062 A2 | 8/2004 |
| WO | WO 2004/071390 A2 | 8/2004 |
| WO | WO 2004/071507 A1 | 8/2004 |
| WO | WO 2004/076454 A1 | 9/2004 |
| WO | WO 2004/080457 A1 | 9/2004 |
| WO | WO 2004/083203 A1 | 9/2004 |
| WO | WO 2004/087056 A2 | 10/2004 |
| WO | WO 2004/087707 A1 | 10/2004 |
| WO | WO 2004/090106 A2 | 10/2004 |
| WO | WO 2004/094410 A1 | 11/2004 |
| WO | WO 2004/096129 A2 | 11/2004 |
| WO | WO 2004/096130 A2 | 11/2004 |
| WO | WO 2004/096131 A2 | 11/2004 |
| WO | WO 2004/096135 A2 | 11/2004 |
| WO | WO 2004/098518 A2 | 11/2004 |
| WO | WO 2004/098528 A2 | 11/2004 |
| WO | WO 2004/099156 A1 | 11/2004 |
| WO | WO 2004/104007 A1 | 12/2004 |
| WO | WO 2004/105764 A1 | 12/2004 |
| WO | WO 2004/113324 A1 | 12/2004 |
| WO | WO 2005/002552 A2 | 1/2005 |
| WO | WO 2005/002571 A1 | 1/2005 |
| WO | WO 2005/002576 A2 | 1/2005 |
| WO | WO 2005/004988 A2 | 1/2005 |
| WO | WO 2005/005414 A2 | 1/2005 |
| WO | WO 2005/005427 A1 | 1/2005 |
| WO | WO 2005/005438 A1 | 1/2005 |
| WO | WO 2005/007641 A1 | 1/2005 |
| WO | WO 2005/009348 A2 | 2/2005 |
| WO | WO 2005/009987 A1 | 2/2005 |
| WO | WO 2005/011675 A1 | 2/2005 |
| WO | WO 2005/012262 A1 | 2/2005 |
| WO | WO 2005/012280 A1 | 2/2005 |
| WO | WO 2005/012298 A1 | 2/2005 |
| WO | WO 2005/016252 A2 | 2/2005 |
| WO | WO 2005/019190 A2 | 3/2005 |
| WO | WO 2005/026150 A1 | 3/2005 |
| WO | WO 2005/026155 A1 | 3/2005 |
| WO | WO 2005/026156 A1 | 3/2005 |
| WO | WO 2005/026157 A1 | 3/2005 |
| WO | WO 2005/027907 A1 | 3/2005 |
| WO | WO 2005/028475 A2 | 3/2005 |
| WO | WO 2005/033102 | 4/2005 |
| WO | WO 2005/034840 A2 | 4/2005 |
| WO | WO 2005/035527 A1 | 4/2005 |
| WO | WO 2005/037797 A1 | 4/2005 |
| WO | WO 2005/037825 A2 | 4/2005 |
| WO | WO 2005/037843 A1 | 4/2005 |
| WO | WO 2005/040133 A1 | 5/2005 |
| WO | WO 2005/040159 A1 | 5/2005 |
| WO | WO 2005/040368 | 5/2005 |
| WO | WO 2005/042525 A1 | 5/2005 |
| WO | WO 2005/044270 A1 | 5/2005 |
| WO | WO 2005/047266 A1 | 5/2005 |
| WO | WO 2005/049033 A1 | 6/2005 |
| WO | WO 2005/051308 | 6/2005 |
| WO | WO 2005/051942 | 6/2005 |
| WO | WO 2005/105788 A2 | 11/2005 |

OTHER PUBLICATIONS

Database Registry ACS; Oct. 9, 2000; XP002368780, retrieved from STN, Database accession No. 293763-18-5/RN abstract.

Database Registry ACS; Mar. 18, 2002; XP002368781, retrieved from STN, Database accession No. 401622-65-9/RN abstract.

Database Registry ACS; Apr. 10, 2001; XP002368782, retrieved from STN, Database accession No. 330683-80-2/RN abstract.

Database Registry ACS; Feb. 8, 2001; XP002368783, retrieved from STN, Database accession No. 320741-28-4/RN abstract.

Database Registry ACS; Jan. 11, 2001; XP002368784, retrieved from STN, Database accession No. 313549-01-8/RN abstract.

Database Registry ACS; Jan. 11, 2001; XP002368785, retrieved from STN, Database accession No. 313522-23-5/RN abstract.

Database Registry ACS; Jan. 4, 2001; XP002368786, retrieved from STN, Database accession No. 312755-54-7/RN abstract.

Database HCAPLUS ACS; XP002368787, retrieved from STN, Database accession No. 57:76580/DN abstract RN95936-94-0 & Sabata, B.K. et al.: Journal of Scientific and Industrial Research, Section B: Physical Sciences, vol. 21B, 1962, pp. 227-229.

Database HCAPLUS ACS; XP002368788, retrieved from STN, Database accession No. 91:176650/DN abstract RN7811-83-1 & Vavrova, Jaroslava et al.: Collection of Czechoslovak Chemical Communications, vol. 44, 1979, pp. 1413-1422.

Database CAPLUS, Chemical Abstracts Service, Columbus, Ohio, US: XP002368789 retrieved from STN, Database accession No. 135:332604/DN abstract RN369597-42-2, -43-3 & JP 2001 294772 A, Oct. 23, 2001.

Drobnic-Kosorok, M. et al., "Transformations of Some Substituted Methylene Heterocycles with Some Nucleophiles (1)", Journal of Heterocyclic Chemistry, vol. 13, 1976, pp. 1279-1282, XP008060243.

Kurasawa, Y. et al., "A Facile Synthesis of Novel Heterocycle-Conjugated Quinoxalines", Heterocycles vol. 22, No. 5, 1984, pp. 1189-1193, XP008059222 ISSN: 0385-5414.

Kurasawa, Y. et al., "A New Synthesis of 1,5-Dihydropyridazino[3,4-b]quinoxalines and 2-(Pyrazol-4-yl) quinoxalines", J. Heterocyclic Chemistry, vol. 33, 1996, pp. 757-762, XP008060252.

CAS RNS 85144-71-4 and 85144-70-3, Feb. 2008.

* cited by examiner

KINASE INHIBITORS

RELATED APPLICATION

This application claims the benefit of U.S. Provisional Application No. 60/531,202, filed Dec. 19, 2003, which is incorporated herein by reference.

FIELD OF THE INVENTION

The invention relates to compounds that may be used to inhibit kinases as well as compositions of matter and kits comprising these compounds. The present invention also relates to methods for inhibiting kinases as well as treatment methods using compounds according to the present invention.

BACKGROUND OF THE INVENTION

The invention relates to inhibitors of enzymes that catalyze phosphoryl transfer and/or that bind ATP/GTP nucleotides, compositions comprising the inhibitors, and methods of using the inhibitors and inhibitor compositions. The inhibitors and compositions comprising them are useful for treating or modulating disease in which phosphoryl transferases, including kinases, may be involved, symptoms of such disease, or the effect of other physiological events mediated by phosphoryl transferases, including kinases. The invention also provides for methods of making the inhibitor compounds and methods for treating diseases in which one or more phosphoryl transferase, including kinase, activities is involved.

Phosphoryl transferases are a large family of enzymes that transfer phosphorous-containing groups from one substrate to another. By the conventions set forth by the Nomenclature Committee of the International Union of Biochemistry and Molecular Biology (IUBMB) enzymes of this type have Enzyme Commission (EC) numbers starting with 2.7.-.- (See, Bairoch A., The ENZYME database in Nucleic Acids Res. 28: 204-305 (2000)). Kinases are a class of enzymes that function in the catalysis of phosphoryl transfer. The protein kinases constitute the largest subfamily of structurally related phosphoryl transferases and are responsible for the control of a wide variety of signal transduction processes within the cell. (See, Hardie, G. and Hanks, S. (1995) The Protein Kinase Facts Book, I and II, Academic Press, San Diego, Calif.). Protein kinases are thought to have evolved from a common ancestral gene due to the conservation of their structure and catalytic function. Almost all kinases contain a similar 250-300 amino acid catalytic domain. The protein kinases may be categorized into families by the substrates they phosphorylate (e.g., protein-tyrosine, protein-serine/threonine, histidine, etc.). Protein kinase sequence motifs have been identified that generally correspond to each of these kinase families (See, for example, Hanks, S. K.; Hunter, T., FASEB J. 9: 576-596 (1995); Kinghton et al., Science, 253: 407-414 (1991); Hiles et al., Cell 70: 419-429 (1992); Kunz et al., Cell, 73: 585-596 (1993); Garcia-Bustos et al., EMBO J., 13: 2352-2361 (1994)). Lipid kinases (e.g. PI3K) constitute a separate group of kinases with structural similarity to protein kinases.

Protein and lipid kinases regulate many different cell processes including, but not limited to, proliferation, growth, differentiation, metabolism, cell cycle events, apoptosis, motility, transcription, translation and other signaling processes, by adding phosphate groups to targets such as proteins or lipids. Phosphorylation events catalyzed by kinases act as molecular on/off switches that can modulate or regulate the biological function of the target protein. Phosphorylation of target proteins occurs in response to a variety of extracellular signals (hormones, neurotransmitters, growth and differentiation factors, etc.), cell cycle events, environmental or nutritional stresses, etc. Protein and lipid kinases can function in signaling pathways to activate or inactivate, or modulate the activity of (either directly or indirectly) the targets. These targets may include, for example, metabolic enzymes, regulatory proteins, receptors, cytoskeletal proteins, ion channels or pumps, or transcription factors. Uncontrolled signaling due to defective control of protein phosphorylation has been implicated in a number of diseases and disease conditions, including, for example, inflammation, cancer, allergy/asthma, diseases and conditions of the immune system, disease and conditions of the central nervous system (CNS), cardiovascular disease, dermatology, and angiogenesis.

Initial interest in protein kinases as pharmacological targets was stimulated by the findings that many viral oncogenes encode structurally modified cellular protein kinases with constitutive enzyme activity. These findings pointed to the potential involvement of oncogene related protein kinases in human proliferatives disorders. Subsequently, deregulated protein kinase activity, resulting from a variety of more subtle mechanisms, has been implicated in the pathophysiology of a number of important human disorders including, for example, cancer, CNS conditions, and immunologically related diseases. The development of selective protein kinase inhibitors that can block the disease pathologies and/or symptoms resulting from aberrant protein kinase activity has therefore generated much interest.

Cancer results from the deregulation of the normal processes that control cell division, differentiation and apoptotic cell death. Protein kinases play a critical role in this regulatory process. A partial non-limiting list of such kinases includes abl, AIK, AIK-2, AIK-3, ATK, bcr-abl, Blk, Brk, Btk, c-Kit, c-Met, c-Src, CDK1, CDK2, CDK4, CDK6, cRaf1, CSF1R, CSK, EGFR, ErbB3, ErbB3, ErbB4, ERK, Fak, fes, FGFR1, FGFR2, FGFR3, FGFR4, FGFR5, Fgr, FLK-4, Flt-1, Fps, Frk, Fyn, Hck, IGF-1R, INS-R, Jak, KDR, Lck, Lyn, MEK, p38, PDGFR, PIK, PKC, PYK2, Ros, Tie1, Tie2, Trk, Yes and Zap70. In mammalian biology, such protein kinases comprise mitogen activated protein kinase (MAPK) signaling pathways. MAPK signaling pathways are inappropriately activated by a variety of common disease-associated mechanisms such as mutation of ras genes and deregulation of growth factor receptors (Magnuson et al., Seminars in Cancer Biology 5: 247-252 (1994)). Therefore the inhibition of protein kinases is an object of the present invention.

Aurora-2 (AIK) is a serine/Threonine protein kinase that has been implicated in human cancer, such as colon, breast and other solid tumors. AIK is believed to be involved in protein phosphorylation events that regulate the cell cycle. Specifically, AIK may play a role in controlling the accurate segregation of chromosomes during mitosis. Misregulation of the cell cycle can lead to cellular proliferation and other abnormalities. In human colon caner tissue, the AIK protein has been found to be overexpressed (See, Bischoff et al., EMBO J., 17: 3052-3065 (1998); Schumacher et al., J. Cell Biol. 143: 1635-1646 (1998); Kimura et al., J. Biol. Chem., 272: 13766-13771 (1997)).

There is a continued need to find new therapeutic agents to treat human diseases. The protein kinases, specifically but not limited to Aurora-2, are especially attractive targets for the discovery of new therapeutics due to their important role in cancer, diabetes, Alzheimer's disease and other diseases.

SUMMARY OF THE INVENTION

The present invention relates to compounds that have activity for inhibiting kinases. The present invention also provides compositions, articles of manufacture and kits comprising these compounds.

In one embodiment, a pharmaceutical composition is provided that comprises a kinase inhibitor according to the present invention as an active ingredient. Pharmaceutical compositions according to the invention may optionally comprise 0.001%-100% of one or more kinase inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with kinases.

In one embodiment, a kit is provided that comprises a composition comprising at least one kinase inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one kinase inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit kinases.

In another embodiment, the compounds, compositions, kits and articles of manufacture are used to treat a disease state for which kinases possesses activity that contributes to the pathology and/or symptomology of the disease state.

In another embodiment, a compound is administered to a subject wherein kinases activity within the subject is altered, preferably reduced.

In another embodiment, a prodrug of a compound is administered to a subject that is converted to the compound in vivo where it inhibits kinases.

In another embodiment, a method of inhibiting kinases is provided that comprises contacting kinases with a compound according to the present invention.

In another embodiment, a method of inhibiting kinases is provided that comprises causing a compound according to the present invention to be present in a subject in order to inhibit kinases in vivo.

In another embodiment, a method of inhibiting kinases is provided that comprises administering a first compound to a subject that is converted in vivo to a second compound wherein the second compound inhibits kinases in vivo. It is noted that the compounds of the present invention may be the first or second compounds.

In another embodiment, a therapeutic method is provided that comprises administering a compound according to the present invention.

In another embodiment, a method of inhibiting cell proliferation is provided that comprises contacting a cell with an effective amount of a compound according to the present invention.

In another embodiment, a method of inhibiting cell proliferation in a patient is provided that comprises administering to the patient a therapeutically effective amount of a compound according to the present invention.

In another embodiment, a method of treating a condition in a patient which is known to be mediated by kinases, or which is known to be treated by kinase inhibitors, comprising administering to the patient a therapeutically effective amount of a compound according to the present invention.

In another embodiment, a method is provided for using a compound according to the present invention in order to manufacture a medicament for use in the treatment of disease state which is known to be mediated by kinases, or which is known to be treated by kinase inhibitors.

In another embodiment, a method is provided for treating a disease state for which kinases possesses activity that contributes to the pathology and/or symptomology of the disease state, the method comprising: causing a compound according to the present invention to be present in a subject in a therapeutically effective amount for the disease state.

In another embodiment, a method is provided for treating a disease state for which kinases possesses activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which kinases possesses activity that contributes to the pathology and/or symptomology of the disease state, the method comprising: administering a compound according to the present invention to a subject such that the compound is present in the subject in a therapeutically effective amount for the disease state.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well know in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting kinases and thus may themselves be prodrugs for another compound. Such prodrugs of another compound may or may not themselves independently have kinase inhibitory activity.

Definitions

Unless otherwise stated, the following terms used in the specification and claims shall have the following meanings for the purposes of this Application.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with C3-C8 rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with oxygen (See "oxaalkyl") or nitrogen atoms (See "aminoalkyl") between the carbon atoms. $C_X$alkyl and $C_{X-Y}$alkyl are typically used where X and Y indicate the number of carbon atoms in the chain. For example, $C_{1-6}$ alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl) means a straight or branched, saturated or unsaturated aliphatic divalent radical having the number of atoms indicated or when no atoms are indicated means a bond (e.g., $(C_{6-10})$aryl$(C_{1-3})$alkyl includes, benzyl, phenethyl, 1-phenylethyl, 3-phenylpropyl, 2-thienylmethyl, 2-pyridinylmethyl and the like).

"Alkylene", unless indicated otherwise, means a straight or branched, saturated or unsaturated, aliphatic, divalent radical. $C_X$alkylene and $C_{X-Y}$alkylene are typically used where X and Y indicate the number of carbon atoms in the chain. For example, $C_{1-6}$ alkylene includes methylene (—$CH_2$—), ethylene (—$CH_2CH_2$—), trimethylene (—$CH_2CH_2CH_2$—), tetramethylene (—$CH_2CH_2CH_2CH_2$—) 2-butenylene (—$CH_2CH=CHCH_2$—), 2-methyltetramethylene (—$CH_2CH(CH_3)CH_2CH_2$—), pentamethylene (—$CH_2CH_2CH_2CH_2CH_2$—) and the like).

"Alkylidene" means a straight or branched saturated or unsaturated, aliphatic radical connected to the parent molecule by a double bond. $C_X$alkylidene and $C_{X-Y}$alkylidene are typically used where X and Y indicate the number of carbon atoms in the chain. For example, $C_{1-6}$ alkylidene includes methylene (=$CH_2$), ethylidene (=$CHCH_3$), isopropylidene (=$C(CH_3)_2$), propylidene (=$CHCH_2CH_3$), allylidene (=$CH$—$CH$=$CH_2$), and the like).

"Amino" means a nitrogen moiety having two further substituents where, for example, a hydrogen or carbon atom is attached to the nitrogen. For example, representative amino groups include —$NH_2$, —$NHCH_3$, —$N(CH_3)_2$, —$NHC_{1-10}$-alkyl, —$N(C_{1-10}$-alkyl$)_2$, —NHaryl, —NHheteroaryl, —$N(aryl)_2$, —$N(heteroaryl)_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aminoalkyl" means an alkyl, as defined above, except where one or more substituted or unsubstituted nitrogen atoms (—N—) are positioned between carbon atoms of the alkyl. For example, an $(C_{2-6})$ aminoalkyl refers to a chain comprising between 2 and 6 carbons and one or more nitrogen atoms positioned between the carbon atoms.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are $sp^2$ hybridized and the total number of pi electrons is equal to 4n+2. An aromatic ring may be such that the ring atoms are only carbon atoms or may include carbon and non-carbon atoms (see Heteroaryl).

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $C_X$aryl and $C_{X-Y}$aryl are typically used where X and Y indicate the number of atoms in the ring.

"Bicycloalkyl" means a saturated or partially unsaturated fused bicyclic or bridged polycyclic ring assembly.

"Bicycloaryl" means a bicyclic ring assembly wherein the rings are linked by a single bond or fused and at least one of the rings comprising the assembly is aromatic. $C_X$bicycloaryl and $C_{X-Y}$ bicycloaryl are typically used where X and Y indicate the number of carbon atoms in the bicyclic ring assembly and directly attached to the ring.

"Bridging ring" as used herein refers to a ring that is bonded to another ring to form a compound having a bicyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NR$_a$R$_b$ where R$_a$ and R$_b$ are each independently two further substituents where a hydrogen or carbon atom is attached to the nitrogen.

"Carbocycle" means a ring consisting of carbon atoms.

"Carbocyclic ketone derivative" means a carbocyclic derivative wherein the ring contains a —CO— moiety.

"Carbonyl" means the radical —CO—. It is noted that the carbonyl radical may be further substituted with a variety of substituents to form different carbonyl groups including acids, acid halides, aldehydes, amides, esters, and ketones.

"Carboxy" means the radical —CO$_2$—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, fused bicyclic or bridged polycyclic ring assembly. C$_X$ cycloalkyl and C$_{X-Y}$ cycloalkyl are typically used where X and Y indicate the number of carbon atoms in the ring assembly. For example, C$_{3-10}$ cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

"Cycloalkylene" means a divalent saturated or partially unsaturated, monocyclic or polycyclic ring assembly. C$_X$ cycloalkylene and C$_{X-Y}$ cycloalkylene are typically used where X and Y indicate the number of carbon atoms in the ring assembly.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted (C$_{1-3}$)alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom" refers to an atom that is not a carbon atom. Particular examples of heteroatoms include, but are not limited to nitrogen, oxygen, and sulfur.

"Heteroatom moiety" includes a moiety where the atom by which the moiety is attached is not a carbon. Examples of heteroatom moieties include —N=, —NR$_c$—, —N$^+$(O$^-$)=, —O—, —S— or —S(O)$_2$—, wherein R$_c$ is further substituent.

"Heterobicycloalkyl" means bicycloalkyl, as defined in this Application, provided that one or more of the atoms within the ring is a heteroatom. For example hetero(C$_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like.

"Heterocycloalkylene" means cycloalkylene, as defined in this Application, provided that one or more of the ring member carbon atoms is replaced by a heteroatom.

"Heteroaryl" means a cyclic aromatic group having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted.

"Heterobicycloaryl" means bicycloaryl, as defined in this Application, provided that one or more of the atoms within the ring is a heteroatom. For example, hetero(C$_8$ I$_0$)bicycloaryl as used in this Application includes, but is not limited to, 2-amino-4-oxo-3,4-dihydropteridin-6-yl, tetrahydroisoquinolinyl, and the like.

"Heterocycloalkyl" means cycloalkyl, as defined in this Application, provided that one or more of the atoms forming the ring is a heteroatom selected, independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

"Hydroxy" means the radical —OH.

"Iminoketone derivative" means a derivative comprising the moiety —C(NR)—, wherein R comprises a hydrogen or carbon atom attached to the nitrogen.

"Isomers" mean any compound having an identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Nitro" means the radical —$NO_2$.

"Oxaalkyl" means an alkyl, as defined above, except where one or more oxygen atoms (—O—) are positioned between carbon atoms of the alkyl. For example, an ($C_{2-6}$)oxaalkyl refers to a chain comprising between 2 and 6 carbons and one or more oxygen atoms positioned between the carbon atoms.

"Oxoalkyl" means an alkyl, further substituted with a carbonyl group. The carbonyl group may be an aldehyde, ketone, ester, amide, acid or acid chloride.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of inhibitors of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound that is convertible in vivo metabolically into an inhibitor according to the present invention. The prodrug itself may or may not also have kinase inhibitory activity. For example, an inhibitor comprising a hydroxy group may be administered as an ester that is converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, an inhibitor comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, Protecting Groups in Organic Synthesis, 3rd edition, John Wiley & Sons, Inc. 1999.

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, ($C_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted.

"Sulfinyl" means the radical —SO—. It is noted that the sulfinyl radical may be further substituted with a variety of substituents to form different sulfinyl groups including sulfinic acids, sulfinamides, sulfinyl esters, and sulfoxides.

"Sulfonyl" means the radical —$SO_2$—. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thiocarbonyl" means the radical —CS—. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —$CH_3$) as well as —$CR_aR_bR_c$ where $R_a$, $R_b$, and $R_c$ may each independently be hydrogen or any other substituent where the atom attached to the carbon is a heteroatom or cyano. Hence, $CF_3$, $CH_2OH$ and $CH_2CN$, for example, are all $C_1$ alkyls.

Kinase Inhibitors

In one embodiment, there is provided a compound comprising the formula:

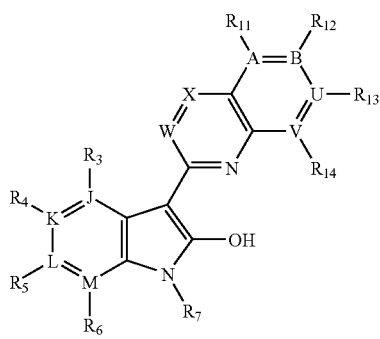

wherein:

$R_3$, $R_4$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_4$, $R_5$, and $R_6$ are taken together to form a ring, with the proviso that $R_3$, $R_4$, $R_5$, and $R_6$ are absent where the ring atom to which $R_3$, $R_4$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

A, B, U and V are each independently selected from the group consisting of C and N;

J, K, L and M are each independently selected from the group consisting of C and N;

W is selected from the group consisting of $CR_{21}$ and N;

X is selected from the group consisting of $CR_{15}$ and N;

$R_{15}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted; and $R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{20}$ and $R_{15}$ are taken together to form a ring, with the proviso that at least one of $R_3$, $R_4$, $R_5$, and $R_6$ is selected from the group consisting of —$NH_2$, furanyl, quinolinyl, indolyl, pyridinyl, carboxamidinyl, aminosulfonyl, and arylalkyl, each unsubstituted or substituted, or a substituted sulfonamidyl when A, B, U, V and W are all C; or X is $CR_{15}$ and $R_{15}$ is an N-linked moiety when A, B, U, V and W are all C; or X is $CR_{15}$ and $R_{15}$ is an S-linked moiety when A, B, U, V and W are all C.

In another embodiment, there is provided a compound comprising the formula:

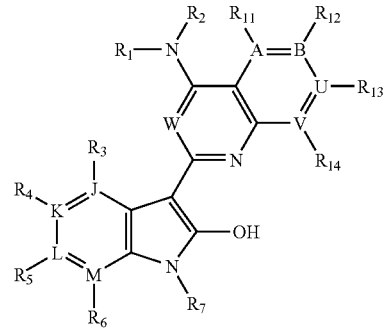

wherein:

$R_1$ and $R_2$ are selected from the group consisting of hydrogen, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_3$, $R_4$, $R_5$, and $R_6$ are each independently selected from the group consisting of hydrogen, halo, perhalo($C_{1-10}$)alkyl, amino, nitro, cyano, thio, sulfonamide, $(C_{1-10})$alkyl, $(C_{3-12})$cycloalkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_4$, $R_5$, and $R_6$ are taken together to form a ring, with the proviso that $R_3$, $R_4$, $R_5$, and $R_6$ are absent where the ring atom to which $R_3$, $R_4$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, $(C_{1-12})$alkyl, alkoxy, thio, hydroxy, $(C_{3-12})$cycloalkyl, hetero$(C_{3-12})$cycloalkyl, hetero$(C_{3-12})$cycloalkoxy, $(C_{9-12})$bicycloaryl, hetero$(C_{8-12})$bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

A, B, U and V are each independently selected from the group consisting of C and N;

J, K, L and M are each independently selected from the group consisting of C and N;

W is selected from the group consisting of $CR_{21}$ and N; and $R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_1$ are taken together to form a ring.

In yet another embodiment, there is provided a compound comprising the formula:

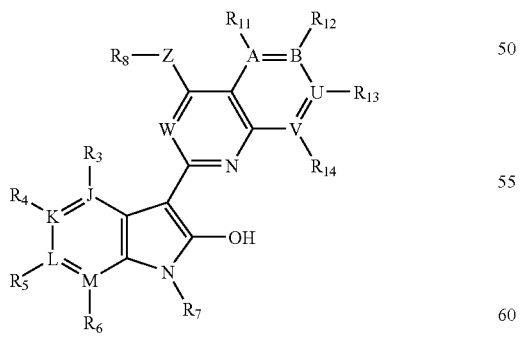

wherein:

$R_3$, $R_4$, $R_5$, and $R_6$ are each independently selected from the group consisting of hydrogen, halo, perhalo$(C_{1-10})$alkyl, amino, nitro, cyano, thio, sulfonamide, $(C_{1-10})$alkyl, $(C_{3-12})$cycloalkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_4$, $R_5$, and $R_6$ are taken together to form a ring, with the proviso that $R_3$, $R_4$, $R_5$, and $R_6$ are absent where the ring atom to which $R_3$, $R_4$, $R_5$, and $R_6$ are bound is nitrogen;

$R_7$ is hydrogen or a substituent convertible in vivo to hydrogen;

$R_8$ is selected from the group consisting of hydrogen, alkoxy, aryloxy, heteroaryloxy, carbonyl, amino, $(C_{1-10})$alkylamino, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{11}$, $R_{12}$, $R_{13}$, and $R_{14}$ are each independently selected from the group consisting of hydrogen, $(C_{1-12})$alkyl, alkoxy, thio, hydroxy, $(C_{3-12})$cycloalkyl, hetero$(C_{3-12})$cycloalkyl, hetero$(C_{3-12})$cycloalkoxy, $(C_{9-12})$bicycloaryl, hetero$(C_{8-12})$bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

A, B, U and V are each independently selected from the group consisting of C and N;

J, K, L and M are each independently selected from the group consisting of C and N;

W is selected from the group consisting of $CR_{21}$ and N;

$R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_8$ are taken together to form a ring; and Z is selected from the group consisting of S, SO, and $SO_2$.

In still another embodiment, there is provided a compound comprising the formula:

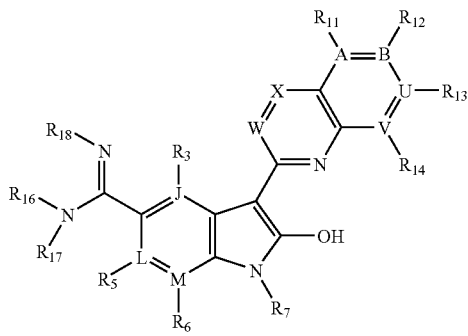

wherein:

$R_3$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{16}$ and $R_{17}$ are selected from the group consisting of hydrogen, hydroxy, alkoxy, aryloxy, heteroaryloxy, carbonyl, amino, sulfonamido, imino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{18}$ is selected from the group consisting of hydrogen, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

A, B, U and V are each independently selected from the group consisting of C and N;

J, L and M are each independently selected from the group consisting of C and N;

W is selected from the group consisting of $CR_{21}$ and N;

X is selected from the group consisting of $CR_{15}$ and N;

$R_{15}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted; and $R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{21}$ and $R_{15}$ are taken together to form a ring.

In a further embodiment, there is provided a compound comprising the formula:

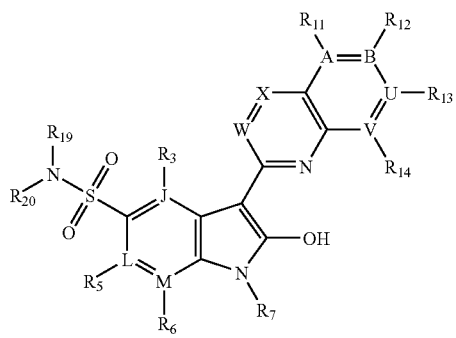

wherein:

$R_3$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, $(C_{1-12})$alkyl, alkoxy, thio, hydroxy, $(C_{3-12})$cycloalkyl, hetero$(C_{3-12})$cycloalkyl, hetero$(C_{3-12})$cycloalkoxy, $(C_{9-12})$bicycloaryl, hetero$(C_{8-12})$bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{19}$ and $R_{20}$ are selected from the group consisting of hydrogen, hydroxy, alkoxy, aryloxy, heteroaryloxy, carbonyl, amino, imino, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

A, B, U and V are each independently selected from the group consisting of C and N;

J, L and M are each independently selected from the group consisting of C and N;

W is selected from the group consisting of $CR_{21}$ and N;

X is selected from the group consisting of $CR_{15}$ and N;

$R_{15}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted; and $R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_{15}$ are taken together to form a ring.

In another embodiment, there is provided a compound comprising the formula:

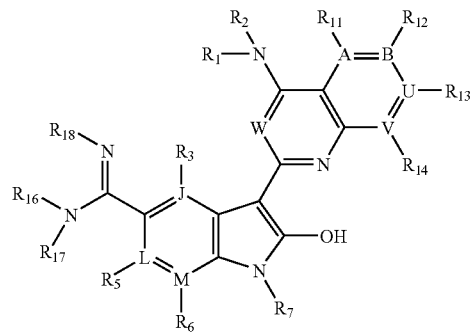

wherein:

$R_1$ and $R_2$ are selected from the group consisting of hydrogen, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_3$, $R_5$, and $R_6$ are each independently selected from the group consisting of hydrogen, halo, perhalo$(C_{1-10})$alkyl, amino, nitro, cyano, thio, sulfonamide, $(C_{1-10})$alkyl, $(C_{3-12})$cycloalkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, $(C_{1-12})$alkyl, alkoxy, thio, hydroxy, $(C_{3-12})$cycloalkyl, hetero$(C_{3-12})$cycloalkyl, hetero$(C_{3-12})$cycloalkoxy, $(C_{9-12})$bicycloaryl, hetero$(C_{8-12})$bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{16}$ and $R_{17}$ are selected from the group consisting of hydrogen, hydroxy, alkoxy, aryloxy, heteroaryloxy, carbonyl, amino, sulfonamido, imino, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{18}$ is selected from the group consisting of hydrogen, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

A, B, U and V are each independently selected from the group consisting of C and N;

J, L and M are each independently selected from the group consisting of C and N;

W is selected from the group consisting of $CR_{21}$ and N; and $R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl $(C_{1-5})$alkyl, perhalo$(C_{1-10})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_1$ are taken together to form a ring.

In yet another embodiment, there is provided a compound comprising the formula:

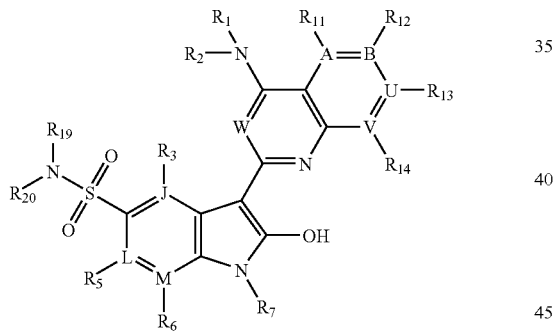

wherein:

$R_1$ and $R_2$ are selected from the group consisting of hydrogen, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_3$, $R_5$, and $R_6$ are each independently selected from the group consisting of hydrogen, halo, perhalo$(C_{1-10})$alkyl, amino, nitro, cyano, thio, sulfonamide, $(C_{1-10})$alkyl, $(C_{3-12})$cycloalkyl, hetero$(C_{3-12})$cycloalkyl, aryl$(C_{1-10})$alkyl, heteroaryl$(C_{1-5})$alkyl, $(C_{9-12})$bicycloaryl, hetero $(C_{4-12})$bicycloaryl, carbonyl$(C_{1-3})$alkyl, thiocarbonyl $(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, $(C_{1-12})$alkyl, alkoxy, thio, hydroxy, $(C_{3-12})$cycloalkyl, hetero$(C_{3-12})$cycloalkyl, hetero$(C_{3-12})$cycloalkoxy, $(C_{9-12})$bicycloaryl, hetero$(C_{8-12})$bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{19}$ and $R_{20}$ are selected from the group consisting of hydrogen, hydroxy, alkoxy, aryloxy, heteroaryloxy, carbonyl, amino, imino, $(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

A, B, U and V are each independently selected from the group consisting of C and N;

J, L and M are each independently selected from the group consisting of C and N;

W is selected from the group consisting of $CR_{21}$, and N; and $R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl $(C_{1-5})$alkyl, perhalo$(C_{1-10})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_1$ are taken together to form a ring.

In still another embodiment, there is provided a compound comprising the formula:

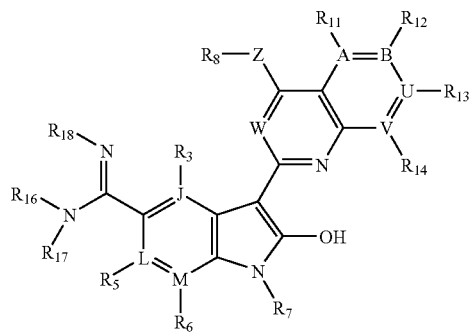

wherein:

$R_3$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_8$ is selected from the group consisting of hydrogen, alkoxy, aryloxy, heteroaryloxy, carbonyl, amino, ($C_{1-10}$) alkylamino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$) cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{16}$ and $R_{17}$ are selected from the group consisting of hydrogen, hydroxy, alkoxy, aryloxy, heteroaryloxy, carbonyl, amino, sulfonamido, imino, ($C_{1-10}$)alkyl, ($C_{3-12}$) cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{18}$ is selected from the group consisting of hydrogen, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

A, B, U and V are each independently selected from the group consisting of C and N;

J, L and M are each independently selected from the group consisting of C and N;

W is selected from the group consisting of $CR_{21}$ and N;

$R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{21}$ and $R_8$ are taken together to form a ring; and Z is selected from the group consisting of S, SO, and $SO_2$.

In a further embodiment, there is provided a compound comprising the formula:

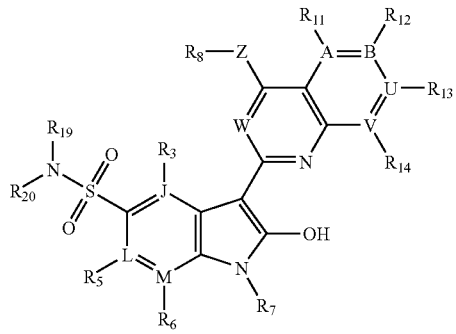

wherein:

$R_3$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$) alkyl, heteroaryl($C_{1-5}$)alkyl, ($C_{9-12}$)bicycloaryl, hetero ($C_{4-12}$)bicycloaryl, carbonyl($C_{1-3}$)alkyl, thiocarbonyl ($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_8$ is selected from the group consisting of hydrogen, alkoxy, aryloxy, heteroaryloxy, carbonyl, amino, ($C_{1-10}$)

alkylamino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{19}$ and $R_{20}$ are selected from the group consisting of hydrogen, hydroxy, alkoxy, aryloxy, heteroaryloxy, carbonyl, amino, imino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

A, B, U and V are each independently selected from the group consisting of C and N;

J, L and M are each independently selected from the group consisting of C and N;

W is selected from the group consisting of $CR_{21}$ and N;

$R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{21}$ and $R_8$ are taken together to form a ring; and Z is selected from the group consisting of S, SO, and $SO_2$.

In another embodiment, there is provided a compound comprising the formula:

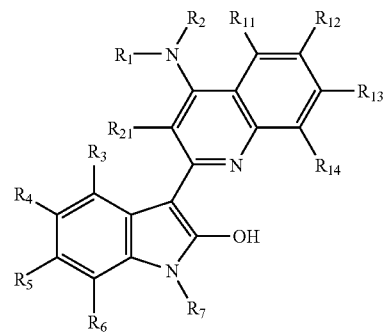

wherein:
$R_1$ and $R_2$ are selected from the group consisting of hydrogen, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_3$, $R_4$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_4$, $R_5$, and $R_6$ are taken together to form a ring, with the proviso that $R_3$, $R_4$, $R_5$, and $R_6$ are absent where the ring atom to which $R_3$, $R_4$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen; and $R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{21}$ and $R_1$ are taken together to form a ring.

In yet another embodiment, there is provided a compound comprising the formula:

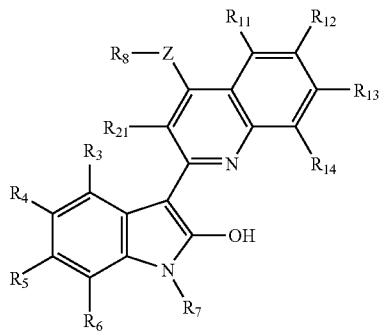

wherein:

$R_3$, $R_4$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$) alkyl, heteroaryl($C_{1-5}$)alkyl, ($C_{9-12}$)bicycloaryl, hetero ($C_{4-12}$)bicycloaryl, carbonyl($C_{1-3}$)alkyl, thiocarbonyl ($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_4$, $R_5$, and $R_6$ are taken together to form a ring, with the proviso that $R_3$, $R_4$, $R_5$, and $R_6$ are absent where the ring atom to which $R_3$, $R_4$, $R_5$, and $R_6$ are bound is nitrogen;

$R_7$ is hydrogen or a substituent convertible in vivo to hydrogen;

$R_8$ is selected from the group consisting of hydrogen, alkoxy, aryloxy, heteroaryloxy, carbonyl, amino, ($C_{1-10}$) alkylamino, ($C_{1-10}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$) cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{21}$ and $R_8$ are taken together to form a ring; and Z is selected from the group consisting of S, SO, and $SO_2$.

In still another embodiment, there is provided a compound comprising the formula:

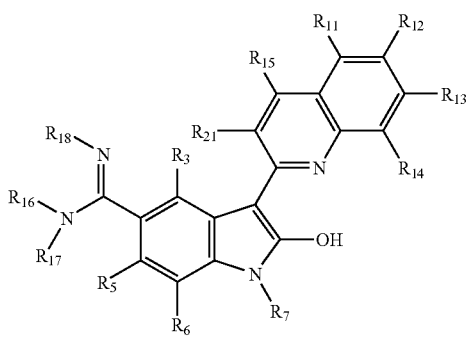

wherein:

$R_3$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$) alkyl, heteroaryl($C_{1-5}$)alkyl, ($C_{9-12}$)bicycloaryl, hetero ($C_{4-12}$)bicycloaryl, carbonyl($C_{1-3}$)alkyl, thiocarbonyl ($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$) cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{16}$ and $R_{17}$ are selected from the group consisting of hydrogen, hydroxy, alkoxy, aryloxy, heteroaryloxy, carbonyl, amino, sulfonamido, imino, ($C_{1-10}$)alkyl, ($C_{3-12}$) cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{18}$ is selected from the group consisting of hydrogen, hydroxy, alkoxy, aryloxy, heteroaryloxy, carbonyl, amino, sulfonamido, imino, sulfonyl, sulfinyl, $(C_{1-10})$ alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{15}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl $(C_{1-5})$alkyl, perhalo$(C_{1-10})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted; and $R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl $(C_{1-5})$alkyl, perhalo$(C_{1-10})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_{15}$ are taken together to form a ring.

In a further embodiment, there is provided a compound comprising the formula:

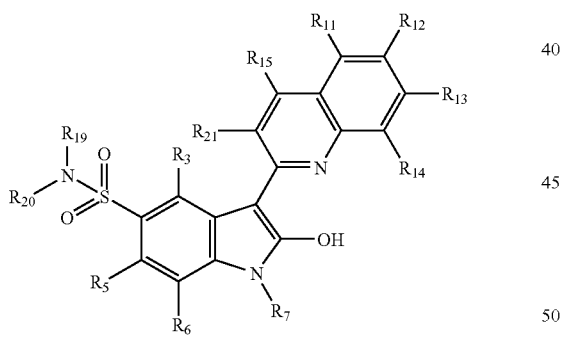

wherein:

$R_3$, $R_5$, and $R_6$ are each independently selected from the group consisting of hydrogen, halo, perhalo$(C_{1-10})$alkyl, amino, nitro, cyano, thio, sulfonamide, $(C_{1-10})$alkyl, $(C_{3-12})$cycloalkyl, hetero$(C_{3-12})$cycloalkyl, aryl$(C_{1-10})$ alkyl, heteroaryl$(C_{1-5})$alkyl, $(C_{9-12})$bicycloaryl, hetero $(C_{4-12})$bicycloaryl, carbonyl$(C_{1-3})$alkyl, thiocarbonyl $(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, $(C_{1-12})$alkyl, alkoxy, thio, hydroxy, $(C_{3-12})$cycloalkyl, hetero$(C_{3-12})$ cycloalkyl, hetero$(C_{3-12})$cycloalkoxy, $(C_{9-12})$bicycloaryl, hetero$(C_{8-12})$bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{19}$ and $R_{20}$ are selected from the group consisting of hydrogen, hydroxy, alkoxy, aryloxy, heteroaryloxy, carbonyl, amino, imino, $(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, aryl$(C_{1-10})$alkyl, heteroaryl$(C_{1-5})$ alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{15}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl $(C_{1-5})$alkyl, perhalo$(C_{1-10})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted; and $R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl $(C_{1-5})$alkyl, perhalo$(C_{1-10})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_{15}$ are taken together to form a ring.

In another embodiment, there is provided a compound comprising the formula:

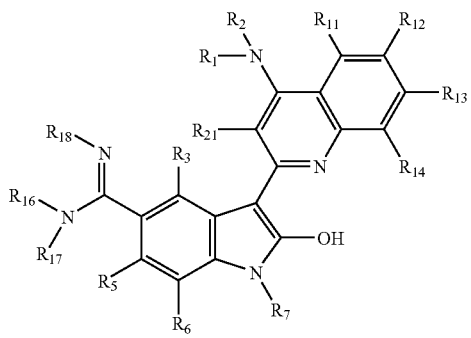

wherein:

$R_1$ and $R_2$ are selected from the group consisting of hydrogen, hydroxy, alkoxy, aryloxy, heteroaryloxy, carbonyl, amino, sulfonamido, imino, sulfonyl, sulfinyl, $(C_{1-10})$ alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_3$, $R_5$, and $R_6$ are each independently selected from the group consisting of hydrogen, halo, perhalo$(C_{1-10})$alkyl, amino, nitro, cyano, thio, sulfonamide, $(C_{1-10})$alkyl, $(C_{3-12})$cycloalkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, $(C_{1-12})$alkyl, alkoxy, thio, hydroxy, $(C_{3-12})$cycloalkyl, hetero$(C_{3-12})$cycloalkyl, hetero$(C_{3-12})$cycloalkoxy, $(C_{9-12})$bicycloaryl, hetero$(C_{8-12})$bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{16}$ and $R_{17}$ are selected from the group consisting of hydrogen, hydroxy, alkoxy, aryloxy, heteroaryloxy, carbonyl, amino, sulfonamido, imino, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{18}$ is selected from the group consisting of hydrogen, hydroxy, alkoxy, aryloxy, heteroaryloxy, carbonyl, amino, sulfonamido, imino, sulfonyl, sulfinyl, $(C_{1-10})$ alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$ bicycloaryl, and hetero$(C_{4-12})$bicycloaryl, each substituted or unsubstituted; and $R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_1$ are taken together to form a ring.

In yet another embodiment, there is provided a compound comprising the formula:

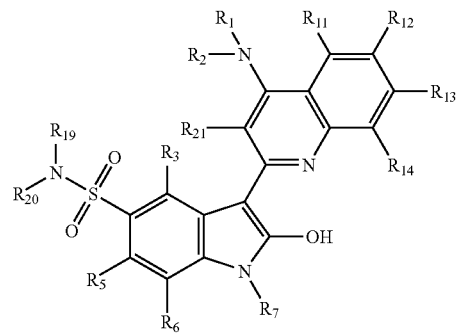

wherein:

$R_1$ and $R_2$ are selected from the group consisting of hydrogen, hydroxy, alkoxy, aryloxy, heteroaryloxy, carbonyl, amino, sulfonamido, imino, sulfonyl, sulfinyl, $(C_{1-10})$ alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_3$, $R_5$, and $R_6$ are each independently selected from the group consisting of hydrogen, halo, perhalo$(C_{1-10})$alkyl, amino, nitro, cyano, thio, sulfonamide, $(C_{1-10})$alkyl, $(C_{3-12})$cycloalkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, $(C_{9-12})$alkyl, alkoxy, thio, hydroxy, $(C_{3-12})$cycloalkyl, hetero$(C_{3-12})$cycloalkyl, hetero$(C_{3-12})$cycloalkoxy, $(C_{9-12})$bicycloaryl, hetero$(C_{8-12})$bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{19}$ and $R_{20}$ are selected from the group consisting of hydrogen, hydroxy, alkoxy, aryloxy, heteroaryloxy, carbonyl, amino, imino, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted; and $R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_1$ are taken together to form a ring.

In still another embodiment, there is provided a compound comprising the formula:

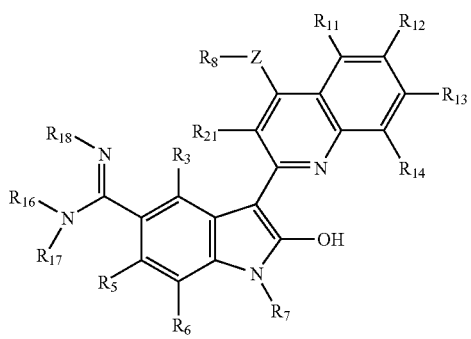

wherein:

$R_3$, $R_5$, and $R_6$ are each independently selected from the group consisting of hydrogen, halo, perhalo$(C_{1-10})$alkyl, amino, nitro, cyano, thio, sulfonamide, $(C_{1-10})$alkyl, $(C_{3-12})$cycloalkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_8$ is selected from the group consisting of hydrogen, alkoxy, aryloxy, heteroaryloxy, carbonyl, amino, $(C_{1-10})$alkylamino, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{11}$, $R_{12}$, $R_{13}$, and $R_{14}$ are each independently selected from the group consisting of hydrogen, $(C_{1-12})$alkyl, alkoxy, thio, hydroxy, $(C_{3-12})$cycloalkyl, hetero$(C_{3-12})$cycloalkyl, hetero$(C_{3-12})$cycloalkoxy, $(C_{9-12})$bicycloaryl, hetero$(C_{8-12})$bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{16}$ and $R_{17}$ are selected from the group consisting of hydrogen, hydroxy, alkoxy, aryloxy, heteroaryloxy, carbonyl, amino, sulfonamido, imino, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{18}$ is selected from the group consisting of hydrogen, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_8$ are taken together to form a ring; and Z is selected from the group consisting of S, SO, and $SO_2$.

In a further embodiment, there is provided a compound comprising the formula:

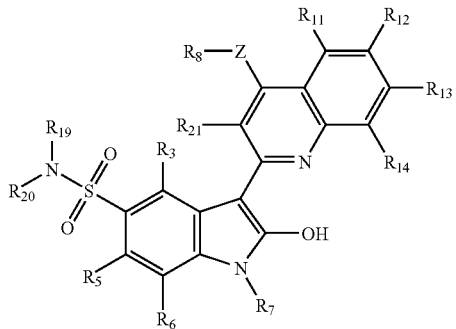

wherein:

$R_3$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_8$ is selected from the group consisting of hydrogen, alkoxy, aryloxy, heteroaryloxy, carbonyl, amino, ($C_{1-10}$)alkylamino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{19}$ and $R_{20}$ are selected from the group consisting of hydrogen, hydroxy, alkoxy, aryloxy, heteroaryloxy, carbonyl, amino, imino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{21}$ and $R_8$ are taken together to form a ring; and Z is selected from the group consisting of S, SO, and $SO_2$.

In another embodiment, there is provided a compound comprising the formula:

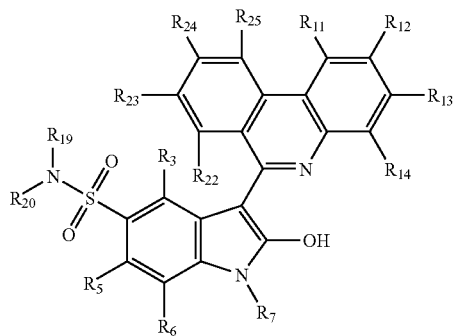

wherein:

$R_3$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{19}$ and $R_{20}$ are selected from the group consisting of hydrogen, hydroxy, alkoxy, aryloxy, heteroaryloxy, carbonyl, amino, imino, ($C_{1-10}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl($C_{1-10}$)alkyl, heteroaryl($C_{1-5}$) alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted; and $R_{22}$, $R_{23}$, $R_{24}$, and $R_{25}$ are each independently selected from the group consisting of hydrogen, ($C_{1-12}$)alkyl, alkoxy, thio, hydroxy, ($C_{3-12}$)cycloalkyl, hetero($C_{3-12}$) cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{22}$, $R_{23}$, $R_{24}$, and $R_{25}$ are taken together to form a ring, or $R_{25}$ and $R_{11}$ are taken together to form a ring.

In one variation of each of the above embodiments and variations, at least one of $R_4$ and $R_5$ is not H.

In one variation of each of the above embodiments and variations, X is $CR_{15}$. In particular variations, $R_{15}$ is an N-linked moiety. In other particular variations, $R_{15}$ is an S-linked moiety. In still other particular variations, $R_{15}$ is an unsubstituted or substituted amino.

In another variation, V is carbon and $R_{14}$ is hydrogen.

In one variation of each of the above embodiments and variations, J, K, L and M each comprise a carbon ring atom. In another variation, J, K and L each comprise a carbon ring atom and M is nitrogen.

In a further variation, two of J, K, L and M are taken together to form a further ring that is fused to the ring comprising J, K, L and M. In one particular variation, the fused ring is a substituted or unsubstituted 5 or 6 membered aryl or heteroaryl ring. In another particular variation, the fused ring is an alicyclic ring.

In another variation, W is N. In a further variation, W is CH. In still another variation, W is $CR_{21}$.

In another variation of each of the above embodiments and variations, the ring formed by J, K, L and M comprises substituents that form a ring fused to the ring formed by J, K, L and M.

In yet another variation, $R_{15}$ is selected from the group consisting of hydrogen, amino, F, Br, Cl, —$OCH_3$, —$SO_2Me$, —$SO_2NH_2$, —$SO_2NHMe$, —$SO_2NHCH_2CH_2OH$, —$SO_2NMe_2$, —$NHSO_2$(3-fluorophenyl), perhalo($C_{1-10}$) alkyl, —$OCF_3$, —$CF_3$, ($C_{1-10}$)alkyl, hydroxy-($C_{1-10}$)alkyl, aryl, aryl-($C_{1-10}$)alkyl, heteroaryl, aminosulfonyl, alkylsulfonyl, arylsulfonyl, heteroarylsulfonyl, hydroxy, aryloxy, heteroaryloxy, arylalkyl, heteroaryl($C_{1-10}$)alkyl, cycloalkyl, heterocycloalkyl, HS—, ($C_{1-6}$)alkylS-, cyano, nitro, cycloalkoxy, ($C_{1-12}$)alkoxy, —COOH, —$CO_2Me$, carboxamide, ($C_{1-12}$)alkylNHCO—, $R_9R_{10}N$—($C_{1-12}$)alkyl aminocarbonyl, $R_9R_{10}N$—($C_{1-12}$)alkoxycarbonyl, hetero-($C_{1-6}$) alkylaminocarbonyl, heterocycloalkyl-($C_{1-6}$)alkylCO—, heteroaryl-($C_{1-6}$)alkylCO—, heterocycloalkyl-($C_{1-6}$)alkylOCO—, heteroaryl-($C_{1-6}$)alkylOCO—, ($C_{1-6}$)alkylOCO—, diethoxyphosphorylmethyl, imino group, $R_9R_{10}N$—($C_{1-6}$) alkylsulfonyl, —$NH_2$, —$NHCH_3$, —$N(CH_3)_2$, —$NH(C_{1-3}$ alkyl, —$N(C_{1-3}$-alkyl)$_2$, $R_9R_{10}N$—($C_{1-12}$)alkyl aminocarbonylamino, $R_9R_{10}N$—($C_{1-6}$)alkyl alkoxycarbonylamino, heterocycloalkyl-($C_{1-6}$)alkyl aminocarbonylamino, heteroaryl-($C_{1-6}$)alkyl aminocarbonylamino, ($C_{3-12}$)heterocycloalkyl-($C_{1-6}$)alkoxycarbonylamino, heteroaryl-($C_{1-6}$) alkoxycarbonylamino, ($C_{1-6}$)alkyl carbonylamino, ((($C_{1-6}$) alkyl carbonyl)($C_{1-6}$)alkyl)amino, $R_9R_{10}N$—($C_{1-6}$)alkyl carbonylamino, [$R_9R_{10}N$—($C_{1-6}$)alkylcarbonyl][($C_{1-6}$) alkyl]amino, $R_9R_{10}N$—($C_{1-6}$)alkyl sulfonylamino, [$R_9R_{10}N$—($C_{1-6}$)alkylsulfonyl][($C_{1-6}$)alkyl]amino, and —$R_9R_{10}$ where $R_9$ and $R_{10}$ are independently selected from the group consisting of hydrogen, ($C_{1-6}$)alkyl, heterocycloalkyl, and heteroaryl, each substituted or unsubstituted, or where $R_9$ and $R_{10}$ together are —($CH_2$)$_{4-5}$— optionally interrupted by one O, S, NH or —$N(C_{1-3}$)alkyl group, or where $R_9$ and $R_{10}$ together is selected from the group consisting of pyrrolidin-1-yl, morpholin-4-yl, and 4-methyl-piperazin-1-yl, each unsubstituted or substituted.

In a further variation, $R_{15}$ is selected from the group consisting of amino, —$SO_2Me$, —$SO_2NH_2$, —$SO_2NHMe$, —$SO_2NHCH_2CH_2OH$, —$SO_2NMe_2$, —$NHSO_2$(3-fluorophenyl), aminosulfonyl, alkylsulfonyl, arylsulfonyl, heteroarylsulfonyl, HS—, ($C_{1-6}$)alkylS-, carboxamide, imino group, $R_9R_{10}N$—($C_{1-6}$)alkylsulfonyl, —$NH_2$, —$NHCH_3$, —$N(CH_3)_2$, —$NH(C_{1-3}$)alkyl, —$N(C_{1-3}$-alkyl)$_2$, $R_9R_{10}N$—($C_{1-12}$)alkyl aminocarbonylamino, $R_9R_{10}N$—($C_{1-6}$)alkyl alkoxycarbonylamino, heterocycloalkyl-($C_{1-6}$)alkyl aminocarbonylamino, heteroaryl-($C_{1-6}$)alkyl aminocarbonylamino, ($C_{3-12}$)heterocycloalkyl-($C_{1-6}$)alkoxycarbonylamino, heteroaryl-($C_{1-6}$)alkoxycarbonylamino, ($C_{1-6}$)alkyl carbonylamino, ((($C_{1-6}$)alkyl carbonyl)($C_{1-6}$)alkyl)amino, $R_9R_{10}N$—($C_{1-6}$)alkyl carbonylamino, [$R_9R_{10}N$—($C_{1-6}$) alkylcarbonyl][($C_{1-6}$)alkyl]amino, $R_9R_{10}N$—($C_{1-6}$)alkyl sulfonylamino, [$R_9R_{10}N$—($C_{1-6}$)alkylsulfonyl][($C_{1-6}$)alkyl] amino, and —$R_9R_{10}$ where $R_9$ and $R_{10}$ are independently selected from the group consisting of hydrogen, ($C_{1-6}$)alkyl, heterocycloalkyl, and heteroaryl, each substituted or unsubstituted, or where $R_9$ and $R_{10}$ together are —($CH_2$)$_{4-5}$-optionally interrupted by one O, S, NH or —$N(C_{1-3}$)alkyl group, or where $R_9$ and $R_{10}$ together is selected from the group consisting of pyrrolidin-1-yl, morpholin-4-yl, and 4-methyl-piperazin-1-yl, each unsubstituted or substituted.

In another variation, $R_{15}$ is selected from the group consisting of hydrogen, F, Br, Cl, —$OCH_3$, —$SO_2Me$, —$SO_2NH_2$, —$SO_2NHMe$, —$SO_2NHCH_2CH_2OH$, —$SO_2NMe_2$, —$NHSO_2$(3-fluorophenyl), perhalo($C_{1-10}$) alkyl, —$OCF_3$, —$CF_3$, ($C_{1-10}$)alkyl, hydroxy-($C_{1-10}$)alkyl, aryl, aryl-($C_{1-10}$)alkyl, heteroaryl, aminosulfonyl, alkylsulfonyl, arylsulfonyl, heteroarylsulfonyl, hydroxy, aryloxy, heteroaryloxy, arylalkyl, heteroaryl($C_{1-10}$)alkyl, cycloalkyl, heterocycloalkyl, HS—, ($C_{1-6}$)alkylS-, cyano, nitro, cycloalkoxy, ($C_{1-12}$)alkoxy, —COOH, —$CO_2Me$, carboxamide, ($C_{1-12}$)alkylNHCO—, $R_9R_{10}N$—($C_{1-12}$)alkyl aminocarbonyl, $R_9R_{10}N$—($C_{1-6}$)alkoxycarbonyl, hetero-($C_{1-6}$) alkylaminocarbonyl, heterocycloalkyl-($C_{1-6}$)alkylCO—, heteroaryl-($C_{1-6}$)alkylCO—, heterocycloalkyl-($C_{1-6}$)alkylOCO—, heteroaryl-($C_{1-6}$)alkylOCO—, ($C_{1-6}$)alkylOCO—, diethoxyphosphorylmethyl, imino group, $R_9R_{10}N$—($C_{1-6}$) alkylsulfonyl, —$NH_2$, —$NHCH_3$, —$N(CH_3)_2$, —$NH(C_{1-3}$ alkyl, —$N(C_{1-3}$-alkyl)$_2$, $R_9R_{10}N$—($C_{1-12}$)alkyl aminocarbonylamino, $R_9R_{10}N$—($C_{1-6}$)alkyl alkoxycarbonylamino, heterocycloalkyl-($C_{1-6}$)alkyl aminocarbonylamino, heteroaryl-($C_{1-6}$)alkyl aminocarbonylamino, ($C_{3-12}$)heterocycloalkyl-($C_{1-6}$)alkoxycarbonylamino, heteroaryl-($C_{1-6}$) alkoxycarbonylamino, ($C_{1-6}$)alkyl carbonylamino, ((($C_{1-6}$) alkyl carbonyl)($C_{1-6}$)alkyl)amino, $R_9R_{10}N$—($C_{1-6}$)alkyl carbonylamino, [$R_9R_{10}N$—($C_{1-6}$)alkylcarbonyl][($C_{1-6}$) alkyl]amino, $R_9R_{10}N$—($C_{1-6}$)alkyl sulfonylamino, [$R_9R_{10}N$—($C_{1-6}$)alkylsulfonyl][($C_{1-6}$)alkyl]amino, and —$NR_9R_{10}$ where $R_9$ and $R_{10}$ are independently selected from the group consisting of hydrogen, ($C_{1-6}$)alkyl, heterocycloalkyl, and heteroaryl, each substituted or unsubstituted, or where $R_9$ and $R_{10}$ together are —($CH_2$)$_{4-5}$— optionally interrupted by one O, S, NH or —$N(C_{1-3}$)alkyl group, or where $R_9$ and $R_{10}$ together is selected from the group consisting of pyrrolidin-1-yl, morpholin-4-yl, and 4-methyl-piperazin-1-yl, each unsubstituted or substituted.

In another variation, $R_{11}$, $R_{12}$, $R_{13}$ and $R_{14}$ are each independently selected from the group consisting of hydrogen, F, Br, Cl, —OCH$_3$, —SO$_2$Me, —SO$_2$NH$_2$, —SO$_2$NHMe, —SO$_2$NHCH$_2$CH$_2$OH, —SO$_2$NMe$_2$, —NHSO$_2$(3-fluorophenyl), perhalo(C$_{1-10}$)alkyl, —OCF$_3$, —CF$_3$, (C$_{1-10}$) alkyl, hydroxy-(C$_{1-10}$)alkyl, aryl, aryl-(C$_{1-10}$)alkyl, heteroaryl, aminosulfonyl, alkylsulfonyl, arylsulfonyl, heteroarylsulfonyl, hydroxy, aryloxy, heteroaryloxy, arylalkyl, heteroaryl(C$_{1-10}$)alkyl, cycloalkyl, heterocycloalkyl, HS—, (C$_{1-6}$)alkylS-, cyano, nitro, cycloalkoxy, (C$_{1-12}$) alkoxy, —COOH, —CO$_2$Me, carboxamide, (C$_{1-12}$)alkylNHCO—, $R_9R_{10}$N—(C$_{1-12}$)alkyl aminocarbonyl, $R_9R_{10}$N—(C$_{1-2}$)alkoxycarbonyl, hetero-(C$_{1-6}$)alkylaminocarbonyl, heterocycloalkyl-(C$_{1-6}$)alkylCO—, heteroaryl-(C$_{1-6}$)alkylCO—, heterocycloalkyl-(C$_{1-6}$)alkylOCO—, heteroaryl-(C$_{1-6}$)alkylOCO—, (C$_{1-6}$)alkylOCO—, diethoxyphosphorylmethyl, imino group, $R_9R_{10}$N—(C$_{1-6}$)alkylsulfonyl, —NH$_2$, —NHCH$_3$, —N(CH$_3$)$_2$, —NH(C$_{1-3}$)alkyl, —N(C$_{1-3}$-alkyl)$_2$, $R_9R_{10}$N—(C$_{1-12}$)alkyl aminocarbonylamino, $R_9R_{10}$N—(C$_{1-6}$)alkyl alkoxycarbonylamino, heterocycloalkyl-(C$_{1-6}$)alkyl aminocarbonyl amino, heteroaryl-(C$_{1-6}$)alkyl aminocarbonylamino, (C$_{3-12}$)heterocycloalkyl-(C$_{1-6}$) alkoxycarbonylamino, heteroaryl-(C$_{1-6}$)alkoxycarbonylamino, (C$_{1-6}$)alkyl carbonylamino, ((C$_{1-6}$)alkyl carbonyl)(C$_{1-6}$ alkyl)amino, $R_9R_{10}$N—(C$_{1-6}$)alkyl carbonylamino, [$R_9R_{10}$N—(C$_{1-6}$)alkylcarbonyl][(C$_{1-6}$) alkyl]amino, $R_9R_{10}$N—(C$_{1-6}$)alkyl sulfonylamino, [$R_9R_{10}$N—(C$_{1-6}$)alkylsulfonyl][(C$_{1-6}$)alkyl]amino, and —NR$_9$R$_{10}$ where R$_9$ and R$_{10}$ are independently selected from the group consisting of hydrogen, (C$_{1-6}$)alkyl, heterocycloalkyl, aryl and heteroaryl, each substituted or unsubstituted, or where R$_9$ and R$_{10}$ together are —(CH$_2$)$_{4-5}$-optionally interrupted by one O, S, NH or —N(C$_{1-3}$)alkyl group, or where R$_9$ and R$_{10}$ together is selected from the group consisting of pyrrolidin-1-yl, morpholin-4-yl, and 4-methyl-piperazin-1-yl, each unsubstituted or substituted.

In another variation, $R_{11}$ and $R_{12}$, or $R_{12}$ and $R_{13}$, or $R_{13}$ and $R_{14}$ are taken together to form a substituted or unsubstituted fused ring. It is noted that the fused ring may optionally be a substituted or unsubstituted 5 or 6 membered aryl or heteroaryl ring. The fused ring may also optionally be a fused allicyclic ring.

In another variation, $R_4$ and $R_5$ are each independently selected from the group consisting of hydrogen, amino, cyano, (C$_{1-6}$)alkyl, (C$_{1-6}$)alkoxy, hydroxy-(C$_{1-6}$)alkyl, (C$_{1-10}$)alkoxycarbonyl, aryl, heterocyclyl, heteroaryl, aminocarbonyl, (C$_{1-6}$)alkyl aminocarbonyl, halogen and hydroxy, each substituted or unsubstituted.

According to each of the above embodiments, $R_4$ may optionally be selected from the group consisting of 2-furanyl, 3-thienyl, Br, hydrogen, cyano, 4-acetamidophenyl, and phenyl.

Also according to each of the above embodiments, $R_3$ and $R_4$ may optionally be taken together to form a substituted or unsubstituted fused ring. Also according to each of the above embodiments, $R_3$ and $R_4$ may optionally be taken together to form a fused ring selected from the group consisting of —NH—CH=N—, —NH—N=N—, —S—CH=N—, and —CH=CH—CH=N—.

Also according to each of the above embodiments, $R_5$ may optionally be selected from the group consisting of hydrogen, amino, (C$_{1-6}$)alkyl, (C$_{1-6}$)alkenyl, and phenyl, each substituted or unsubstituted.

Also according to each of the above embodiments, $R_5$ may optionally be selected from the group consisting of methyl, 2-furanyl, 2-thienyl, CH=CH$_2$, hydrogen and phenyl.

Particular examples of compounds according to the present invention include, but are not limited to, a compound selected from the group consisting of:
4-Dimethylamino-N-[6-(2-hydroxy-1H-indol-3-yl)-pyridin-3-yl]-butyramide;
2-Dimethylamino-N-[6-(2-hydroxy-1H-indol-3-yl)-pyridin-3-yl]-acetamide;
3-(4-Phenethylamino-quinolin-2-yl)-1H-indol-2-ol;
3-(4-Piperidin-1-yl-quinolin-2-yl)-1H-indol-2-ol;
3-(4-Benzylamino-quinolin-2-yl)-1H-indol-2-ol;
3-Quinoxalin-2-yl-1H-indol-2-ol;
3-[4-(2-Diethylamino-ethylamino)-quinolin-2-yl]-1H-indol-2-ol;
5-(3-Fluoro-phenyl)-3-quinolin-2-yl-1H-indol-2-ol;
5-Biphenyl-4-yl-3-quinolin-2-yl-1H-indol-2-ol;
3-Quinolin-2-yl-5-p-tolyl-1H-indol-2-ol;
5-(4-Phenoxy-phenyl)-3-quinolin-2-yl-1H-indol-2-ol;
5-(4-Fluoro-phenyl)-3-quinolin-2-yl-1H-indol-2-ol;
5-(4-Methoxy-phenyl)-3-quinolin-2-yl-1H-indol-2-ol;
5-(4-Methanesulfonyl-phenyl)-3-quinolin-2-yl-1H-indol-2-ol;
4-(2-Hydroxy-3-quinolin-2-yl-1H-indol-5-yl)-benzonitrile;
3-Quinolin-2-yl-5-styryl-1H-indol-2-ol;
5-(4-Hydroxymethyl-phenyl)-3-quinolin-2-yl-1H-indol-2-ol;
5-(4-Hydroxy-phenyl)-3-quinolin-2-yl-1H-indol-2-ol;
5-[2-(4-Fluoro-phenyl)-vinyl]-3-quinolin-2-yl-1H-indol-2-ol;
5-(3-Amino-phenyl)-3-quinolin-2-yl-1H-indol-2-ol;
5-Furan-3-yl-3-quinolin-2-yl-1H-indol-2-ol;
5-(2-Fluoro-phenyl)-3-quinolin-2-yl-1H-indol-2-ol;
5-(2-Methoxy-phenyl)-3-quinolin-2-yl-1H-indol-2-ol;
3-Quinolin-2-yl-5-(2-trifluoromethyl-phenyl)-1H-indol-2-ol;
5-(2-Hydroxy-phenyl)-3-quinolin-2-yl-1H-indol-2-ol;
6-(2-Fluoro-phenyl)-3-quinolin-2-yl-1H-indol-2-ol;
6-(3-Amino-phenyl)-3-quinolin-2-yl-1H-indol-2-ol;
5-(2-Chloro-phenyl)-3-quinolin-2-yl-1H-indol-2-ol;
6-(4-Fluoro-phenyl)-3-quinolin-2-yl-1H-indol-2-ol;
6-Phenyl-3-quinolin-2-yl-1H-indol-2-ol;
6-(3-Methanesulfonyl-phenyl)-3-quinolin-2-yl-1H-indol-2-ol;
3-(4-Phenylamino-quinolin-2-yl)-1H-indol-2-ol;
3-[4-(2-piperazin-1-yl-ethylamino)-quinolin-2-yl]-1H-indol-2-ol;
N-[3-(2-Hydroxy-3-quinolin-2-yl-1H-indol-5-yl)-phenyl]-methanesulfonamide;
N-[4-(2-Hydroxy-3-quinolin-2-yl-1H-indol-5-yl)-phenyl]-acetamide;
3-(4-Methylamino-quinolin-2-yl)-1H-indol-2-ol;
3-(4-Ethylamino-quinolin-2-yl)-1H-indol-2-ol;
5-(2-Hydroxymethyl-phenyl)-3-quinolin-2-yl-1H-indol-2-ol;
3-(4-Diethylamino-quinolin-2-yl)-1H-indol-2-ol;
5-(4-Amino-phenyl)-3-quinolin-2-yl-1H-indol-2-ol;
[4-(2-Hydroxy-3-quinolin-2-yl-1H-indol-5-yl)-phenyl]-carbamic acid benzyl ester;
3-(4-Isopropylamino-quinolin-2-yl)-1H-indol-2-ol;
5-(3-Ethoxy-phenyl)-3-quinolin-2-yl-1H-indol-2-ol;
3-(4-Cyclohexylamino-quinolin-2-yl)-1H-indol-2-ol;
5-(3-Ethanesulfonyl-phenyl)-3-quinolin-2-yl-1H-indol-2-ol;
1-Benzenesulfonyl-3'-quinolin-2-yl-1H, 1'H-[3,5']biindolyl-2'-ol;

3-(4-Cyclopentylamino-quinolin-2-yl)-1H-indol-2-ol;
3-(4-Dimethylamino-quinolin-2-yl)-1H-indol-2-ol;
3-Amino-5-(2-hydroxy-3-quinolin-2-yl-1H-indol-5-yl)-benzoic acid;
5-(1H-Pyrrol-2-yl)-3-quinolin-2-yl-1H-indol-2-ol;
3'-Quinolin-2-yl-1H, 1'H-[2,5']biindolyl-2'-ol;
5-Amino-3-quinolin-2-yl-1H-indol-2-ol;
3-(4-tert-Butylamino-quinolin-2-yl)-1H-indol-2-ol;
3-[4-(Methyl-phenyl-amino)-quinolin-2-yl]-1H-indol-2-ol;
3-(4-Morpholin-4-yl-quinolin-2-yl)-1H-indol-2-ol;
3-[4-(4-Methyl-piperazin-1-yl)-quinolin-2-yl]-1H-indol-2-ol;
3-[4-(Biphenyl-4-ylamino)-quinolin-2-yl]-1H-indol-2-ol;
3-{4-[2-(4-Hydroxy-phenyl)-ethylamino]-quinolin-2-yl}-1H-indol-2-ol;
3-[4-(3-Morpholin-4-yl-propylamino)-quinolin-2-yl]-1H-indol-2-ol;
3-[4-(4-Phenoxy-phenylamino)-quinolin-2-yl]1H-indol-2-ol;
3-[4-(Methyl-pyridin-3-yl-amino)-quinolin-2-yl]-1H-indol-2-ol;
3-[4-(Methyl-pyridin-4-yl-amino)-quinolin-2-yl]-1H-indol-2-ol;
3-[4-(3-Fluoro-phenylamino)-quinolin-2-yl]-1H-indol-2-ol;
5-Bromo-3-(5-chloro-quinolin-2-yl)-1H-indol-2-ol;
3-[4-(Pyridin-3-ylamino)-quinolin-2-yl]-1H-indol-2-ol;
3-[4-(2-Morpholin-4-yl-ethylamino)-quinolin-2-yl]-1H-indol-2-ol;
3-[5-(2-Hydroxy-phenylamino)-quinolin-2-yl]-1H-indol-2-ol;
8-Quinolin-2-yl-6H-thiazolo[5,4-e]indol-7-ol;
3-(4-Phenylsulfanyl-quinolin-2-yl)-1H-indol-2-ol;
N-{4-[2-(2-Hydroxy-1H-indol-3-yl)-quinolin-4-ylsulfanyl]-phenyl}-acetamide;
5-Pyridin-4-yl-3-quinolin-2-yl-1H-indol-2-ol;
5-(3-Aminomethyl-phenyl)-3-quinolin-2-yl-1H-indol-2-ol;
5-(3-Hydroxymethyl-phenyl)-3-quinolin-2-yl-1H-indol-2-ol;
5-(4-Aminomethyl-phenyl)-3-quinolin-2-yl-1H-indol-2-ol;
3-(4-Phenoxy-quinolin-2-yl)-1H-indol-2-ol;
1-(4-Fluoro-3-nitro-phenyl)-3-[2-(2-hydroxy-1H-indol-3-yl)-quinolin-5-yl]-urea;
3-(4-Amino-quinolin-2-yl)-1H-indol-2-ol;
3-(4-Ethylsulfanyl-quinolin-2-yl)-1H-indol-2-ol;
1-[2-Hydroxy-3-(8-hydroxy-quinolin-2-yl)-indol-1-yl]-ethanone;
3-[4-(4-Amino-phenylamino)-quinolin-2-yl]-1H-indol-2-ol;
N-{4-[2-(2-Hydroxy-1H-indol-3-yl)-quinolin-4-ylamino]-phenyl}-acetamide;
3-[4-(6-Amino-pyridin-3-ylamino)-quinolin-2-yl]-1H-indol-2-ol;
N-{4-[3-(4-Chloro-quinolin-2-yl)-2-hydroxy-1H-indol-5-yl]-phenyl}-acetamide;
2,N-Dihydroxy-3-quinolin-2-yl-1H-indole-5-carboxamidine;
2-Hydroxy-3-quinolin-2-yl-1H-indole-5-carboxamidine;
N-{4-[3-(3-Methyl-quinolin-2-yl)-2-oxo-2,3-dihydro-1H-indol-5-yl]-phenyl}-acetamide;
Ethanesulfonic acid (2-hydroxy-3-quinolin-2-yl-1H-indol-5-yl)-amide;
Ethanesulfonic acid [3-(4-chloro-quinolin-2-yl)-2-hydroxy-1H-indol-5-yl]-amide;
2-Hydroxy-3-quinolin-2-yl-1H-indole-5-carboximidic acid ethyl ester;
N-(2-Dimethylamino-ethyl)-2-hydroxy-3-quinolin-2-yl-1H-indole-5-carboxamidine;
2-Hydroxy-3-(4-phenylamino-quinolin-2-yl)-1H-indole-5-carbonitrile;
3-[4-(4-Amino-phenylamino)-quinolin-2-yl]-2-hydroxy-1H-indole-5-carbonitrile;
2-Hydroxy-3-{4-[(pyridin-2-ylmethyl)-amino]-quinolin-2-yl}-1H-indole-5-carbonitrile;
2-Hydroxy-3-{4-[(pyridin-3-ylmethyl)-amino]-quinolin-2-yl}-1H-indole-5-carbonitrile;
2-Hydroxy-3-{4-[(pyridin-4-ylmethyl)-amino]-quinolin-2-yl}-1H-indole-5-carbonitrile;
N-(3-Dimethylamino-propyl)-2-hydroxy-3-quinolin-2-yl-1H-indole-5-carboxamidine;
3-[4-(6-Amino-pyridin-3-ylamino)-quinolin-2-yl]-2-hydroxy-1H-indole-5-carbonitrile;
3-[4-(6-Amino-pyridin-3-ylamino)-quinolin-2-yl]-5-nitro-1H-indol-2-ol;
Ethanesulfonic acid {3-[4-(4-amino-phenylamino)-quinolin-2-yl]-2-hydroxy-1H-indol-5-yl}-amide;
N-{4-[3-(3-Methyl-quinolin-2-yl)-2-oxo-2,3-dihydro-1H-indol-5-yl]-phenyl}-methanesulfonamide;
N-{3-[3-(3-Methyl-quinolin-2-yl)-2-oxo-2,3-dihydro-1H-indol-5-yl]-phenyl}-methanesulfonamide;
Ethanesulfonic acid (2-hydroxy-3-{4-[(pyridin-2-ylmethyl)-amino]-quinolin-2-yl}-1H-indol-5-yl)-amide;
2-Hydroxy-N-methyl-3-quinolin-2-yl-1H-indole-5-carboxamidine;
N-Hydroxy-3-(3-methyl-quinolin-2-yl)-2-oxo-2,3-dihydro-1H-indole-5-carboxamidine;
N-{4-[2-(5-Cyano-2-hydroxy-1H-indol-3-yl)-quinolin-4-ylsulfanyl]-phenyl}-acetamide;
N-{4-[2-(5-Cyano-2-hydroxy-1H-indol-3-yl)-quinolin-4-ylamino]-phenyl}-acetamide;
Ethanesulfonic acid (2-hydroxy-3-{4-[(pyridin-3-ylmethyl)-amino]-quinolin-2-yl}-1H-indol-5-yl)-amide;
Ethanesulfonic acid (2-hydroxy-3-{4-[(pyridin-4-ylmethyl)-amino]-quinolin-2-yl}-1H-indol-5-yl)-amide;
2-Hydroxy-N-(2-morpholin-4-yl-ethyl)-3-quinolin-2-yl-1H-indole-5-carboxamidine;
2-Hydroxy-N-(3-morpholin-4-yl-propyl)-3-quinolin-2-yl-1H-indole-5-carboxamidine;
2-Hydroxy-3-quinolin-2-yl-N-(2-thiomorpholin-4-yl-ethyl)-1H-indole-5-carboxamidine;
2-Hydroxy-N-(2-piperidin-1-yl-ethyl)-3-quinolin-2-yl-1H-indole-5-carboxamidine;
2-Hydroxy-N-[3-(4-methyl-piperazin-1-yl)-propyl]-3-quinolin-2-yl-1H-indole-5-carboxamidine;
2-Hydroxy-N-pyridin-4-ylmethyl-3-quinolin-2-yl-1H-indole-5-carboxamidine;
2-Hydroxy-3-quinolin-2-yl-1H-indole-5-sulfonic acid ethylamide;
2-Hydroxy-3-quinolin-2-yl-1H-indole-5-sulfonic acid pyridin-3-ylamide;
2,N-Dihydroxy-3-{4-[(pyridin-3-ylmethyl)-amino]-quinolin-2-yl}-1H-indole-5-carboxamidine;
3-[4-(4-Amino-phenylamino)-quinolin-2-yl]-2,N-dihydroxy-1H-indole-5-carboxamidine;
2,N-Dihydroxy-3-{4-[(pyridin-2-ylmethyl)-amino]-quinolin-2-yl}-1H-indole-5-carboxamidine;
2,N-Dihydroxy-3-{4-[(pyridin-4-ylmethyl)-amino]-quinolin-2-yl}-1H-indole-5-carboxamidine;
3-[4-(6-Amino-pyridin-3-ylamino)-quinolin-2-yl]-2,N-dihydroxy-1H-indole-5-carboxamidine;
3-[6-(2-Diethylamino-ethoxy)-quinolin-2-yl]-2,N-dihydroxy-1H-indole-5-carboxamidine;
2,N-Dihydroxy-3-[6-(2-morpholin-4-yl-ethoxy)-quinolin-2-yl]-1H-indole-5-carboxamidine;

N-(2-Hydroxy-3-quinolin-2-yl-1H-indol-5-yl)-benzene-sulfonamide;
N-(2-Hydroxy-3-quinolin-2-yl-1H-indol-5-yl)-3-nitro-benzenesulfonamide;
N-(2-Hydroxy-3-quinolin-2-yl-1H-indol-5-yl)-4-nitro-benzenesulfonamide;
Naphthalene-1-sulfonic acid (2-hydroxy-3-quinolin-2-yl-1H-indol-5-yl)-amide;
N-(2-Hydroxy-3-quinolin-2-yl-1H-indol-5-yl)-3-methoxy-benzenesulfonamide;
Naphthalene-2-sulfonic acid (2-hydroxy-3-quinolin-2-yl-1H-indol-5-yl)-amide;
2,3-Dihydro-benzo[1,4]dioxine-6-sulfonic acid (2-hydroxy-3-quinolin-2-yl-1H-indol-5-yl)-amide;
Thiophene-2-sulfonic acid (2-hydroxy-3-quinolin-2-yl-1H-indol-5-yl)-amide;
N-(2-Hydroxy-3-quinolin-2-yl-1H-indol-5-yl)-3-methyl-benzenesulfonamide;
N-[3-(4-Chloro-quinolin-2-yl)-2-hydroxy-1H-indol-5-yl]-benzenesulfonamide;
N-[3-(4-Chloro-quinolin-2-yl)-2-hydroxy-1H-indol-5-yl]-3-nitro-benzenesulfonamide;
N-[3-(4-Chloro-quinolin-2-yl)-2-hydroxy-1H-indol-5-yl]-4-nitro-benzenesulfonamide;
Naphthalene-1-sulfonic acid [3-(4-chloro-quinolin-2-yl)-2-hydroxy-1H-indol-5-yl]-amide;
N-[3-(4-Chloro-quinolin-2-yl)-2-hydroxy-1H-indol-5-yl]-3-methoxy-benzenesulfonamide;
Naphthalene-2-sulfonic acid [3-(4-chloro-quinolin-2-yl)-2-hydroxy-1H-indol-5-yl]-amide;
2,3-Dihydro-benzo[1,4]dioxine-6-sulfonic acid [3-(4-chloro-quinolin-2-yl)-2-hydroxy-1H-indol-5-yl]-amide;
N-[3-(4-Chloro-quinolin-2-yl)-2-hydroxy-1H-indol-5-yl]-3-methyl-benzenesulfonamide;
C—(3-Chloro-phenyl)-N-[3-(4-chloro-quinolin-2-yl)-2-hydroxy-1H-indol-5-yl]-methanesulfonamide;
3-Chloro-N-[3-(4-chloro-quinolin-2-yl)-2-hydroxy-1H-indol-5-yl]-benzenesulfonamide;
3-Chloro-N-(2-hydroxy-3-quinolin-2-yl-1H-indol-5-yl)-benzenesulfonamide;
C—(3-Chloro-phenyl)-N-(2-hydroxy-3-quinolin-2-yl-1H-indol-5-yl)-methanesulfonamide;
3-Amino-N-(2-hydroxy-3-quinolin-2-yl-1H-indol-5-yl)-benzenesulfonamide;
4-Amino-N-(2-hydroxy-3-quinolin-2-yl-1H-indol-5-yl)-benzenesulfonamide;
N-[3-(4-Chloro-quinolin-2-yl)-2-hydroxy-1H-indol-5-yl]-C-phenyl-methanesulfonamide;
2-Hydroxy-3-quinolin-2-yl-1H-indole-5-sulfonic acid hydroxyamide;
2,N-Dihydroxy-3-quinolin-2-yl-1H-indole-5-carboxamidine-O-acetyl;
3-(4-Hydroxyamino-quinolin-2-yl)-1H-indol-2-ol;
2-Hydroxy-3-phenanthridin-6-yl-1H-indole-5-sulfonic acid ethylamide;
3-[6-(2-Diethylamino-ethoxy)-quinolin-2-yl]-2-hydroxy-1H-indole-5-sulfonic acid ethylamide;
2,N-Dihydroxy-3-(4-phenylamino-quinolin-2-yl)-1H-indole-5-carboxamidine;
N-[5-(2-Hydroxy-3-quinolin-2-yl-1H-indole-5-sulfonylamino)-pyridin-2-yl]-acetamide;
3-[6-(2-Diethylamino-ethoxy)-quinolin-2-yl]-2-hydroxy-1H-indole-5-sulfonic acid methylamide;
3-[6-(2-Dimethylamino-ethoxy)-quinolin-2-yl]-2-hydroxy-1H-indole-5-sulfonic acid methylamide;
3-[6-(2-Dimethylamino-ethoxy)-quinolin-2-yl]-2-hydroxy-1H-indole-5-sulfonic acid ethylamide;
3-[6-(2-Dimethylamino-ethoxy)-quinolin-2-yl]-2,N-dihydroxy-1H-indole-5-carboxamidine; and
2-(2-Methoxy-1H-indol-3-yl)-quinoline.

It is noted that the compounds of the present invention may be in the form of a pharmaceutically acceptable salt, biohydrolyzable ester, biohydrolyzable amide, biohydrolyzable carbamate, solvate, hydrate or a prodrug thereof (e.g., where the compound comprises a substituent that is convertible in vivo to a different substituent such as hydrogen).

It is further noted that the compounds of the present invention may optionally be solely or predominantly in the enol tautomer in its active state.

It is also noted that the compounds of the present invention may be present as a mixture of stereoisomers or may be present as a single stereoisomer.

A pharmaceutical composition comprising, as an active ingredient, a compound according to any one of the above embodiments and variations. In one variation, the composition is a solid formulation adapted for oral administration. In another variation, the composition is a liquid formulation adapted for oral administration. In yet another variation, the composition is a tablet. In still another variation, the composition is a liquid formulation adapted for parenteral administration.

In one aspect of the present invention, there is provided a pharmaceutical composition comprising a compound according to any one of the above compounds, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In another aspect, there is provided a kit comprising any one or more of the above compounds and instructions which comprise one or more forms of information selected from the group consisting of indicating a disease state for which the compound is to be administered, storage information for the compound, dosing information and instructions regarding how to administer the compound. In one aspect, the kit comprises the compound in a multiple dose form.

In yet another aspect, there is provided an article of manufacture comprising any one or more of the above compounds and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the composition. In another variation, the article of manufacture comprises the compound in a multiple dose form.

In still another aspect, there is provided a method of inhibiting kinase comprising contacting a kinase with any one or more of the above compounds. In one variation, the inhibition arises from a favorable conformation adopted by the compound in its enol form, and the conformation arises from intramolecular hydrogen bonding of the enol hydrogen and an adjacent nitrogen atom of the compound. In another variation, the inhibition arises from a favorable conformation adopted by the compound in its enol form, and the inhibition arises from a hydrogen bonding interaction between the enol tautomer and an active site residue of the kinase.

In a further aspect, there is provided a method of inhibiting kinase comprising causing any one or more of the above compounds to be present in a subject in order to inhibit kinase in vivo.

In another aspect, there is provided a method of inhibiting kinase comprising administering a first compound to a subject that is converted in vivo to a second compound wherein the second compound inhibits kinase in vivo, the second compound being a compound according to any of the above compounds.

In yet another aspect, there is provided a therapeutic method comprising administering any one or more of the above compounds to a subject.

In still another aspect, there is provided a method of treating a disease state for which kinase possesses activity that contributes to the pathology and/or symptomology of the disease state, wherein any one or more of the above compounds are caused to be present in a subject in a therapeutically effective amount for the disease state.

In a further aspect, there is provided a method of treating a disease state for which kinase possesses activity that contributes to the pathology and/or symptomology of the disease state, comprising administering a first compound to a subject that is converted in vivo to a second compound according to any one of the above compounds, wherein the second compound is present in a subject in a therapeutically effective amount for the disease state.

In another aspect, there is provided a method of treating a disease state for which kinase possesses activity that contributes to the pathology and/or symptomology of the disease state, comprising administering any one or more of the above compounds to a subject, wherein the one or more compounds are present in the subject in a therapeutically effective amount for the disease state.

In yet another aspect, there is provided a method for treating cancer comprising administration to a mammalian species in need thereof of a therapeutically effective amount of any one or more of the above compounds. In one variation, the cancer is selected from the group consisting of squamous cell carcinoma, astrocytoma, Kaposi's sarcoma, glioblastoma, non small-cell lung cancer, bladder cancer, head and neck cancer, melanoma, ovarian cancer, prostate cancer, breast cancer, small-cell lung cancer, glioma, colorectal cancer, genitourinary cancer and gastrointestinal cancer.

In still another aspect, there is provided a method for treating inflammation, inflammatory bowel disease, psoriasis, or transplant rejection, comprising administration to a mammalian species in need thereof of a therapeutically effective amount of any one or more of the above compounds.

In a further aspect, there is provided a method for preventing or treating dementia related diseases and Alzheimer's Disease, comprising administration to a mammalian species in need thereof of a therapeutically effective amount of any one or more of the above compounds. In one variation, the dementia related diseases are selected from the group consisting of Frontotemporal dementia Parkinson's Type, Parkinson dementia complex of Guam, HIV dementia, diseases with associated neurofibrillar tangle pathologies, predemented states, vascular dementia, dementia with Lewy bodies, Frontotemporal dementia and dementia pugilistica.

In another aspect, there is provided a method for preventing or treating dementia related diseases, Alzheimer's Disease and conditions associated with kinases, comprising administering to a mammal, including man in need of such prevention and/or treatment, a therapeutically effective amount of any one or more of the above compounds.

In yet another aspect, there is provided a method for preventing or treating amyotrophic lateral sclerosis, corticobasal degeneration, Down syndrome, Huntington's Disease, Parkinson's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss and contraceptive medication, comprising administration to a mammalian species in need thereof of a therapeutically effective amount of any one or more of the above compounds.

In still another aspect, there is provided a method for preventing or treating mild Cognitive Impairment, Age-Associated Memory Impairment, Age-Related Cognitive Decline, Cognitive Impairment No Dementia, mild cognitive decline, mild neurocognitive decline, Late-Life Forgetfulness, memory impairment and cognitive impairment and androgenetic alopecia comprising administration to a mammalian species in need thereof of a therapeutically effective amount of any one or more of the above compounds.

In another aspect, there is provided a method for treating arthritis comprising administration to a mammalian species in need thereof of a therapeutically effective amount of any one or more of the above compounds.

Salts, Hydrates, and Prodrugs of Kinase Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as $(C_{1-4})$ alkyl halides, e.g., methyl, ethyl, iso-propyl and tert-butyl chlorides, bromides and iodides; di $(C_{1-4})$ alkyl sulfates, e.g., dimethyl, diethyl and diamyl sulfates; $(C_{10-18})$ alkyl halides, e.g., decyl, dodecyl, lauryl, myristyl and stearyl chlorides, bromides and iodides; and aryl $(C_{1-4})$ alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in T. W. Greene, *Protecting Groups in Organic Synthesis*, 3$^{rd}$ edition, John Wiley & Sons, Inc. 1999.

Compounds of the present invention may also be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Preparation of Kinase Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Composition Comprising Kinase Inhibitors

A wide variety of compositions and administration methods may be used in conjunction with the kinase inhibitors of the present invention. Such compositions may include, in addition to the kinase inhibitors of the present invention, conventional pharmaceutical excipients, and other conventional, pharmaceutically inactive agents. Additionally, the compositions may include active agents in addition to the kinase inhibitors of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising kinase inhibitors of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The kinase inhibitors and compositions comprising them may be administered or coadministered in any conventional dosage form. Co-administration in the context of this invention is intended to mean the administration of more than one therapeutic agent, one of which includes a kinase inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When kinase inhibitors according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding kinase inhibitors according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more kinase inhibitors according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of a kinase inhibitor of the present invention to reduce kinases activity in vivo, thereby treating the disease state of the subject.

Dosage forms or compositions may optionally comprise one or more kinase inhibitors according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more kinase inhibitors, optionally 0.1-95%, and optionally 1-95%.

Salts, preferably sodium salts, of the kinase inhibitors may be prepared with carriers that protect the compound against rapid elimination from the body, such as time release formulations or coatings. The formulations may further include other active compounds to obtain desired combinations of properties.

Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, kinase inhibitors according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The kinase inhibitors of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising kinase inhibitors of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic adds and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. Nos. Re 28,819 and 4,358,603.

Injectables, Solutions, and Emulsions

The present invention is also directed to compositions designed to administer the kinase inhibitors of the present invention by parenteral administration, generally characterized by injection, either subcutaneously, intramuscularly or intravenously. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions include EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of a kinase inhibitor in the parenteral formulation may be adjusted so that an injection administers a pharmaceutically effective amount sufficient to produce the desired pharmacological effect. The exact concentration of a kinase inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is know and practiced in the art.

Injectables may be designed for local and systemic administration. Typically a therapeutically effective dosage is formulated to contain a concentration of at least about 0.1% w/w up to about 90% w/w or more, preferably more than 1% w/w of the kinase inhibitor to the treated tissue(s). The kinase inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The kinase inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The kinase inhibitors of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a kinase inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the kinase inhibitor.

Topical Administration

The kinase inhibitors of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The kinase inhibitors may be formulated as aerosols for topical application, such as by inhalation (see, U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The kinase inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the kinase inhibitor alone or in combination with other pharmaceutically acceptable excipients can also be administered.

Formulations for Other Routes of Administrations

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Examples of Formulations

The following are particular examples of oral, intravenous and tablet formulations that may optionally be used with compounds of the present invention. It is noted that these formulations may be varied depending on the particular compound being used and the indication for which the formulation is going to be used.

Oral Formulation

| | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

Intravenous Formulation

| | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

Tablet Formulation

| | |
|---|---|
| Compound of the Present Invention | 1% |
| Microcrystalline Cellulose | 73% |
| Stearic Acid | 25% |
| Colloidal Silica | 1%. |

Kits Comprising Kinase Inhibitors

The invention is also directed to kits and other articles of manufacture for treating diseases associated with kinases. It is noted that diseases are intended to cover all conditions for which the kinases possesses activity that contributes to the pathology and/or symptomology of the condition.

In one embodiment, a kit is provided that comprises a composition comprising at least one kinase inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one kinase inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

Preparation of Kinase Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, *Protecting Groups in Organic Synthesis,* 3rd edition, John Wiley & Sons, Inc. 1999.

Compounds according to the present invention may be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or thee-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| g (grams); | mg (milligrams); |
| L (liters); | mL (milliliters); |
| µL (microliters); | psi (pounds per square inch); |
| M (molar); | mM (millimolar); |
| i.v. (intravenous); | Hz (Hertz); |
| MHz (megahertz); | mol (moles); |
| mmol (millimoles); | RT (ambient temperature); |
| min (minutes); | h (hours); |
| mp (melting point); | TLC (thin layer chromatography); |
| Tr (retention time); | RP (reverse phase); |
| MeOH (methanol); | i-PrOH (isopropanol); |
| TEA (triethylamine); | TFA (trifluoroacetic acid); |
| TFAA (trifluoroacetic anhydride); | THF (tetrahydrofuran); |
| DMSO (dimethylsulfoxide); | EtOAc (ethyl acetate); |
| DME (1,2-dimethoxyethane); | DCM (dichloromethane); |
| DCE (dichloroethane); | DMF (N,N-dimethylformamide); |
| DMPU (N,N'-dimethylpropyl-eneurea); | CDI (1,1-carbonyldiimidazole); |
| IBCF (isobutyl chloroformate); | HOAc (acetic acid); |
| HOSu (N-hydroxysuccinimide); | HOBT (1-hydroxybenzotriazole); |
| $Et_2O$ (diethyl ether); | EDCI (ethylcarbodiimide hydrochloride); |
| BOC (tert-butyloxycarbonyl); | FMOC (9-fluorenylmethoxy-carbonyl); |
| DCC (dicyclohexylcarbodiimide); | CBZ (benzyloxycarbonyl); |
| Ac (acetyl); | atm (atmosphere); |
| TMSE (2-(trimethylsilyl)ethyl); | TMS (trimethylsilyl); |
| TIPS (triisopropylsilyl); | TBS (t-butyldimethylsilyl); |
| DMAP (4-dimethylaminopyridine); | Me (methyl); |
| OMe (methoxy); | Et (ethyl); |
| Et (ethyl); | tBu (tert-butyl); |
| HPLC (high pressure liquid chromatography); | |
| BOP (bis(2-oxo-3-oxazolidinyl)phosphinic chloride); | |
| TBAF (tetra-n-butylammonium fluoride); | |
| mCPBA (meta-chloroperbenzoic acid. | |

All references to ether or $Et_2O$ are to diethyl ether; brine refers to a saturated aqueous solution of NaCl. Unless otherwise indicated, all temperatures are expressed in ° C. (degrees Centigrade). All reactions conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's *Reagents for Organic Synthesis*, vols. 1-17, John Wiley and Sons, New York, N.Y., 1991; Rodd's Chemistry of Carbon Compounds, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

The entire disclosure of all documents cited throughout this application are incorporated herein by reference.

Synthetic Schemes for Kinase Inhibitors of the Present Invention

Kinase inhibitors according to the present invention may be synthesized according to the reaction scheme shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Reaction Scheme

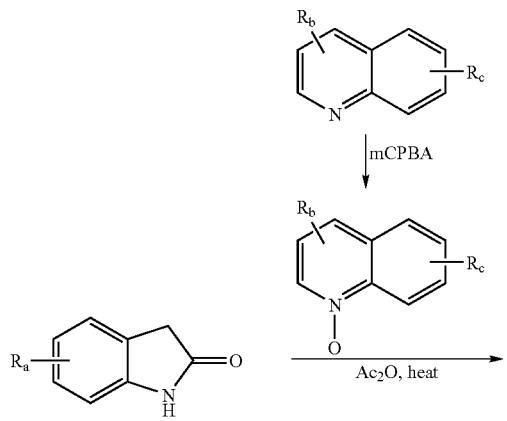

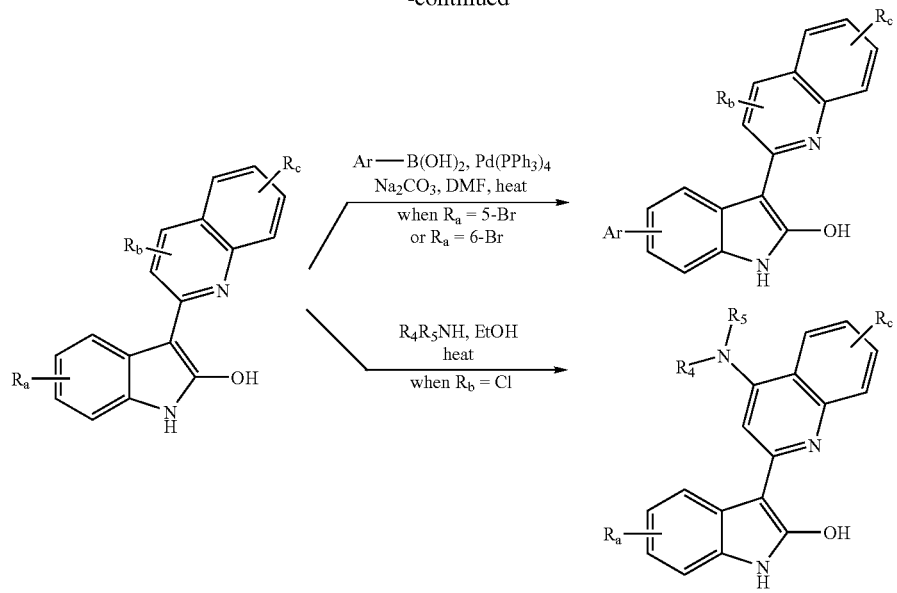

Procedure A:

Formation of Quinoline-N-oxides: The appropriate quinoline (10 mmol) may be dissolved in $CH_2Cl_2$ and treated with solid $NaHCO_3$ (50 mmol) followed by m-CPBA (10.0 mmol). The reaction may be stirred at between 0-40° C. for between 15 minutes to 6 hours. In one variation, the reaction is stirred at about 23° C. for 4 hours. The mixture may then be transferred to a separatory funnel and washed with water, saturated aqueous $NaHCO_3$ and brine, and then dried ($MgSO_4$) and concentrated in vacuo. The resulting crude solid is often pure enough to carry forward to the next reaction.

Condensation of oxindoles with quinoline-N-oxides: An oxindole (1.6 mmol) may be taken up in acetic anhydride (10 mL) and a solution of quinoline-N-oxide (0.474 mmol) and 5 mL of acetic anhydride may be added. This solution may then be heated at between 0-150° C. for between 1-25 hours. In one variation, the reaction is conducted at about 90° C. for about 3 hours. The resulting solution may then be cooled to room temperature. If a solid is observed upon cooling, the material may be isolated by filtration and washed with a minimal amount of cold MeOH, then dried in vacuo. If no solid is observed upon cooling, the reaction may be diluted with an organic solvent, such as ethyl acetate, washed with brine several times, dried over $MgSO_4$ and concentrated to afford an oil. Purification by preparative HPLC may afford a solid product.

Procedure B:

Suzuki Couplings: The bromide 17 (0.50 mmol), boronic acid (0.55 mmol) and $Pd(PPh_3)_4$ (0.025 g) may be taken up in dimethylformamide (5 mL), and 1M $Na_2CO_3$ (2.5 mL) added. This solution may then be heated at 20-120° C. overnight at which point the solution may be cooled to room temperature. In one variation, the reaction is conducted at 85° C. If a solid is observed upon cooling, the material may be collected by filtration and washed with water and a small amount of alcohol such as methanol. The product may then be further purified by preparative HPLC as necessary. If no solid is observed upon cooling, the solution may be diluted with water and then extracted with an organic solvent such as ethyl acetate. The organic layer may then be washed with brine, dried ($MgSO_4$) and concentrated in vacuo. Further purification may then be performed using preparative HPLC as necessary.

Procedure C:

Nucleophilic Aromatic Substitutions: A mixture of 3-(5-chloro-quinolin-2-yl)-1H-indol-2-ol (1.0 mmol) and a nucleophile (3.0 mmol) in EtOH (5.0 mL) may be heated at 50-250° C. for 1-20 minutes using a microwave reactor. In one variation, the reaction is heated at about 180° C. If a solid is observed upon cooling, the material may be isolated by filtration and washed with a minimal amount of cold MeOH, then dried in vacuo. If no solid is observed upon cooling, the reaction may be diluted with an organic solvent, such as ethyl acetate, washed with brine several times, dried over $MgSO_4$ and concentrated to afford an oil. Purification by preparative HPLC may afford the product as a solid. The resultant solid may then be filtered and dried to obtain pure compound.

In each of the above reaction procedures or scheme, the various substituents may be selected from among the various substituents otherwise taught herein.

Descriptions of the syntheses of particular compounds according to the present invention based on the above reaction scheme are set forth herein.

Biological Testing

The activity of compounds as protein kinase inhibitors may be assayed in vitro, in vivo or in a cell line. In vitro assays include assays that determine inhibition of either the phosphorylation activity or ATPase activity of the activated protein kinase. Alternate in vitro assays quantitate the ability of the inhibitor to bind to the protein kinase. Inhibitor binding may be measured by radiolabelling the inhibitor prior to binding, isolating the inhibitor/protein kinase complex and determining the amount of radiolabel bound. Alternatively, inhibitor binding may be determined by running a competition experiment where new inhibitors are incubated with the protein kinase bound to known radioligands.

Determination For the Inhibition of AIK

The inhibitory properties of compounds relative to AIK may be determined by the Direct Fluorescence Polarization detection method (FP) using a Greiner small volume black 384-well-plate format under the following reaction conditions: 50 mM Hepes pH 7.3, 10 mM $MgCl_2$, 10 mM NaCl, 1 mM DTT, 0.01% Brij35, 100 nM Fluorescein-LRRASLG peptide (provided by SYNPEP), 5% DMSO, 2.5 uM ATP. Detection of the reaction product is performed by addition of IMAP binding reagent (Molecular Devices). Reaction product may be determined quantitatively by FP using an Analyst HT plate reader (Molecular Devices) with an excitation wavelength at 485 nm and emission at 530 nm and using a Fluorescein 505 dichroic mirror.

The assay reaction may be initiated as follows: 2 ul of (3×) 300 nM FI-Peptide/7.5 uM ATP was added to each well of the plate, followed by the addition of 2 ul of (3×) inhibitor (2.5 fold serial dilutions for 11 data points for each inhibitor) containing 15% DMSO. 2 ul of (3×) 7.5 nM AIK solution may be added to initiate the reaction (final enzyme concentration was 2.5 nM for AIK). The reaction mixture may then be incubated at room temperature for 45 min, and quenched and developed by addition of 20 ul of 1 to 400 diluted IMAP binding reagent in 1× proprietary IMAP binding buffer. Fluorescence polarization readings of the resulting reaction mixtures may be measured after a 60-minute incubation at room temperature.

IC50 values may be calculated by non-linear curve fitting of the compound concentrations and fluorescent polarization values to the standard IC50 equation. As a reference point for this assay, Staurosporin showed an IC50 of <10 nM.

Determination for the Inhibition of c-KIT

The inhibitory properties of compounds relative to c-Kit may be determined by the Time-Resolved Fluorescence Resonance Energy Transfer (TR-FRET) method using a small volume black 384-well-plate (Greiner) format under the following reaction conditions: 50 mM Hepes pH 7.3, 10 mM MgCl2, 10 mM NaCl, 1 mM DTT, 0.01% Brij35, 250 nM Biotin-EGPWLEEEEEAYGWMDF peptide (provided by SYNPEP), 5% DMSO, 100 uM ATP. Detection of the reaction product may be performed by addition of Streptavidin-APC (Prozyme) and Eu-Anti-phosphotyrosine antibody (Perkin Elmer). Reaction product may be determined quantitatively by TR-FRET reading using an Analyst HT plate reader (Molecular Devices) with an excitation wavelength at 330 nm and emission at 615 nm (Europium) compared to 330 nm excitation (Europium) and emission 665 nm (APC) and using an Europium 400 dichroic mirror.

The assay reaction may be initiated as follows: 4 ul of (2.5×) 625 nM Biotin-Peptide/250 uM ATP was added to each well of the plate, followed by the addition of 2 ul of (5×) inhibitor (2.5 fold serial dilutions for 11 data points for each inhibitor) containing 25% DMSO. 4 ul of (2.5×) c-Kit solution may be added to initiate the reaction (final enzyme concentration was 0.13 nM for c-Kit). The reaction mixture may then be incubated at room temperature for 30 min, and quenched and developed by addition of 10 ul of (2×) 3.2 nM Eu-Antibody and 25 nM Streptavidin-APC in 50 mM Hepes pH 7.3, 30 mM EDTA, 0.1% Triton X-100 buffer. TR-FRET readings of the resulting reaction mixtures may be measured after a 60-minute incubation at room temperature on the Analyst HT.

IC50 values may be calculated by non-linear curve fitting of the compound concentrations and ratio metric Eu:APC values to the standard IC50 equation. As a reference point for this assay, Staurosporin showed an IC50 of <5 nM.

The following abbreviations have been used:
ATP Adenosine Triphosphate
BSA Bovine Serum Albumin
EDTA Ethylenediaminetetraacetic acid
MOPS Morpholinepropanesulfonic acid
SPA Scintillation Proximity Assay Provided herein are examples of kinase inhibitors that have been found to have IC50 values in the range of about 0.001 to about 100,000 nM. Other values for IC50 are in the range of about 0.001 to about 10,000 nM for AIK and/or c-KIT.

Examples of Kinase Inhibitors

The present invention is further exemplified, but not limited by, the following examples that describe the synthesis of particular compounds according to the invention.

The following compounds were prepared according to Procedure A:

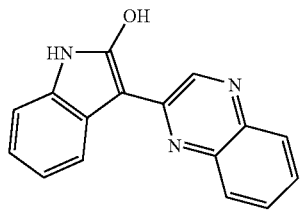

3-Quinoxalin-2-yl-1H-indol-2-ol: $^1$H NMR (400 MHz, DMSO-d6) δ 6.71-6.81 (m, 2H), 6.86 (m, 1H), 7.14 (m, 1H), 7.33-7.39 (m, 2H), 7.52-7.63 (m, 2H), 9.05 (s, 1H), 10.58 (s, 1H), 13.44 (s, 1H). ESI-MS: m/z 262.0 (M+H)$^+$.

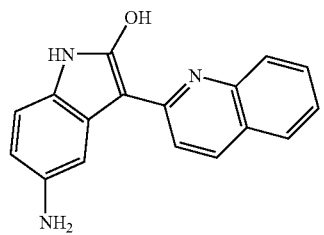

5-Amino-3-quinolin-2-yl-1H-indol-2-ol: $^1$H NMR (400 MHz, DMSO-d6): δ 6.88-7.01 (m, 2H), 7.38 (t, 1H), 7.53-7.75 (br m, 4H), 7.83 (d, 1H), 8.24 (d, 1H), 9.55 (br s, 2H), 10.75 (s, 1H), 14.45 (s, 1H). ESI-MS: m/z 276.8 (M+H)$^+$.

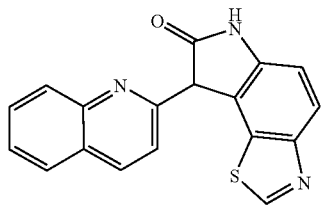

8-Quinolin-2-yl-6,8-dihydro-thiazolo[5,4-e]indol-7-one: $^1$H NMR (400 MHz, MeOH-d3): δ 7.28 (d, 1H), 7.44 (t, 1H), 7.68-7.78 (m, 2H), 7.83 (d, 1H), 7.88 (d, 1H), 8.18 (d, 1H), 8.33 (d, 1H), 9.25 (s, 1H), 11.10 (s, 1H), 15.15 (br s, 1H). ESI-MS: m/z 318.7 (M+H)$^+$.

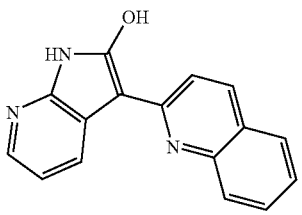

3-Quinolin-2-yl-7-aza-1H-indol-2-ol: $^1$H NMR (400 MHz, DMSO-d6) δ 6.95 (dd, J=7.58, 5.05 Hz, 1H), 7.28-7.41 (m, 1H), 7.56-7.69 (m, 2H), 7.75 (d, J=9.35 Hz, 1H), 7.82 (d, J=7.83 Hz, 1H), 7.89 (dd, J=5.05, 1.26 Hz, 1H), 7.94 (d, J=9.35 Hz, 1H), 8.13 (d, J=9.35 Hz, 1H), 11.08 (s, 1H), 14.20 (s, 1H). ESI-MS: m/z 262.0 (M+H)$^+$.

The following compounds were prepared according to Procedure B:

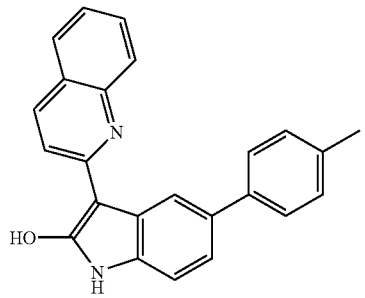

5-(4-Methyl-phenyl)-3-quinolin-2-yl-1H-indol-2-ol: $^1$H NMR (400 MHz, DMSO-d6): δ 2.35 (s, 3H), 6.89 (d, 1H), 7.22-7.37 (m, 3H), 7.55-7.68 (m, 3H), 7.82 (m, 1H), 7.90 (d, 1H), 8.09 (d, 1H), 10.65 (s, 1H), 14.45 (s, 1H). ESI-MS: m/z 351.9 (M+H)$^+$.

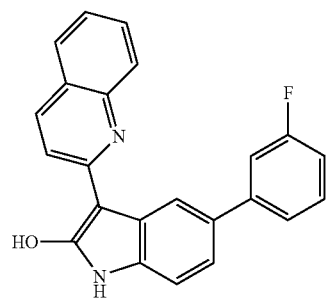

5-(3-Fluoro-phenyl)-3-quinolin-2-yl-1H-indol-2-ol: $^1$H NMR (400 MHz, DMSO-d6): δ 7.02 (d, 1H), 7.13 (t, 1H), 7.32 (m, 2H), 7.49 (q, 1H), 7.54-7.67 (m, 4H), 7.81 (d, 1H), 7.88 (s, 1H), 7.95 (d, 1H), 8.10 (d, 1H), 10.75 (s, 1H), 14.45 (s, 1H). ESI-MS: m/z 354.7 (M+H)$^+$.

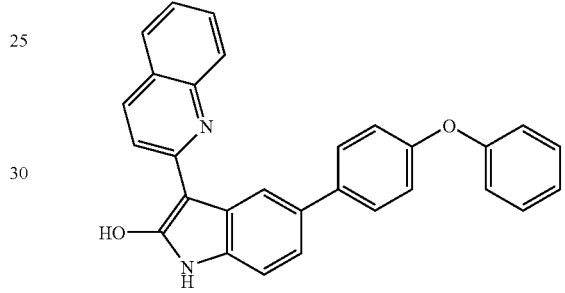

5-(4-Phenoxy-phenyl)-3-quinolin-2-yl-1H-indol-2-ol: $^1$H NMR (400 MHz, DMSO-d6): δ 7.01 (d, 1H), 7.02-7.11 (m, 4H), 7.16 (t, 1H), 7.25 (d, 1H), 7.33 (t, 1H), 7.38-7.46 (m, 2H), 7.57 (d, 1H), 7.62-7.67 (m, 1H), 7.72-7.76 (m, 2H), 7.78-7.84 (m, 2H), 7.90 (d, 1H), 8.09 (d, 1H), 10.65 (s, 1H), 14.45 (s, 1H). ESI-MS: m/z 429.8 (M+H)$^+$.

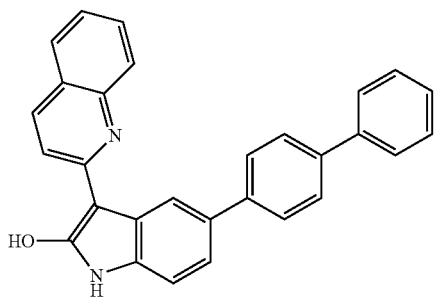

5-Biphenyl-4-yl-3-quinolin-2-yl-1H-indol-2-ol: $^1$H NMR (400 MHz, DMSO-d6): δ 7.04 (d, 1H), 7.29-7.42 (m, 3H), 7.43-7.55 (m, 2H), 7.55-7.68 (m, 2H), 7.69-7.87 (m, 9H), 7.92 (m, 1H), 8.12 (d, 1H), 10.75 (s, 1H), 14.45 (s, 1H). ESI-MS: m/z 412.8 (M+H)$^+$.

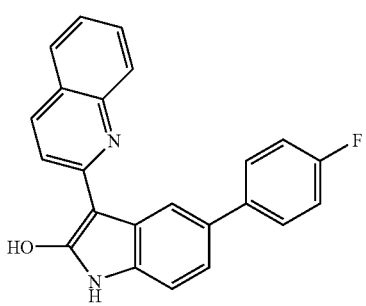

5-(4-Fluoro-phenyl)-3-quinolin-2-yl-1H-indol-2-ol: $^1$H NMR (400 MHz, DMSO-d6): δ 6.99 (d, 1H), 7.21-7.36 (m, 4H), 7.55-7.68 (m, 2H), 7.72-7.85 (m, 4H), 7.93 (d, 1H), 8.09 (d, 1H), 10.65 (s, 1H), 14.45 (s, 1H). ESI-MS: m/z 354.7 (M+H)$^+$.

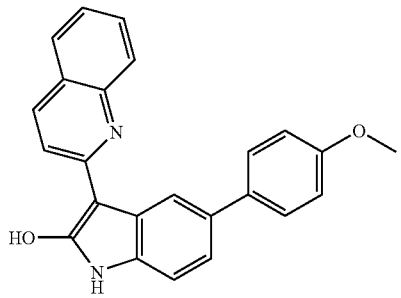

5-(4-Methoxy-phenyl)-3-quinolin-2-yl-1H-indol-2-ol: $^1$H NMR (400 MHz, DMSO-d6): δ 3.80 (s, 3H), 6.92-7.04 (m 3H), 7.21 (d, 1H), 7.32 (t, 1H), 7.52-7.67 (m, 4H), 7.73-7.80 (m, 2H), 7.89 (d, 1H), 8.08 (d, 1H), 10.65 (s, 1H), 14.45 (s, 1H). ESI-MS: m/z 366.7 (M+H)$^+$.

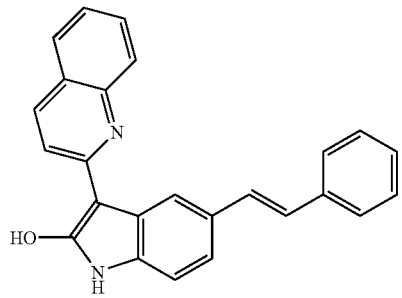

5-(2-Phenylvinyl)-3-quinolin-2-yl-1H-indol-2-ol: $^1$H NMR (400 MHz, DMSO-d6): δ 6.93 (d, 1H), 7.20-7.42 (br m, 7H), 7.52-7.68 (m, 4H), 7.88 (q, 1H), 7.88-7.97 (m, 2H), 8.13, (d, 1H), 10.70 (s, 1H), 14.45 (s, 1H). ESI-MS: m/z 362.8 (M+H)$^+$.

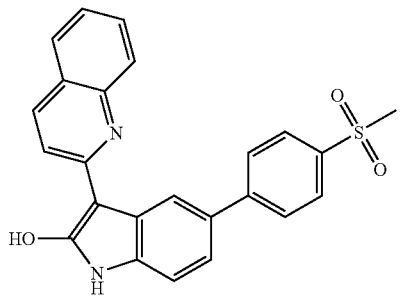

5-(4-Methanesulfonyl-phenyl)-3-quinolin-2-yl-1H-indol-2-ol: $^1$H NMR (400 MHz, DMSO-d6): δ 3.32 (s, 3H), 7.06 (d, 1H), 7.35 (m, 2H), 7.59-7.69 (m, 2H), 7.69-7.89 (m, 3H), 7.89-7.99 (m, 3H), 8.10-8.20 (m, 2H), 10.75 (s, 1H), 14.45 (s, 1H). ESI-MS: m/z 416.7 (M+H)$^+$.

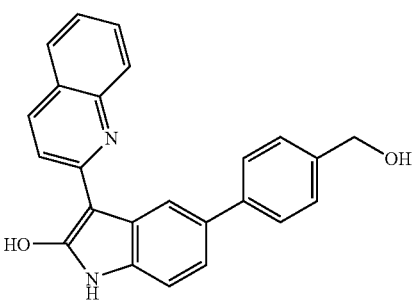

5-(4-Hydroxymethyl-phenyl)-3-quinolin-2-yl-1H-indol-2-ol: $^1$H NMR (400 MHz, DMSO-d6): δ 4.55 (s, 2H), 7.03 (d, 1H), 7.27 (d, 1H), 7.34 (t, 1H), 7.39 (d, 2H), 7.58 (d, 1H), 7.63 (d, 1H), 7.64-7.71 (m, 2H), 7.76-7.83 (m, 2H), 7.92 (d, 1H), 8.08 (d, 1H), 10.70 (s, 1H), 14.45 (s, 1H). ESI-MS: m/z 366.7 (M+H)$^+$.

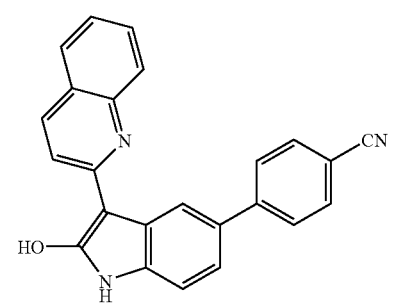

5-(4-Nitrile-phenyl)-3-quinolin-2-yl-1H-indol-2-ol: $^1$H NMR (400 MHz, DMSO-d6): δ 7.04 (d, 1H), 7.30-7.41 (m, 2H), 7.58-7.72 (m, 2H), 7.82 (d, 1H), 7.89-8.10 (m, 6H), 8.13 (d, 1H), 10.80 (s, 1H), 14.45 (s, 1H). ESI-MS: m/z 361.8 (M+H)$^+$.

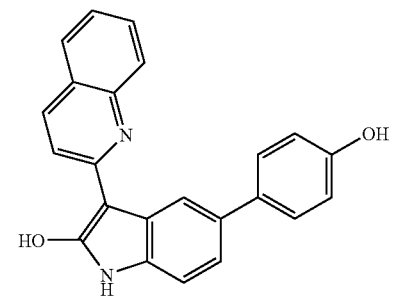

5-(4-Hydroxy-phenyl)-3-quinolin-2-yl-1H-indol-2-ol: $^1$H NMR (400 MHz, DMSO-d6): δ 6.84 (d, 2H), 6.95 (d, 1H), 7.18 (dd, 1H), 7.33 (t, 1H), 7.48-7.58 (m, 3H), 7.63 (dd, 1H), 7.74 (s, 1H), 7.78 (d, 1H), 7.88 (d, 1H), 8.07 (d, 1H), 9.40 (s, 1H), 10.60 (s, 1H), 14.45 (s, 1H). ESI-MS: m/z 353.7 (M+H)$^+$.

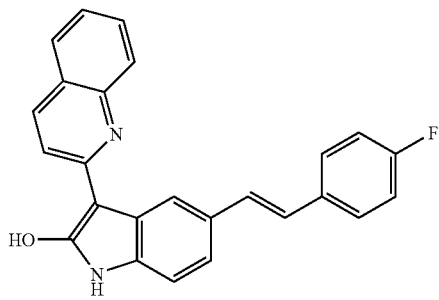

5-(2-(4-Fluorophenyl)-vinyl)-3-quinolin-2-yl-1H-indol-2-ol: ¹H NMR (400 MHz, DMSO-d6): δ 6.94 (d, 1H), 7.15-7.29 (m, 4H), 7.34 (t, 1H), 7.57 (d, 1H), 7.59-7.68 (m, 3H), 7.82 (d, 1H), 7.84-7.95 (m, 3H), 8.13 (d, 1H), 10.70 (s, 1H), 14.45 (s, 1H), ESI-MS: m/z 380.8 (M+H)⁺.

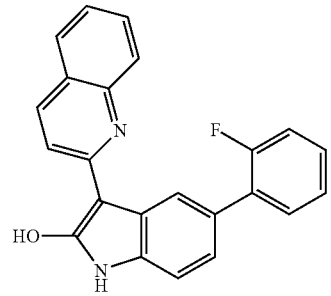

5-(2-Fluoro-phenyl)-3-quinolin-2-yl-1H-indol-2-ol: ¹H NMR (400 MHz, DMSO-d6): δ 7.04 (m, 1H), 7.16 (d, 1H), 7.23-7.44 (m, 4H), 7.55-7.70 (m, 3H), 7.71-7.85 (m, 3H), 8.07 (d, 1H), 10.75 (s, 1H), 14.45 (s, 1H). ESI-MS: m/z 354.8 (M+H)⁺.

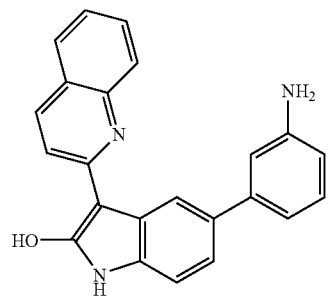

5-(3-Amino-phenyl)-3-quinolin-2-yl-1H-indol-2-ol: ¹H NMR (400 MHz, DMSO-d6): δ 3.65-4.70 (br s, 2H), 7.03 (d, 2H), 7.23 (d, 1H), 7.32 (t, 1H), 7.41 (m, 2H), 7.49 (d, 1H), 7.58 (d, 1H), 7.66 (q, 1H), 7.79 (m, 2H), 7.87 (d, 1H), 8.11 (d, 1H), 10.75 (s, 1H), 14.45 (s, 1H). ESI-MS: m/z 351.8 (M+H)⁺.

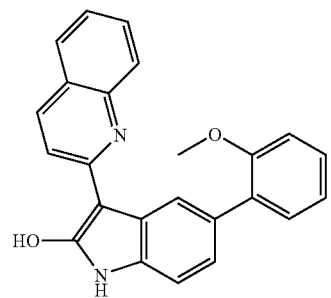

5-(2-Methoxy-phenyl)-3-quinolin-2-yl-1H-indol-2-ol: ¹H NMR (400 MHz, DMSO-d6): δ 3.80 (s, 3H), 6.94 (d, 1H), 6.99-7.13 (m, 3H), 7.26-7.38 (m, 3H), 7.55 (d, 1H), 7.58-7.67 (m, 2H), 7.67-7.77 (m, 2H), 8.04 (d, 1H), 10.65 (s, 1H), 14.35 (s, 1H). ESI-MS: m/z 367.8 (M+H)⁺.

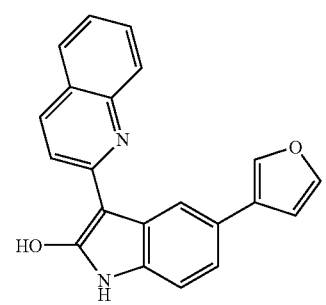

5-(3-Furan)-3-quinolin-2-yl-1H-indol-2-ol: ¹H NMR (400 MHz, DMSO-d6): δ 7.15 (d, 1H), 7.267 (s, 1H), 7.45 (d, 1H), 7.53 (t, 1H), 7.77 (d, 1H), 7.84 (d, 1H), 7.95 (s, 1H), 8.04 (m, 2H), 8.14 (d, 1H), 8.28 (d, 1H), 8.43 (s, 1H), 10.85 (s, 1H), 14.70 (s, 1H). ESI-MS: m/z 326.8 (M+H)⁺.

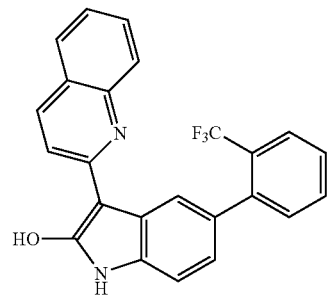

5-(2-Trifluoromethyl-phenyl)-3-quinolin-2-yl-1H-indol-2-ol: ¹H NMR (400 MHz, DMSO-d6): δ 6.92 (d, 1H), 6.97 (m, 2H), 7.32 (q, 1H), 7.48 (d, 1H), 7.52-7.67 (m, 3H), 7.68-7.79 (m, 3H), 7.83 (t, 1H), 7.98-8.05 (m, 1H), 10.75 (s, 1H), 14.45 (s, 1H). ). ESI-MS: m/z 408.8 (M+H)⁺.

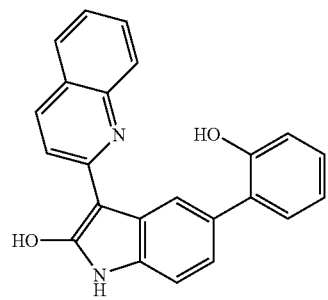

5-(2-Hydroxy-phenyl)-3-quinolin-2-yl-1H-indol-2-ol: $^1$H NMR (400 MHz, DMSO-d6): δ 6.82-6.99 (m, 3H), 7.08-7.19 (m, 2H), 7.23-7.35 (m, 2H), 7.54 (d, 1H), 7.61 (d, 1H), 7.67-7.78 (m, 3H), 8.04 (q, 1H), 9.35 (br s, 1H), 10.65 (s, 1H), 14.35 (s, 1H). ). ESI-MS: m/z 352.8(M+H)$^+$.

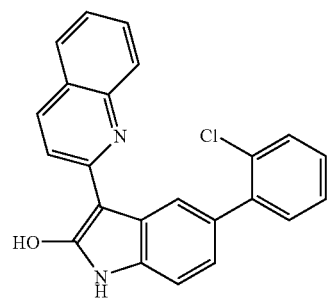

5-(2-Chloro-phenyl)-3-quinolin-2-yl-1H-indol-2-ol: $^1$H NMR (400 MHz, DMSO-d6): δ 6.2-6.99 (m, 3H), 7.24 (t, 1H), 7.27-7.44 (m, 4H), 7.45-7.63 (m, 3H), 7.70 (d, 1H), 7.98 (d, 1H), 10.65 (s, 1H), 14.35 (s, 1H). ). ESI-MS: m/z 337.8 (M+H)$^+$.

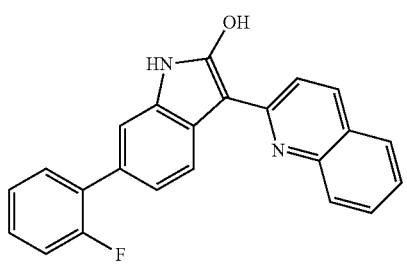

6-(2-Fluoro-phenyl)-3-quinolin-2-yl-1H-indol-2-ol: $^1$H NMR (400 MHz, DMSO-d6): δ 7.32 (s, 1H), 7.37 (d, 1H), 7.43-7.58 (m, 4H), 7.70-7.87 (m, 4H), 7.92-7.83 (m, 2H), 8.29 (d, 1H), 10.90 (s, 1H), 14.55 (S, 1H). ). ESI-MS: m/z 355.8 (M+H)$^+$.

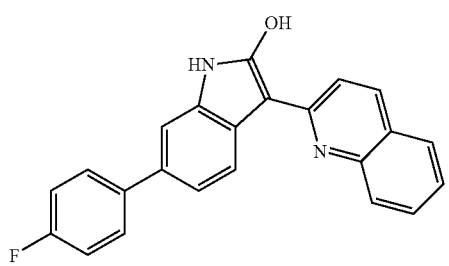

6-(4-Fluoro-phenyl)-3-quinolin-2-yl-1H-indol-2-ol: $^1$H NMR (400 MHz, DMSO-d6): δ 7.08 (s, 1H), 7.16-7.30 (m, 5H), 7.48-7.76 (m, 6H), 8.02 (d, 1H), 10.65 (s, 1H), 14.30 (s, 1H). ESI-MS: m/z 352.0 (M+H)$^+$.

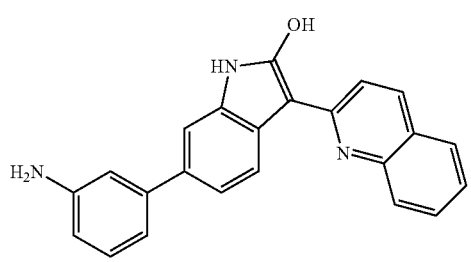

6-(3-Amino-phenyl)-3-quinolin-2-yl-1H-indol-2-ol: $^1$H NMR (400 MHz, DMSO-d6): δ 4.55 (s, 2H), 7.12 (d, 1H), 7.18-7.28 (m, 2H), 7.32 (d, 2H), 7.47-7.59 (m, 4H), 7.65 (d, 1H), 7.68-7.76 (m, 2H), 8.02 (d, 1H), 10.65 (s, 1H), 14.25 (s, 1H). ). ESI-MS: m/z 351.6 (M+H)$^+$.

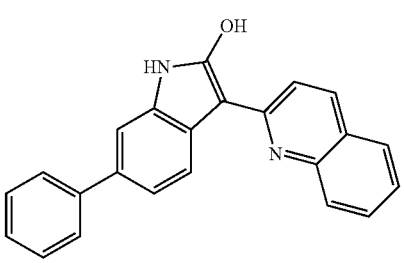

6-(Phenyl)-3-quinolin-2-yl-1H-indol-2-ol: $^1$H NMR (400 MHz, DMSO-d6): δ 7.12 (d, 1H), 7.19-7.30 (m, 3H), 7.38 (t, 2H), 7.49-7.62 (m, 4H), 7.67 (d, 1H), 7.74 (t, 2H), 8.22 (s, 1H), 10.65 (s, 1H), 14.30 (s, 1H). ). ESI-MS: m/z 336.8 (M+H)$^+$.

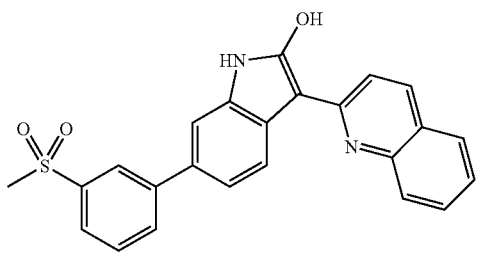

6-(3-Methanesulfonyl-phenyl)-3-quinolin-2-yl-1H-indol-2-ol: $^1$H NMR (400 MHz, DMSO-d6): δ 3.25 (s, 3H), 7.22 (s, 1H), 7.25-7.35 (m, 2H), 7.53-7.62 (m, 2H), 7.65 (t, 1H), 7.70-7.83 (m, 4H), 7.96 (d, 1H), 8.03-8.15 (m, 2H), 10.70 (s, 1H), 14.35 (s, 1H). ). ESI-MS: m/z 414.7 (M+H)$^+$.

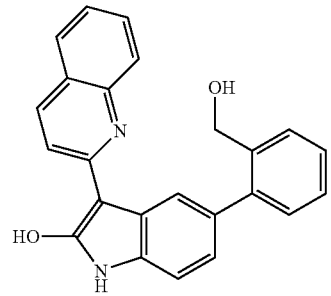

5-(2-Hydroxymethyl-phenyl)-3-quinolin-2-yl-1H-indol-2-ol: $^1$H NMR (400 MHz, DMSO-d6): δ 4.40 (s, 2H), 5.15 (s, 1H), 6.95 (s, 2H), 7.20-7.45 (m, 4H), 7.55-7.75 (m, 4H), 7.80 (d, 2H), 8.05 (d, 1H), 10.65 (s, 1H), 10.40 (s, 1H). ESI-MS: m/z 367.8 (M+H)$^+$.

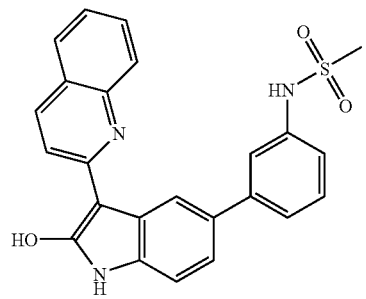

5-(3-Methanesulfonyl-amino-phenyl)-3-quinolin-2-yl-1H-indol-2-ol: $^1$H NMR (400 MHz, DMSO-d6): δ 3.02 (s, 3H), 7.02 (d, 1H), 7.18 (m, 2H), 7.33 (t, 1H), 7.38-7.51 (m, 3H), 7.52-7.69 (m, 2H), 7.70-7.88 (m, 3H), 8.10 (d, 1H), 9.75 (s, 1H), 10.70 (s, 1H), 14.45 (s, 1H). ESI-MS: m/z 429.7 (M+H)$^+$.

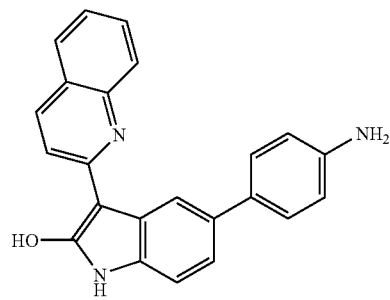

5-(4-Amino-phenyl)-3-quinolin-2-yl-1H-indol-2-ol: $^1$H NMR (400 MHz, DMSO-d6): δ 6.95 (d, 1H), 7.15-7.27 (m, 4H), 7.33 (q, 1H), 7.52-7.68 (m, 2H), 7.67-7.85 (m, 3H), 7.88 (d, 1H), 8.07 (t, 1H), 10.65 (s, 1H), 14.45 (s, 1H). ESI-MS: m/z 351.8 (M+H)$^+$.

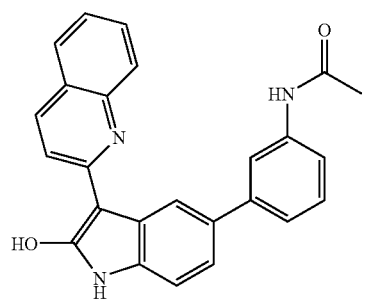

5-(3-Acetamide-phenyl)-3-quinolin-2-yl-1H-indol-2-ol: $^1$H NMR (400 MHz, DMSO-d6): δ 2.05 (s, 3H), 6.97 (d, 1H), 7.25 (d, 1H), 7.35 (d, 1H), 7.53-7.69 (m, 6H), 7.77 (m, 2H), 7.90 (d, 1H), 8.07 (d, 1H), 9.95 (s, 1H), 10.65 (s, 1H), 14.45 (s, 1H). ). ESI-MS: m/z 393.8 (M+H)$^+$.

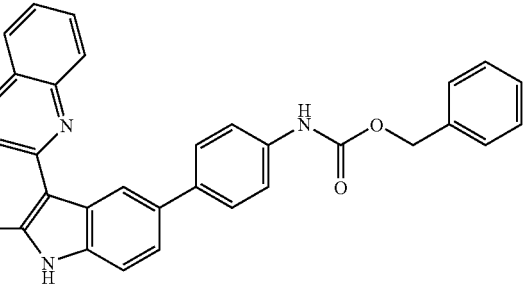

5-(4-Carbamic acid benzyl ester)-3-quinolin-2-yl-1H-indol-2-ol: $^1$H NMR (400 MHz, DMSO-d6): δ 5.20 (s, 2H), 7.00 (d, 1H), 7.15-7.75 (m, 13H), 7.77 (d, 2H), 7.90 (d, 1H), 8.05 (d, 1H), 9.80 (s, 1H), 10.65 (s, 1H), 14.45 (s, 1H). ESI-MS: m/z 485.7 (M+H)$^+$.

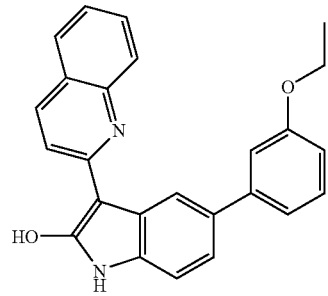

5-(3-Ethoxy-phenyl)-3-quinolin-2-yl-1H-indol-2-ol: ¹H NMR (400 MHz, DMSO-d6): δ 1.35 (s, 3H), 4.10 (s, 2H), 6.75-7.05 (m, 2H), 7.05-7.40 (m, 4H), 7.45-7.66 (m, 2H), 7.67-7.95 (m, 3H), 8.00-8.15 (m, 2H), 10.70 (s, 1H), 14.45 (s, 1H). ESI-MS: m/z 380.7 (M+H)⁺.

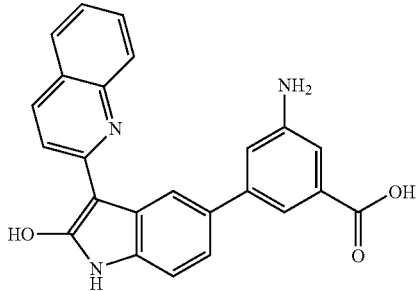

5-(3-Amino-5-carboxy-phenyl)-3-quinolin-2-yl-1H-indol-2-ol: ¹H NMR (400 MHz, DMSO-d6): δ 7.02 (d, 1H), 7.15-7.26 (m, 3H), 7.34 (t, 1H), 7.58 (d, 1H), 7.63 (t, 1H), 7.71-7.85 (br m, 4H), 8.13 (d, 1H), 10.70(s, 1H), 14.45 (s, 1H). ESI-MS: m/z 395.7 (M+H)⁺.

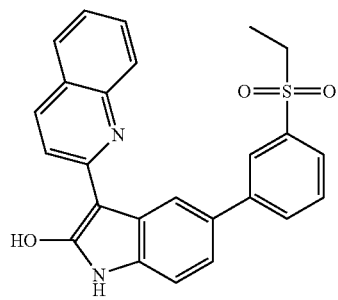

5-(3-Ethanesulfonyl-phenyl)-3-quinolin-2-yl-1H-indol-2-ol: ¹H NMR (400 MHz, DMSO-d6): δ 1.40 (d, 3H), 3.65 (t, 2H), 7.30 (t, 1H), 7.56 (m, 2H), 7.78-7.91 (m, 2H), 7.96-8.10 (m, 3H), 8.10-8.22 (m, 2H), 8.35 (m, 3H), 11.10 (s, 1H), 14.7 (s, 1H). ESI-MS: m/z 428.7 (M+H)⁺.

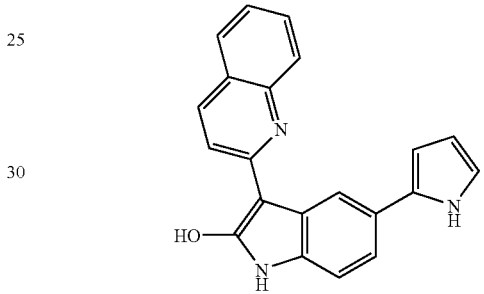

5-(2-Pyrrole)-3-quinolin-2-yl-1H-indol-2-ol: ¹H NMR (400 MHz, DMSO-d6): δ 6.11 (d, 1H), 6.45 (s, 1H), 6.83 (s, 1H), 6.90 (d, 1H), 7.26 (d, 1H), 7.32 (t, 1H), 7.55 (d, 1H), 7.63 (t, 1H), 7.78-7.86 (m, 2H), 7.95 (d, 1H), 8.11 (d, 1H), 10.55(s, 1H), 11.20 (s, 1H), 14.45 (s, 1H). ESI-MS: m/z 325.8 (M+H)⁺.

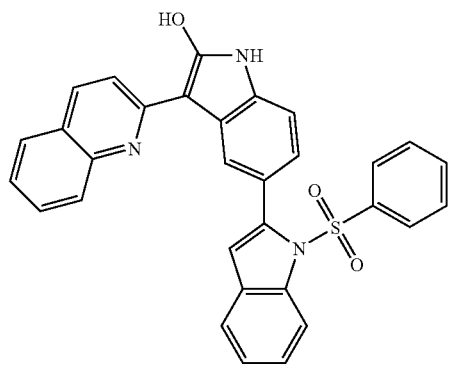

1-Benzenesulfonyl-3'-quinolin-2-yl-1H,1'H-[2,5']biindolyl-2'-ol: ¹H NMR (400 MHz, DMSO-d6): δ 7.05 (d, 1H), 7.25-7.50 (br m, 5H), 7.51-7.95 (br m, 7H), 8.01-8.20 (br m, 6H), 10.70 (s, 1H), 14.45 (s, 1H). ESI-MS: m/z 515.7 (M+H)⁺.

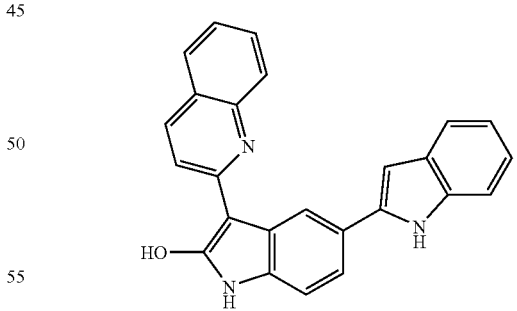

5-(2-Indol)-3-quinolin-2-yl-1H-indol-2-ol: ¹H NMR (400 MHz, DMSO-d6): δ 6.89 (s, 1H), 6.95-7.02 (m, 2H), 7.08 (t, 1H), 7.37 (t, 1H), 7.43 (d, 1H), 7.53 (t, 2H), 7.55-7.69 (m, 2H), 7.85 (d, 1H), 7.01-8.09 (m, 2H), 8.19 (d, 1H), 10.75 (s, 1H), 11.45 (s, 1H), 14.45 (s, 1H). ESI-MS: m/z 375.8 (M+H)⁺.

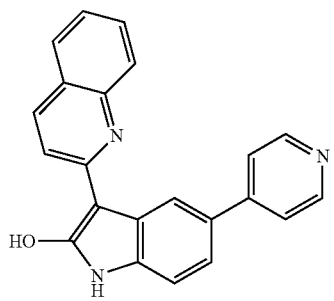

5-Pyridin-4-yl-3-quinolin-2-yl-1H-indol-2-ol: ¹H NMR (400 MHz, DMSO-d6): δ 7.12 (d, J=8.08 Hz, 1H), 7.34 (s, 2H), 7.67 (m, 2H), 7.84 (d, 1H), 7.94-8.06 (m, 2H), 8.17 (d, J=4.04 Hz, 2H), 8.41 (s, 1H), 8.80 (s, 2H), 11.03 (s, 1H), 14.51 (s, 1H). ESI-MS: m/z 338.1 (M+H)⁺.

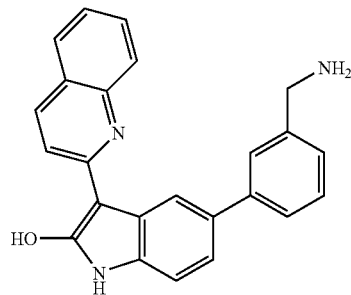

5-(3-Aminomethyl-phenyl)-3-quinolin-2-yl-1H-indol-2-ol: ¹H NMR (400 MHz, DMSO-d6): δ 5.02 (s, 2H), 6.49 (bs, 2H), 7.02 (d, 1H), 7.34 (m, 3H), 7.49 (t, 1H), 7.58 (d, 1H), 7.63 (d, 1H), 7.76 (m, 2H), 7.86 (s, 2H), 7.91 (d, 1H), 8.09 (d, 1H), 10.72 (s, 1H), 14.45 (s, 1H). ESI-MS: m/z 366.1 (M+H)⁺.

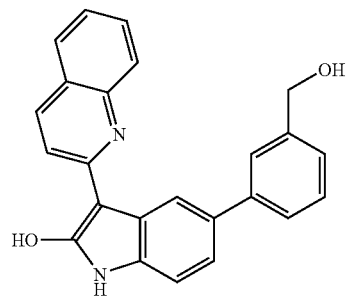

5-(3-Hydroxymethyl-phenyl)-3-quinolin-2-yl-1H-indol-2-ol: ¹H NMR (400 MHz, DMSO-d6): δ 4.58 (s, 2H), 5.19 (s, 1H), 7.00 (d, J=8.08 Hz, 1H), 7.22-7.33 (m, 4H), 7.39 (t, J=7.58 Hz, 1H), 7.53-7.65 (m, 4H), 7.75-7.87 (m, 4H), 8.09 (d, J=9.35 Hz, 1H), 10.67 (s, 1H), 14.43 (s, 1H). ESI-MS: m/z 367.1 (M+H)⁺.

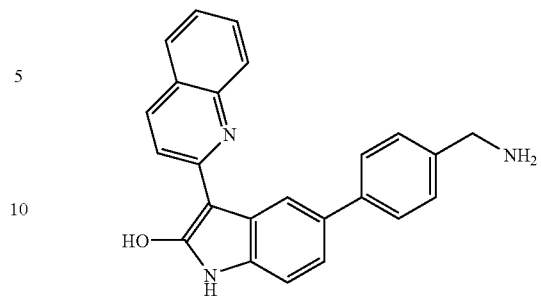

5-(4-Aminomethyl-phenyl)-3-quinolin-2-yl-1H-indol-2-ol: ¹H NMR (400 MHz, DMSO-d6): δ 4.09 (s, 2H), 6.52 (bs, 2H), 7.01 (s, 1H), 7.30 (m, 2H), 7.50-7.60 (m, 4H), 7.79 (m, 3H), 8.09 (m, 3H), 10.70 (s, 1H), 14.45 (s, 1H). ESI-MS: m/z 366.1 (M+H)⁺.

The following compounds were prepared according to Procedure C:

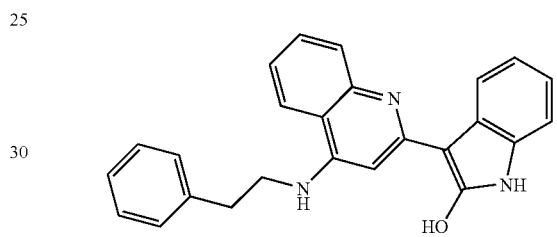

3-(4-Phenethylamino-quinolin-2-yl)-1H-indol-2-ol: ¹H NMR (400 MHz, DMSO-d6) δ 3.02-3.13 (m, 2H), 3.64-3.74 (m, 2H), 6.38 (s, 1H), 6.84-6.95 (m, 3H,) 7.23-7.31 (m, 2H), 7.33-7.41 (m, 4H), 7.47 (d, J=7.83 Hz, 1H), 7.60 (d, J=7.07 Hz, 1H), 7.83 (d, J=5.56 Hz, 1H), 8.11 (d, J=8.08 Hz, 1H), 10.29 (s, 1H), 14.07 (s, 1H). ESI-MS: m/z 380.1 (M+H)⁺.

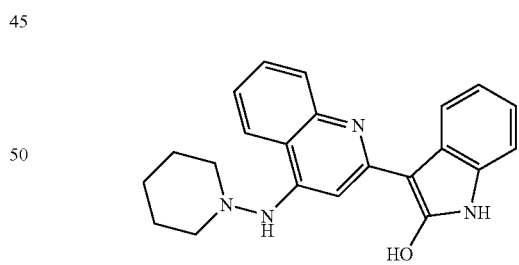

3-(4-Piperidinylamino-quinolin-2-yl)-1H-indol-2-ol: ¹H NMR (400 MHz, DMSO-d6) δ 1.69-1.70 (m, 2H), 1.74-1.89 (m, 4H), 3.18-3.36 (m, 4H), 6.83 (s, 1H), 6.85-7.01 (m, 3H), 7.31 (t, J=8.08 Hz, 1H), 7.43 (d, J=7.07 Hz, 1H), 7.51 (d, J=7.58 Hz, 1H), 7.60 (t, J=8.21 Hz, 1H), 7.74 (d, J=8.08 Hz, 1H), 10.45 (s, 1H), 14.22 (s, 1H). ESI-MS: m/z 343.1 (M+H)⁺.

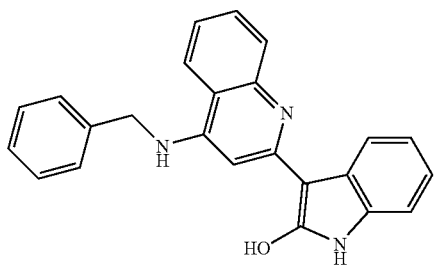

3-(4-Benzylamino-quinolin-2-yl)-1H-indol-2-ol: ¹H NMR (400 MHz, DMSO-d6) δ 4.63-4.74 (m, 2H), 6.11 (s, 1H), 6.74-6.85 (m, 2H), 6.86-6.95 (m, 1H), 7.26 (t, J=7.33 Hz, 1H), 7.30-7.42 (m, 3H), 7.44-7.53 (m, 3H), 7.57-7.68 (m, 1H), 8.21 (d, J=8.34 Hz, 1H), 8.47 (d, J=5.81 Hz, 1H), 10.21 (s, 1H), 13.96 (s, 1H). ESI-MS: m/z 366.1 (M+H)⁺.

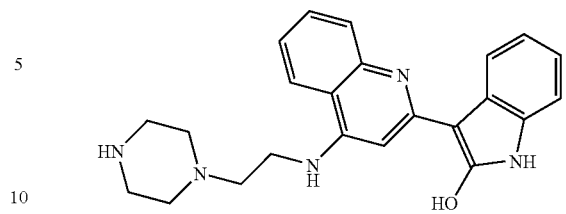

3-[4-(2-piperazin-1-yl-ethylamino)-quinolin-2-yl]-1H-indol-2-ol: ¹H NMR (400 MHz, DMSO-d6) δ 2.63-2.75 (m, 2H), 3.21-3.41 (m, 12H), 6.84 (s, 1H), 6.87-7.00 (m, 3H), 7.30 (t, J=7.07 Hz, 1H), 7.45 (d, J=7.07 Hz, 1H), 7.52 (d, J=8.34 Hz, 1H), 7.61 (t, J=8.08 Hz, 1H), 7.77 (d, J=8.08 Hz, 1H), 10.46 (s, 1H), 14.11 (bs, 1H). ESI-MS: m/z 388.1 (M+H)⁺.

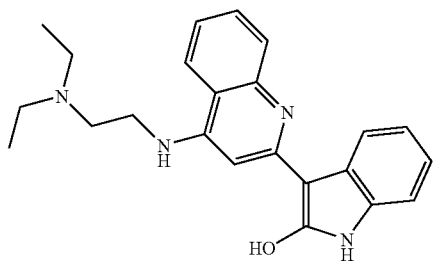

3-[4-(2-Diethylamino-ethylamino)-quinolin-2-yl]-1H-indol-2-ol: ¹H NMR (400 MHz, DMSO-d6) δ 0.86-0.95 (m, 6H), 2.38-2.60 (m, 6H), 2.65-2.76 (m, 2H), 6.40 (s, 1H), 6.87 (m, 2H), 7.27 (m, 1H), 7.45 (m, 2H), 7.59 (m, 1H), 7.77 (m, 1H), 8.05 (m, 1H), 10.28 (s, 1H), 14.04 (bs, 1H). ESI-MS: m/z 375.1 (M+H)⁺.

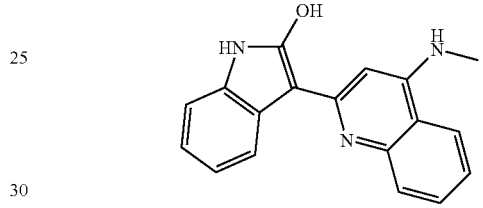

3-(4-Methylamino-quinolin-2-yl)-1H-indol-2-ol: ¹H NMR (400 MHz, DMSO-d6) δ 3.07 (d, J=4.55 Hz, 3H), 6.24 (s, 1H), 6.79-6.97 (m, 3H), 7.29 (t, J=8.21 Hz, 1H), 7.38-7.49 (m, 2H), 7.61 (t, J=8.21 Hz, 1H), 7.82-7.91 (m, 1H), 8.05 (d, J=8.08 Hz, 1H), 10.27 (s, 1H), 14.08 (s, 1H). ESI-MS: m/z 290.1 (M+H)⁺.

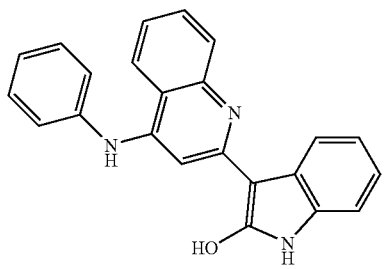

3-(4-Phenylamino-qunolin-2-yl)-1H-indol-2-ol: ¹H NMR (400 MHz, DMSO-d6) δ 6.67-6.88 (m, 5H), 7.31-7.40 (m, 2H), 7.44-7.62 (m, 5H), 7.68 (t, J=8.21 Hz, 1H), 8.29 (d, J=8.08 Hz, 1H), 9.35 (s, 1H), 10.31 (s, 1H), 14.05 (s, 1H). ESI-MS: m/z 351.2 (M+H)⁺.

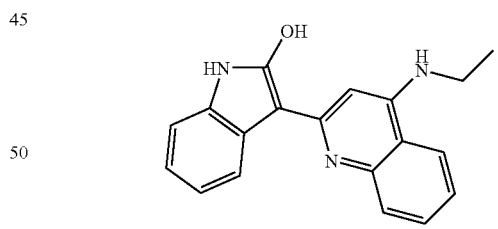

3-(4-Ethylamino-quinolin-2-yl)-1H-indol-2-ol: ¹H NMR (400 MHz, CDCl₃) δ 1.37 (q, J=6.74 Hz, 3H), 3.38-3.55 (m, 2H), 6.32 (s, 1H), 6.79-6.97 (m, 3H), 7.29 (t, J=7.20 Hz, 1H), 7.40 (d, J=7.83 Hz, 1H), 7.46 (d, J=7.83 Hz, 1H), 7.61 (t, J=7.07 Hz, 1H), 7.66 (t, J=5.05 Hz, 1H), 8.15 (d, J=8.08 Hz, 1H), 10.27 (s, 1H), 14.08 (s, 1H). ESI-MS: m/z 304.1 (M+H)⁺.

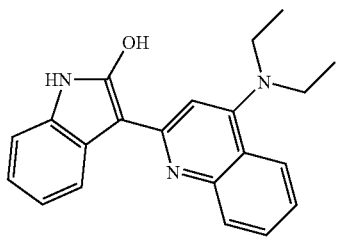

3-(4-Diethylamino-quinolin-2-yl)-1H-indol-2-ol: ESI-MS: m/z 332.1 (M+H)⁺.

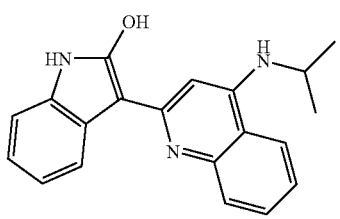

3-(4-Isopropylamino-quinolin-2-yl)-1H-indol-2-ol: ¹H NMR (400 MHz, DMSO-d6) δ 1.38 (d, J=6.32 Hz, 6H), 3.99-4.12 (m, 1H), 6.36 (s, 1H), 6.75-6.98 (m, 3H), 7.29 (dd, J=15.92, 7.58 Hz, 2H), 7.39 (d, J=7.58 Hz, 1H), 7.45 (d, J=8.08 Hz, 1H), 7.61 (t, J=7.71 Hz, 1H), 8.23 (d, J=8.08 Hz, 1H), 10.27 (s, 1H), 14.08 (s, 1H). ESI-MS: m/z 318.1 (M+H)⁺.

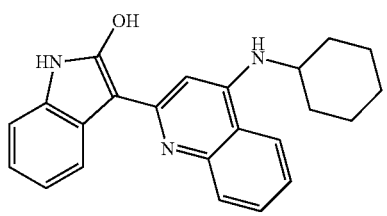

3-(4-Cyclohexylamino-quinolin-2-yl)-1H-indol-2-ol: ¹H NMR (400 MHz, DMSO-d6) δ 0.95-1.32 (m, 2H), 1.31-1.58 (m, 4H), 1.84 (s, 2H), 2.02-2.20 (m, 2H), 3.54-3.73 (m, 1H), 6.38 (s, 1H), 6.74-7.00 (m, 3H), 7.16-7.38 (m, 3H), 7.45 (d, J=8.08 Hz, 1H), 7.60 (t, J=8.08 Hz, 1H), 8.24 (d, J=8.08 Hz, 1H), 10.27 (s, 1H), 14.03 (s, 1H). ESI-MS: m/z 344.1 (M+H)⁺.

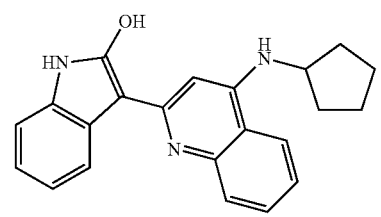

3-(4-Cyclopentylamino-quinolin-2-yl)-1H-indol-2-ol: ¹H NMR (400 MHz, DMSO-d6) δ 1.58-1.89 (m, 6H), 2.03-2.23 (m, 2H), 4.08-4.24 (m, 1H), 6.37 (s, 1H), 6.78-6.97 (m, 3H), 7.28 (t, J=7.58 Hz, 1H), 7.34 (d, J=5.56 Hz, 1H), 7.39 (d, J=7.58 Hz, 1H), 7.45 (d, J=8.08 Hz, 1H), 7.61 (t, J=7.58 Hz, 1H), 8.26 (d, J=8.08 Hz, 1H), 10.27 (s, 1H), 14.07 (s, 1H). ESI-MS: m/z 358.1 (M+H)⁺.

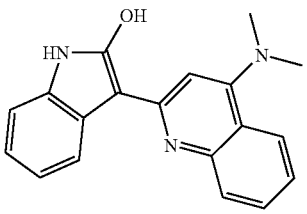

3-(4-Dimethylamino-quinolin-2-yl)-1H-indol-2-ol: ¹H NMR (400 MHz, DMSO-d6) δ 3.10-3.17 (m, 6H,) 6.68 (s, 1H), 6.82-6.99 (m, 3H), 7.29 (t, J=7.71 Hz, 1H), 7.43 (d, J=7.58 Hz, 1H), 7.51 (d, J=7.83 Hz, 1H), 7.60 (t, J=7.71 Hz, 1H), 7.90 (d, J=8.08 Hz, 1H), 10.40 (s, 1H), 14.13 (s, 1H). ESI-MS: m/z 304.1 (M+H)⁺.

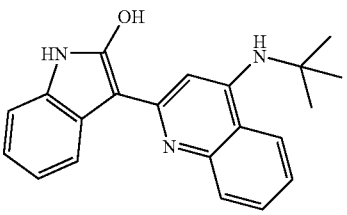

3-(4-tert-Butylamino-quinolin-2-yl)-1H-indol-2-ol: ¹H NMR (400 MHz, DMSO-d6) δ ppm 1.37 (s, 9H), 6.35 (s, 1H), 6.70-6.95 (m, 3H), 7.31 (dd, J=15.45, 7.63 Hz, 2H), 7.41 (d, J=7.55 Hz, 1H), 7.43 (d, J=8.01 Hz, 1H), 7.63 (t, J=7.74 Hz, 1H), 8.25 (d, J=8.05 Hz, 1H), 10.25 (s, 1H), 14.09 (s, 1H). ESI-MS: m/z 332.2 (M+H)⁺.

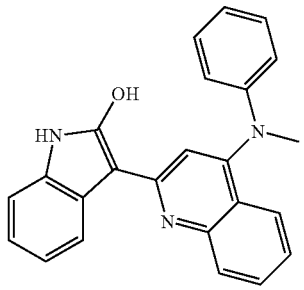

3-[4-(Methyl-phenyl-amino)-quinolin-2-yl]-1H-indol-2-ol: ¹H NMR (400 MHz, DMSO-d6) δ ppm 3.15 (s, 3H), 6.65-6.89 (m, 5H), 7.33-7.45 (m, 1H), 7.48-7.64 (m, 5H), 7.67 (t, J=8.14 Hz, 1H), 8.27 (d, J=8.11 Hz, 1H), 9.36 (s, 1H), 10.32 (s, 1H), 14.04 (s, 1H). ESI-MS: m/z 366.1 (M+H)⁺.

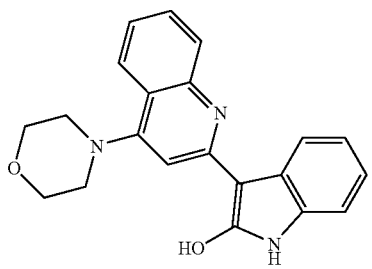

3-(4-Morpholin-4-yl-quinolin-2-yl)-1H-indol-2-ol: ¹H NMR (400 MHz, DMSO-d6) δ ppm 3.21-3.41 (m, 4H), 3.68-3.91 (m, 4H), 6.82(s, 1H), 6.85-7.02 (m, 3H), 7.31 (t, J=7.05 Hz, 1H), 7.42 (d, J=7.03 Hz, 1H), 7.51 (d, J=8.33 Hz, 1H), 7.62 (t, J=8.05 Hz, 1H), 7.72 (d, J=8.03 Hz, 1H), 10.41 (s, 1H), 14.11 (bs, 1H). ESI-MS: m/z 346.1 (M+H)⁺.

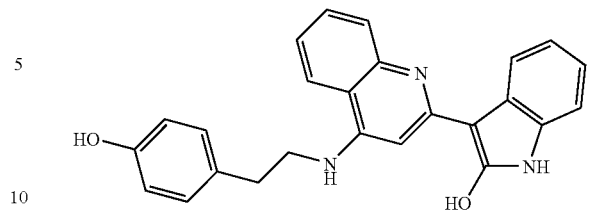

3-{4-[2-(4-Hydroxy-phenyl)-ethylamino]-quinolin-2-yl}-1H-indol-2-ol: ¹H NMR (400 MHz, DMSO-d6) δ ppm 3.07 (t, J=7.84 Hz, 2H), 3.63-3.76 (m, 2H), 6.36 (s, 1H), 6.80-6.99 (m, 3H), 7.15-7.45 (m, 6H), 7.46 (d, J=7.84 Hz, 1H), 7.63 (t, J=7.35 Hz, 1H), 7.82 (t, J=5.44 Hz, 1H), 8.11 (t, J=7.34 Hz, 1H), 10.27 (s, 1H), 13.09 (s, 1H), 14.12 (s, 1H). ESI-MS: m/z 396.1 (M+H)⁺.

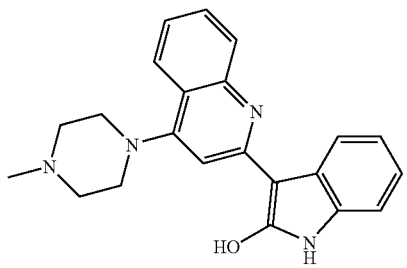

3-[4-(4-Methyl-piperazin-1-yl)-quinolin-2-yl]-1H-indol-2-ol: ¹H NMR (400 MHz, DMSO-d6) δ ppm 3.07 (s 3H), 3.18-3.33 (m, 4H), 3.34-3.61 (m, 4H), 6.81(s, 1H), 6.88-7.06 (m, 3H), 7.33 (t, J=7.08 Hz, 1H), 7.44 (d, J=7.05 Hz, 1H), 7.53 (d, J=8.31 Hz, 1H), 7.61 (t, J=8.03 Hz, 1H), 7.71 (d, J=8.01 Hz, 1H), 10.45 (s, 1H), 14.15 (bs, 1H). ESI-MS: m/z 359.2 (M+H)⁺.

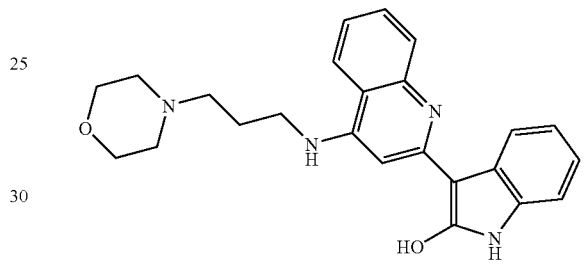

3-[4-(3-Morpholin-4-yl-propylamino)-quinolin-2-yl]-1H-indol-2-ol: ¹H NMR (400 MHz, DMSO-d6) δ ppm 1.81-2.00 (m, 2H), 3.17-3.65 (m, 12H), 6.33 (s, 1H), 6.77-6.96 (m, 3H), 7.30 (t, J=7.58 Hz, 1H), 7.40 (d, J=7.58 Hz, 1H), 7.46 (d, J=8.08 Hz, 1H), 7.61 (t, J=7.71 Hz, 1H), 7.79 (t, J=4.80 Hz, 1H), 8.11 (d, J=8.08 Hz, 1H), 10.28 (s, 1H), 14.07 (s, 1H). ESI-MS: m/z 403.1 (M+H)⁺.

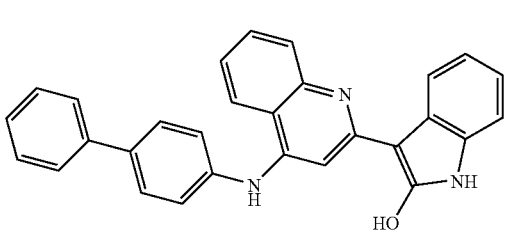

3-[4-(Biphenyl-4-ylamino)-quinolin-2-yl]-1H-indol-2-ol: ¹H NMR (400 MHz, DMSO-d6) δ ppm 6.58-6.97 (m, 9H), 7.30-7.42 (m, 2H), 7.43-7.63 (m, 5H), 7.66 (t, J=8.22 Hz, 1H), 8.27 (d, J=8.05 Hz, 1H), 9.36 (s, 1H), 10.34 (s, 1H), 14.09 (s, 1H). ESI-MS: m/z 428.2 (M+H)⁺.

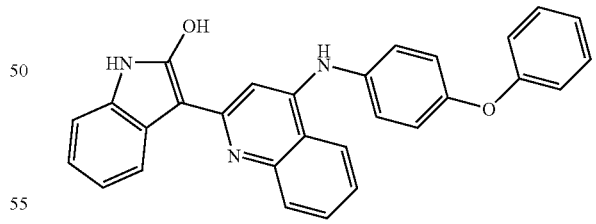

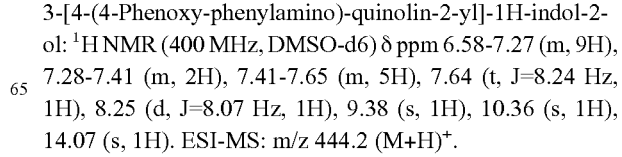

3-[4-(4-Phenoxy-phenylamino)-quinolin-2-yl]-1H-indol-2-ol: ¹H NMR (400 MHz, DMSO-d6) δ ppm 6.58-7.27 (m, 9H), 7.28-7.41 (m, 2H), 7.41-7.65 (m, 5H), 7.64 (t, J=8.24 Hz, 1H), 8.25 (d, J=8.07 Hz, 1H), 9.38 (s, 1H), 10.36 (s, 1H), 14.07 (s, 1H). ESI-MS: m/z 444.2 (M+H)⁺.

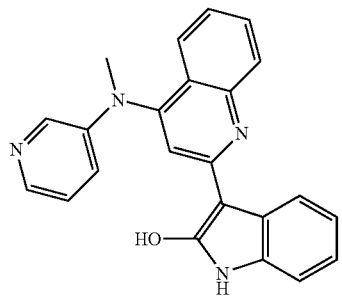

3-[4-(Methyl-pyridin-3-yl-amino)-quinolin-2-yl]-1H-indol-2-ol: $^1$H NMR (400 MHz, DMSO-d6) δ ppm 3.15 (s, 3H), 6.95-7.05 (m, 1H), 7.07 (d, J=8.01 Hz, 1H), 7.15 (d, J=7.98 Hz, 1H), 7.22 (s, 1H), 7.33-7.45 (m, 1H), 7.48-7.64 (m, 5H), 7.67 (t, J=8.14 Hz, 1H), 8.27 (d, J=8.11 Hz, 1H), 9.36 (s, 1H), 10.32 (s, 1H), 14.04 (s, 1H). ESI-MS: m/z 367.1 (M+H)$^+$.

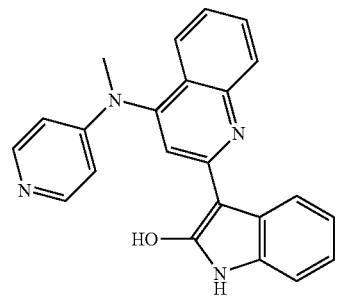

3-[4-(Methyl-pyridin-4-yl-amino)-quinolin-2-yl]-1H-indol-2-ol: $^1$H NMR (400 MHz, DMSO-d6) δ ppm 3.13 (s, 3H), 7.05 (d, J=7.85 Hz, 2H), 7.12 (d, J=7.85 Hz, 2H), 7.15 (d, J=7.98 Hz, 1H), 7.30-7.45 (m, 1H), 7.50-7.65 (m, 5H), 7.75 (t, J=8.14 Hz, 1H), 8.25 (d, J=8.11 Hz, 1H), 9.35 (s, 1H), 10.35 (s, 1H), 14.05 (s, 1H). ESI-MS: m/z 367.2 (M+H)$^+$.

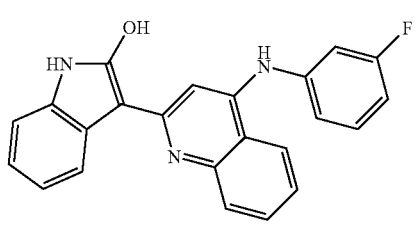

3-[4-(3-Fluoro-phenylamino)-quinolin-2-yl]-1H-indol-2-ol: $^1$H NMR (400 MHz, DMSO-d6) δ ppm 6.85-6.95 (m, 1H), 6.95-7.05 (m, 1H), 7.05-7.20 (m, 2H), 7.26 (s, 1H), 7.32-7.46 (m, 1H), 7.49-7.66 (m, 5H), 7.75 (t, J=8.12 Hz, 1H), 8.27 (d, J=8.12 Hz, 1H), 9.35 (s, 1H), 10.33 (s, 1H), 14.09 (s, 1H). ESI-MS: m/z 370.1 (M+H)$^+$.

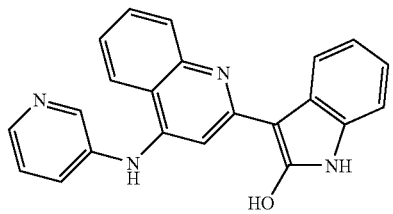

3-[4-(Pyridin-3-ylamino)-quinolin-2-yl]-1H-indol-2-ol: $^1$H NMR (400 MHz, DMSO-d6) δ ppm 6.90-7.02 (m, 1H), 7.04 (d, J=8.11 Hz, 1H), 7.09 (s, 1H), 7.16 (d, J=7.94 Hz, 1H), 7.23 (s, 1H), 7.30-7.45 (m, 1H), 7.49-7.65 (m, 5H), 7.69 (t, J=8.11 Hz, 1H), 8.25 (d, J=8.11 Hz, 1H), 9.39 (s, 1H), 10.35 (s, 1H), 14.14 (s, 1H). ESI-MS: m/z 353.1 (M+H)$^+$.

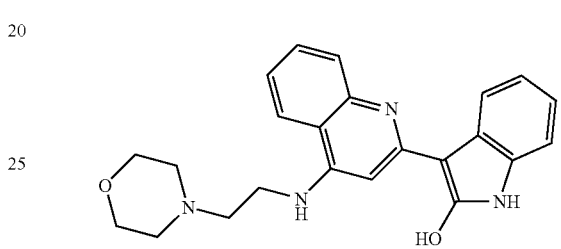

3-[4-(2-Morpholin-4-yl-ethylamino)-quinolin-2-yl]-1H-indol-2-ol: ESI-MS: m/z 389.2 (M+H)$^+$.

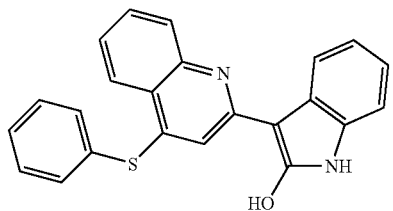

3-(4-Phenylsulfanyl-quinolin-2-yl)-1H-indol-2-ol: $^1$H NMR (400 MHz, DMSO-d6) δ 6.18 (d, J=7.58 Hz, 1H), 6.59 (s, 1H), 6.64 (t, J=7.33 Hz, 1H), 6.81-6.91 (m, 2H), 7.38 (t, J=7.58 Hz, 1H), 7.59 (d, J=8.34 Hz, 1H), 7.69 (t, J=7.58 Hz, 1H), 7.75 (d, J=7.58 Hz, 2H), 7.80 (d, J=6.82 Hz, 1H), 7.85 (d, J=7.83 Hz, 2H), 7.92 (d, J=8.08 Hz, 1H), 10.48 (s, 1H), 13.82 (s, 1H). ESI-MS: m/z 369.1 (M+H)$^+$.

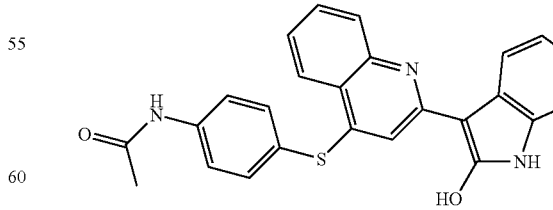

N-{4-[2-(2-Hydroxy-1H-indol-3-yl)-quinolin-4-yl-sulfanyl]-phenyl}-acetamide: $^1$H NMR MHz, DMSO-d6) δ 2.30 (s, 3H), 6.27 (d, J=7.83 Hz, 1H), 6.56 (s, 1H), 6.61 (t, J=7.58 Hz, 1H), 6.80-6.91 (m, 2H), 7.38 (t, J=7.58 Hz, 1H), 7.58 (d, J=8.08 Hz, 1H), 7.69 (t, J=7.71 Hz, 1H), 7.75 (d, J=8.59 Hz, 2H), 7.90 (d, J=7.83 Hz, 1H), 7.95 (d, J=8.59 Hz, 2H), 10.45 (d, J=16.93 Hz, 1H), 13.77 (s, 1H). ESI-MS: m/z 426.0 (M+H)⁺.

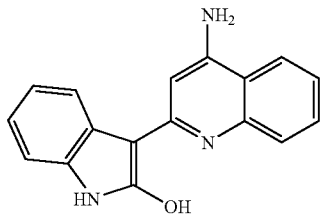

3-(4-Amino-quinolin-2-yl)-1H-indol-2-ol: ESI-MS: m/z 476.2 (M+H)⁺

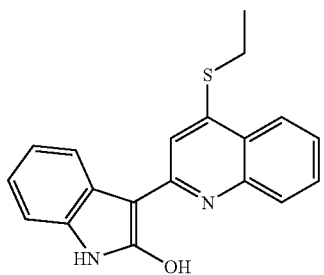

3-(4-Ethylsulfanyl-quinolin-2-yl)-1H-indol-2-ol: ESI-MS: m/z 321.3 (M+H)⁺

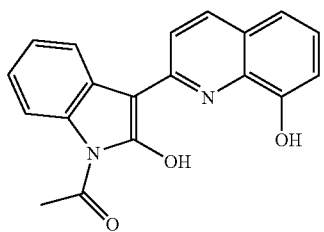

1-[2-Hydroxy-3-(8-hydroxy-quinolin-2-yl)-indol-1-yl]-ethanone: ESI-MS: m/z 319.3 (M+H)⁺

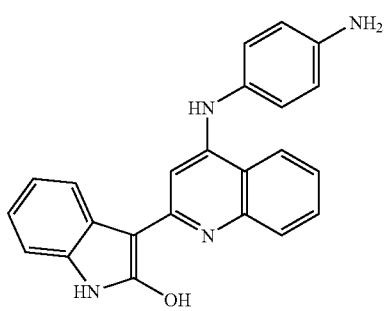

3-[4-(4-Amino-phenylamino)-quinolin-2-yl]-1H-indol-2-ol: ¹H NMR (400 MHz, DMSO-D6) δ ppm 6.69-6.77 (m, 2H) 6.79–6.88 (s, 2H) 7.32-7.44 (m, 3H) 7.52 (d, J=8.34 Hz, 1H) 7.66 (t, J=7.58 Hz, 1H) 8.26 (d, J=8.34 Hz, 1H) 9.28 (s, 1H) 10.31 (s, 1H) 14.00 (s, 1 H); ESI-MS: m/z 367.0 (M+H)⁺

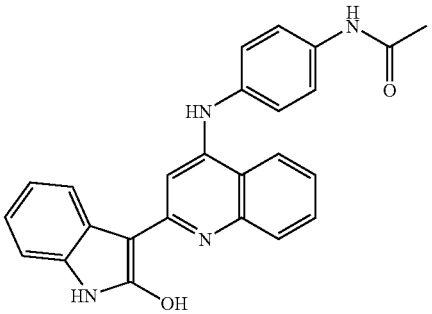

N-{4-[2-(2-Hydroxy-1H-indol-3-yl)-quinolin-4-ylamino]-phenyl}-acetamide: ¹H NMR (400 MHz, DMSO-D6) δ ppm 2.09 (s, 3H) 6.66-6.75 (m, 2H) 6.76-6.87 (m, 3H) 7.31-7.38 (m, 1H) 7.43 (d, J=8.59 Hz, 2H) 7.52 (d, J=8.08 Hz, 1H) 7.66 (t, J=7.71 Hz, 1H) 7.76 (d, J=8.59 Hz, 2H) 8.28 (d, J=7.83 Hz, 1H) 9.30 (s, 1H) 10.11 (s, 1H) 10.30 (s, 1H) 13.99 (s, 1H); ESI-MS: m/z 409.1 (M+H)⁺

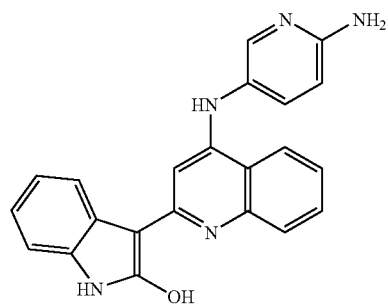

3-[4-(6-Amino-pyridin-3-ylamino)-quinolin-2-yl]-1H-indol-2-ol: ¹H NMR (400 MHz, DMSO-D6) δ ppm 6.49 (s, 1H) 6.75-6.87 (m, 3H) 6.93 (d, J=7.58 Hz, 1H) 7.08 (d, J=9.09 Hz, 1H) 7.37 (t, J=7.45 Hz, 1H) 7.54 (d, J=8.08 Hz, 1H) 7.67 (t, J=7.45 Hz, 1H) 8.06-8.10 (m, 2H) 8.19 (d, J=8.59 Hz, 1H) 9.24 (s, 1H) 10.35 (s, 1H) 14.09 (s, 1H); ESI-MS: m/z 368.1 (M+H)⁺

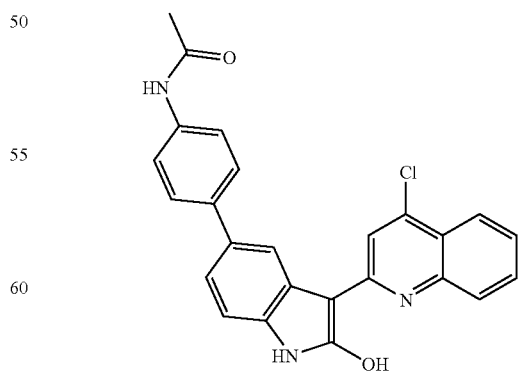

N-{4-[3-(4-Chloro-quinolin-2-yl)-2-hydroxy-1H-indol-5-yl]-phenyl}-acetamide: ¹H NMR (400 MHz, DMSO-D6) δ ppm 2.06 (s, 3H) 6.98 (d, J=8.08 Hz, 1H) 7.24 (d, J=8.08 Hz, 1H) 7.40 (t, J=7.58 Hz, 1H) 7.59-7.66 (m, 5H) 7.68-7.73 (m, 1H) 7.77 (s, 1H) 7.90-7.95 (m, 2H) 9.98 (s, 1H) 10.75 (s, 1H) 14.44 (s, 1H); ESI-MS: m/z 428.0 (M+H)$^+$

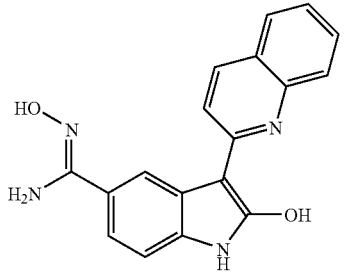

2,N-Dihydroxy-3-quinolin-2-yl-1H-indole-5-carboxamidine: ESI-MS: m/z 319 (M+H)$^+$

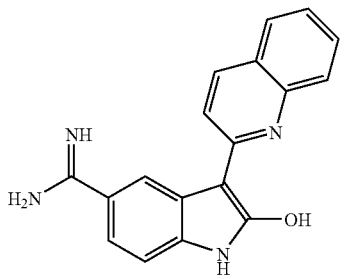

2-Hydroxy-3-quinolin-2-yl-1H-indole-5-carboxamidine: ESI-MS: m/z 303 (M+H)$^+$

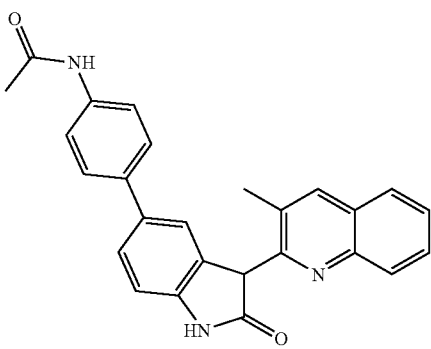

N-{4-[3-(3-Methyl-quinolin-2-yl)-2-oxo-2,3-dihydro-1H-indol-5-yl]-phenyl}-acetamide: $^1$H NMR (400 MHz, DMSO-D6) δ ppm 2.02 (m, 6H) 5.39 (s, 1H) 6.99 (d, J=8.08 Hz, 1H) 7.19 (s, 1H) 7.44 (d, J=7.83 Hz, 2H) 7.48-7.58 (m, 4H) 7.63 (d, J=8.34 Hz, 2H) 7.79-7.90 (m, 2H) 8.19 (s, 2H) 9.92 (s, 2H) 9.99 (s, 1H) 10.71 (s, 1H); ESI-MS: m/z 408.0 (M+H)$^+$

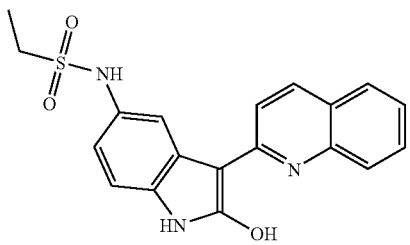

Ethanesulfonic acid (2-hydroxy-3-quinolin-2-yl-1H-indol-5-yl)-amide: ESI-MS: m/z 368.2 (M+H)$^+$

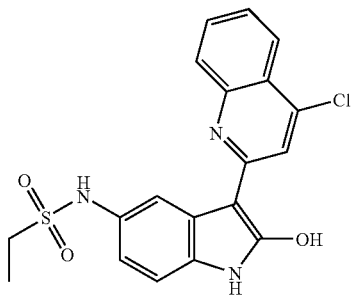

Ethanesulfonic acid [3-(4-chloro-quinolin-2-yl)-2-hydroxy-1H-indol-5-yl]-amide: ESI-MS: m/z 402.1 (M+H)$^+$

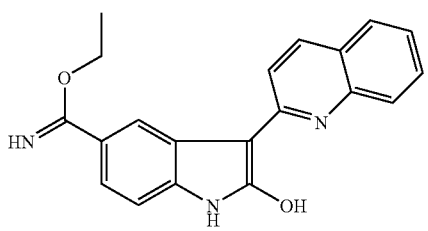

2-Hydroxy-3-quinolin-2-yl-1H-indole-5-carboximidic acid ethyl ester: ESI-MS: m/z 332 (M+H)$^+$

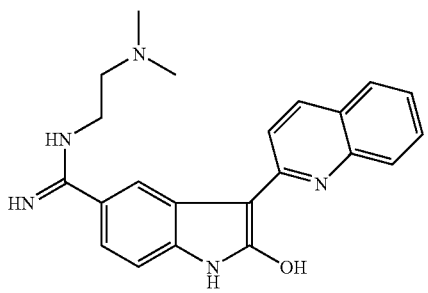

N-(2-Dimethylamino-ethyl)-2-hydroxy-3-quinolin-2-yl-1H-indole-5-carboxamidine: ESI-MS: m/z 374.1 (M+H)⁺

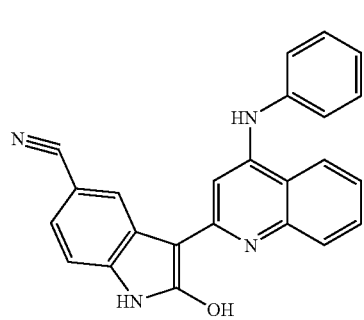

2-Hydroxy-3-(4-phenylamino-quinolin-2-yl)-1H-indole-5-carbonitrile: ESI-MS: m/z 377.2 (M+H)⁺

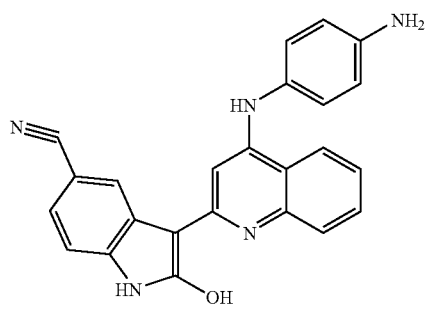

3-[4-(4-Amino-phenylamino)-quinolin-2-yl]-2-hydroxy-1H-indole-5-carbonitrile: ESI-MS: m/z 392.2 (M+H)⁺

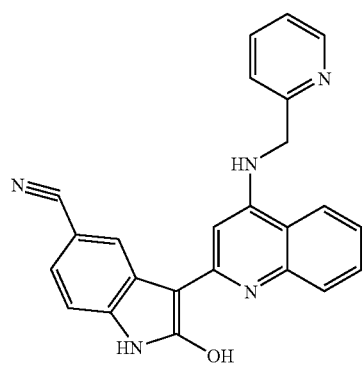

2-Hydroxy-3-{4-[(pyridin-2-ylmethyl)-amino]-quinolin-2-yl}-1H-indole-5-carbonitrile: ESI-MS: m/z 392.2 (M+H)⁺

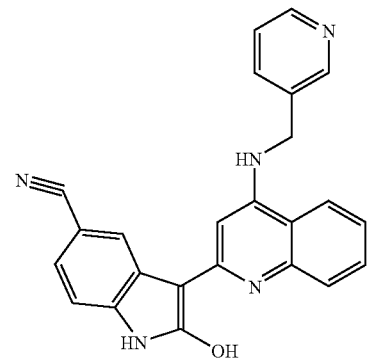

2-Hydroxy-3-{4-[(pyridin-3-ylmethyl)-amino]-quinolin-2-yl}-1H-indole-5-carbonitrile: ESI-MS: m/z 392.2 (M+H)⁺

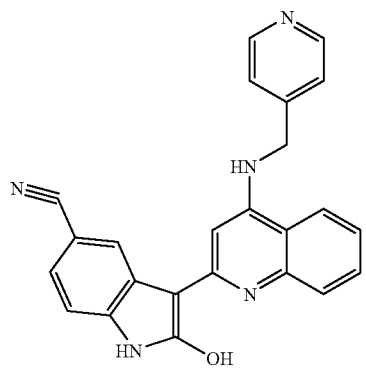

2-Hydroxy-3-{4-[(pyridin-4-ylmethyl)-amino]-quinolin-2-yl}-1H-indole-5-carbonitrile: ESI-MS: m/z 392.2 (M+H)⁺

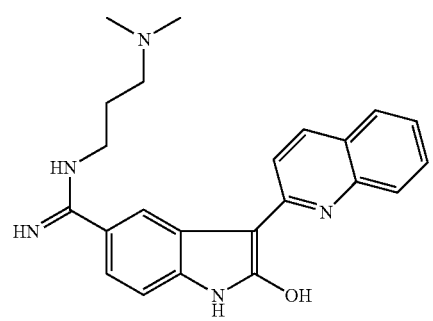

N-(3-Dimethylamino-propyl)-2-hydroxy-3-quinolin-2-yl-1H-indole-5-carboxamidine: ESI-MS: m/z 388.1 (M+H)⁺

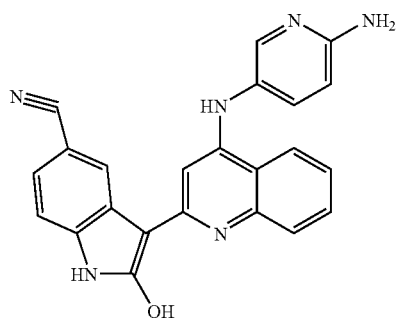

3-[4-(6-Amino-pyridin-3-ylamino)-quinolin-2-yl]-2-hydroxy-1H-indole-5-carbonitrile: ESI-MS: m/z 393.2 (M+H)+

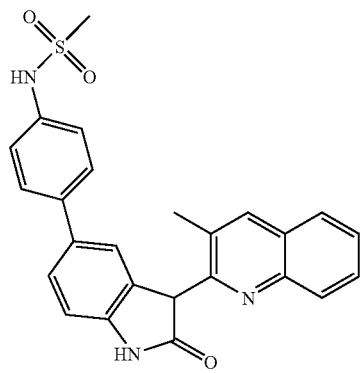

N-{4-[3-(3-Methyl-quinolin-2-yl)-2-oxo-2,3-dihydro-1H-indol-5-yl]-phenyl}-methanesulfonamide: $^1$H NMR (400 MHz, DMSO-D6) δ ppm 2.49 (s, 3H) 2.93 (s, 3H) 5.39 (s, 1H) 7.01 (d, J=8.08 Hz, 1H) 7.18 (m, 3H) 7.45-7.56 (m, 4H) 7.64 (t, J=7.58 Hz, 1H) 7.80-7.90 (m, 2H) 8.18 (s, 1H) 9.65 (s, 1H) 10.68 (s, 1H); ESI-MS: m/z 444.0 (M+H)+

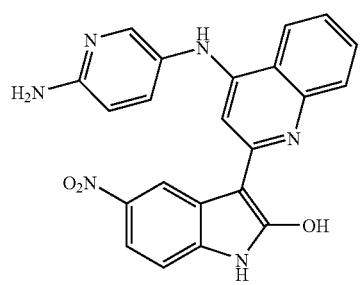

3-[4-(6-Amino-pyridin-3-ylamino)-quinolin-2-yl]-5-nitro-1H-indol-2-ol: ESI-MS: m/z 413.4 (M+H)+

N-{3-[3-(3-Methyl-quinolin-2-yl)-2-oxo-2,3-dihydro-1H-indol-5-yl]-phenyl}-methanesulfonamide: $^1$H NMR (400 MHz, DMSO-D6) δ ppm 2.49 (s, 3H) 2.93 (s, 3H) 5.43 (s, 1H) 7.04 (d, J=8.08 Hz, 1H) 7.09-7.14 (m, 1H) 7.17 (s, 1H) 7.22-7.32 (m, 3H) 7.48-7.57 (m, 2H) 7.61-7.67 (m, 1H) 7.81-7.90 (m, 2H) 8.19 (s, 1H) 9.61 (s, 1H) 10.72 (s, 1H); ESI-MS: m/z 444.0 (M+H)+

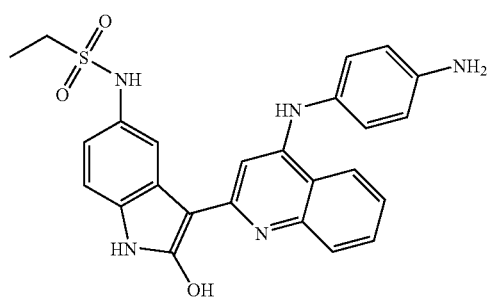

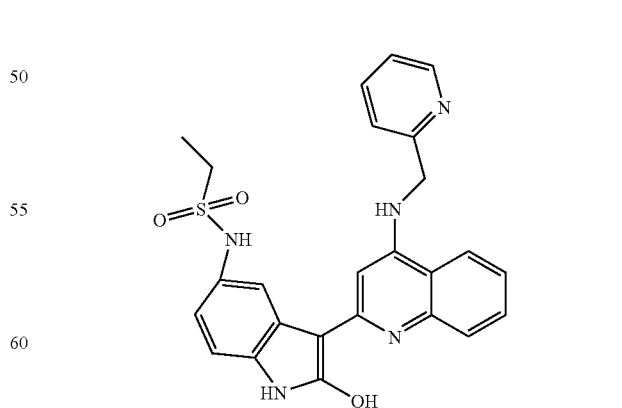

Ethanesulfonic acid {3-[4-(4-amino-phenylamino)-quinolin-2-yl]-2-hydroxy-1H-indol-5-yl}-amide: ESI-MS: m/z 474.2 (M+H)+

Ethanesulfonic acid (2-hydroxy-3-{4-[(pyridin-2-ylmethyl)-amino]-quinolin-2-yl}-1H-indol-5-yl)-amide: ESI-MS: m/z 474.2 (M+H)+

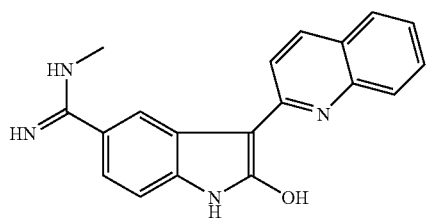

2-Hydroxy-N-methyl-3-quinolin-2-yl-1H-indole-5-carboxamidine: ESI-MS: m/z 317 (M+H)+

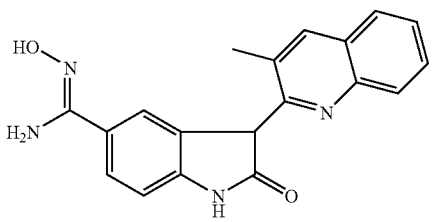

N-Hydroxy-3-(3-methyl-quinolin-2-yl)-2-oxo-2,3-dihydro-1H-indole-5-carboxamidine: ESI-MS: m/z 333 (M+H)+

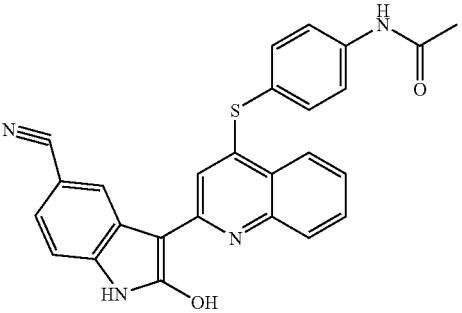

N-{4-[2-(5-Cyano-2-hydroxy-1H-indol-3-yl)-quinolin-4-yl-sulfanyl]-phenyl}-acetamide: ESI-MS: m/z 451.3 (M+H)+

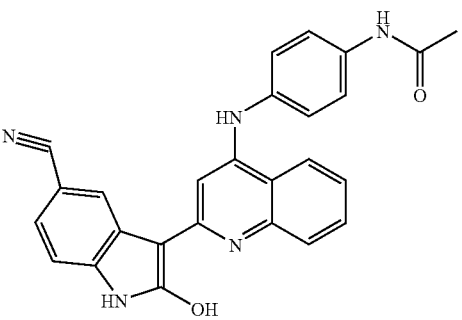

N-{4-[2-(5-Cyano-2-hydroxy-1H-indol-3-yl)-quinolin-4-ylamino]-phenyl}-acetamide: ESI-MS: m/z 434.3 (M+H)+

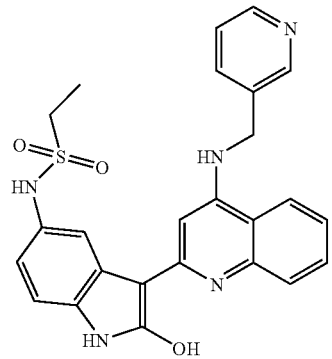

Ethanesulfonic acid (2-hydroxy-3-{4-[(pyridin-3-ylmethyl)-amino]-quinolin-2-yl}-1H-indol-5-yl)-amide: ESI-MS: m/z 474.2 (M+H)+

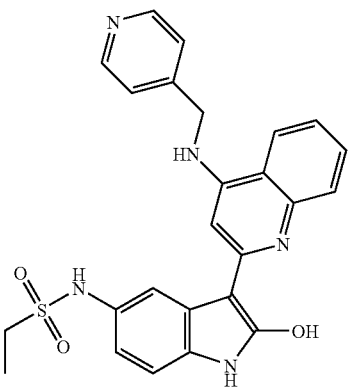

Ethanesulfonic acid (2-hydroxy-3-{4-[(pyridin-3-ylmethyl)-amino]-quinolin-2-yl}-1H-indol-5-yl)-amide: ESI-MS: m/z 474.2 (M+H)+

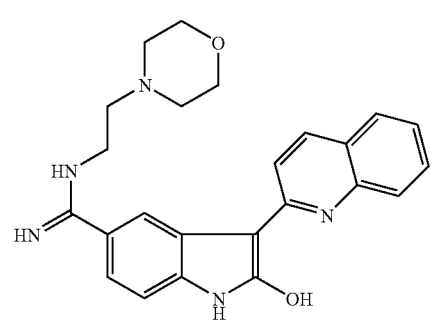

2-Hydroxy-N-(2-morpholin-4-yl-ethyl)-3-quinolin-2-yl-1H-indole-5-carboxamidine: ESI-MS: m/z 416.1 (M+H)+

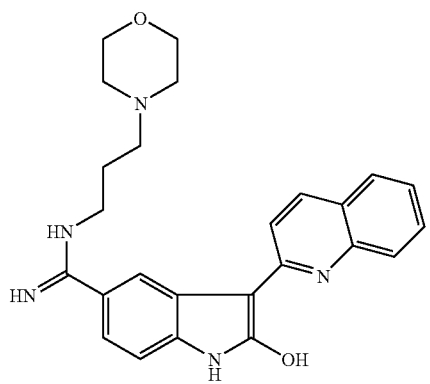

2-Hydroxy-N-(3-morpholin-4-yl-propyl)-3-quinolin-2-yl-1H-indole-5-carboxamidine: ESI-MS: m/z 430.1 (M+H)+

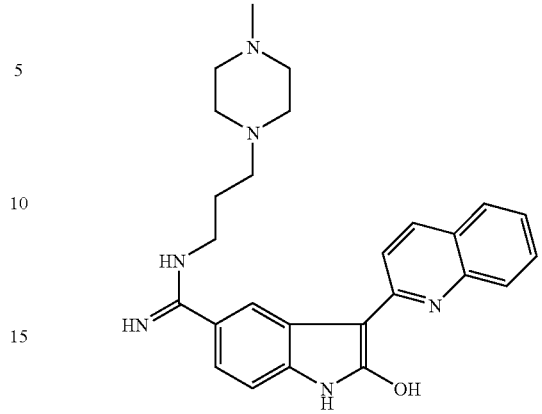

2-Hydroxy-N-[3-(4-methyl-piperazin-1-yl)-propyl]-3-quinolin-2-yl-1H-indole-5-carboxamidine: ESI-MS: z/z 443.1 (M+H)+

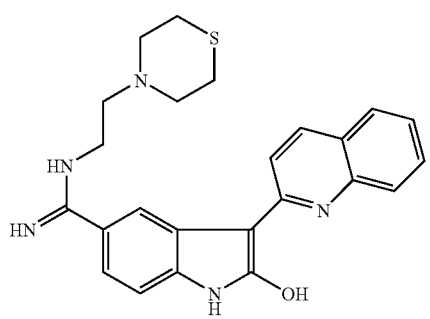

2-Hydroxy-3-quinolin-2-yl-N-(2-thiomorpholin-4-yl-ethyl)-1H-indole-5-carboxamidine: ESI-MS: m/z 432 (M+H)+

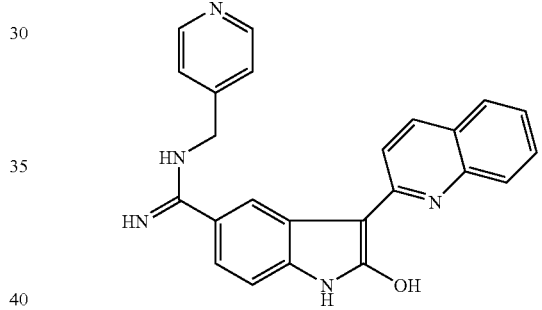

2-Hydroxy-N-pyridin-4-ylmethyl-3-quinolin-2-yl-1H-indole-5-carboxamidine: ESI-MS: m/z 394 (M+H)+

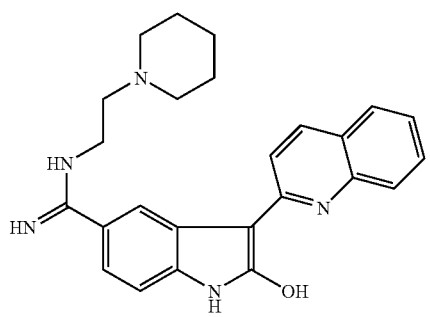

2-Hydroxy-N-(2-piperidin-1-yl-ethyl)-3-quinolin-2-yl-1H-indole-5-carboxamidine: ESI-MS: m/z 414.1 (M+H)+

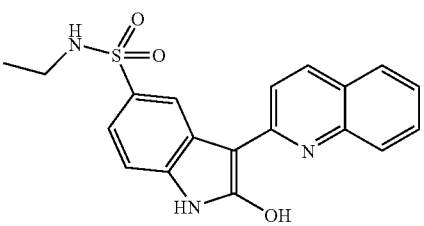

2-Hydroxy-3-quinolin-2-yl-1H-indole-5-sulfonic acid ethylamide: $^1$H NMR (400 MHz, DMSO-D6) δ ppm 0.97 (t, J=7.20 Hz, 3H) 2.70-2.78 (m, 2H) 7.05 (d, J=8.34 Hz, 1H) 7.31 (t, J=5.68 Hz, 1H) 7.35-7.40 (m, 1H) 7.42 (dd, J=8.21, 1.39 Hz, 1H) 7.63-7.73 (m, 2H) 7.83 (d, J=7.83 Hz, 1H) 7.95 (s, 1H) 8.26 (d, J=9.35 Hz, 1H) 11.05 (s, 1H) 14.45 (s, 1H); ESI-MS: m/z 368.0 (M+H)+

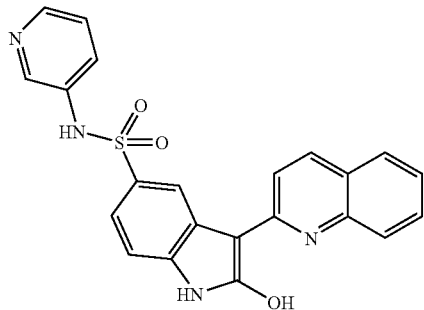

2-Hydroxy-3-quinolin-2-yl-1H-indole-5-sulfonic acid pyridin-3-ylamide: $^1$H NMR (400 MHz, DMSO-D6) δ ppm 6.99 (d, J=8.34 Hz, 1H) 7.27 (dd, J=8.34, 4.80 Hz, 1H) 7.35-7.42 (m, 2H) 7.54-7.62 (m, 2H) 7.64-7.71 (m, 2H) 7.85 (d, J=7.83 Hz, 1H) 7.92 (s, 1H) 8.20 (d, J=4.55 Hz, 1H) 8.27-8.33 (m, 2H) 10.34 (s, 1H) 11.08 (s, 1H) 14.41 (s, 1H); ESI-MS: m/z 417.0 (M+H)$^+$

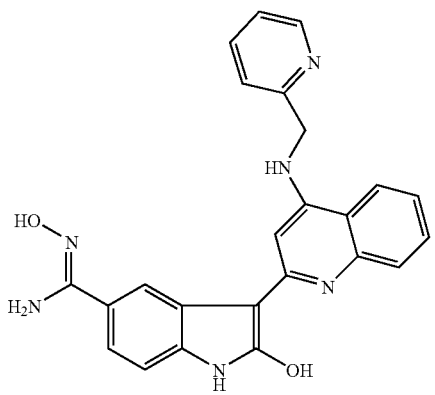

2,N-Dihydroxy-3-{4-[(pyridin-4-ylmethyl)-amino]-quinolin-2-yl}-1H-indole-5-carboxamidine: ESI-MS: m/z 425 (M+H)$^+$

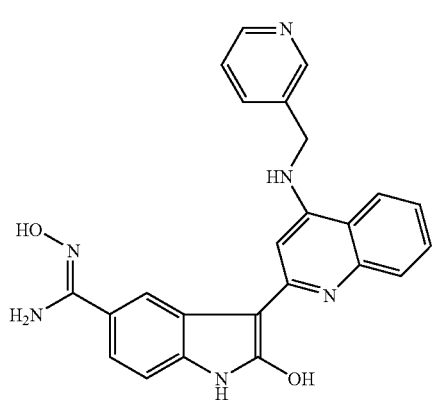

2,N-Dihydroxy-3-{4-[(pyridin-3-ylmethyl)-amino]-quinolin-2-yl}-1H-indole-5-carboxamidine: ESI-MS: m/z 425 (M+H)$^+$

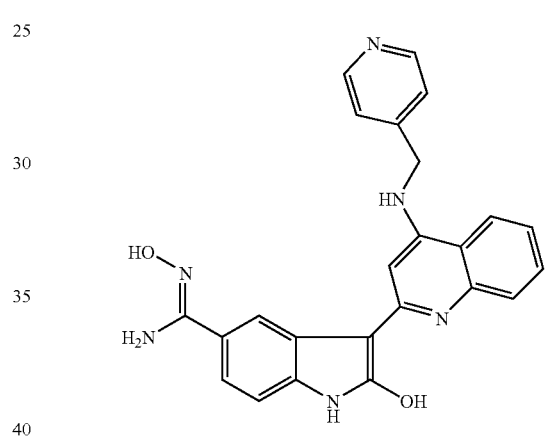

2,N-Dihydroxy-3-{4-[(pyridin-4-ylmethyl)-amino]-quinolin-2-yl}-1H-indole-5-carboxamidine: ESI-MS: m/z 425 (M+H)$^+$

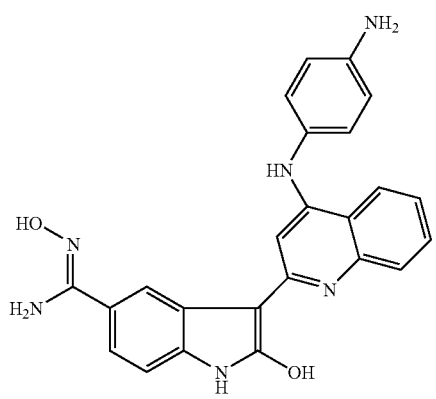

3-[4-(4-Amino-phenylamino)-quinolin-2-yl]-2,N-dihydroxy-1H-indole-5-carboxamidine: ESI-MS: m/z 425 (M+H)$^+$

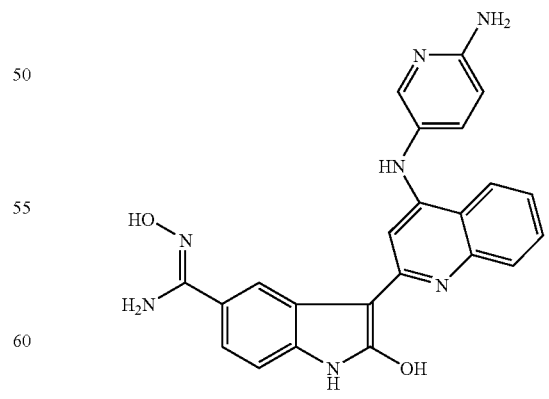

3-[4-(6-Amino-pyridin-3-ylamino)-quinolin-2-yl]-2,N-dihydroxy-1H-indole-5-carboxamidine: ESI-MS: m/z 426 (M+H)$^+$

101

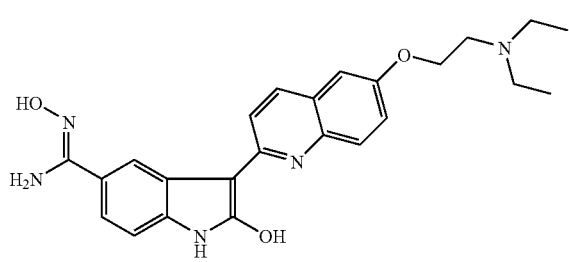

3-[6-(2-Diethylamino-ethoxy)-quinolin-2-yl]-1H-indole-5-carboxamidine: ESI-MS: m/z 434.1 (M+H)$^+$

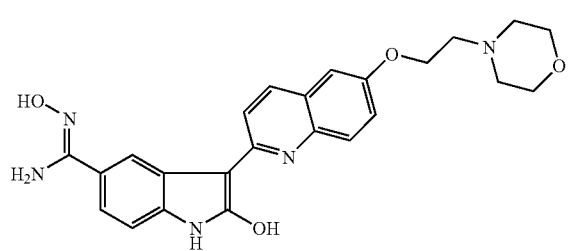

2,N-Dihydroxy-3-[6-(2-morpholin-4-yl-ethoxy)-quinolin-2-yl]-1H-indole-5-carboxamidine: ESI-MS: m/z 448 (M+H)$^+$

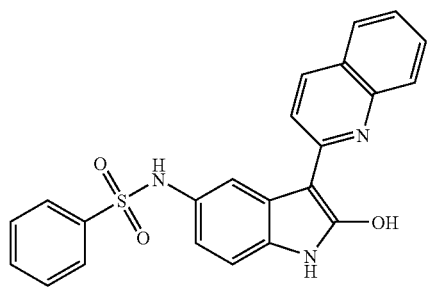

N-(2-Hydroxy-3-quinolin-2-yl-1H-indol-5-yl)-benzene-sulfonamide: ESI-MS: m/z 416.2 (M+H)$^+$

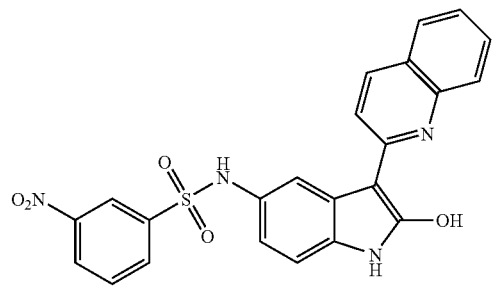

N-(2-Hydroxy-3-quinolin-2-yl-1H-indol-5-yl)-benzene-sulfonamide: ESI-MS: m/z 461.2 (M+H)$^+$

102

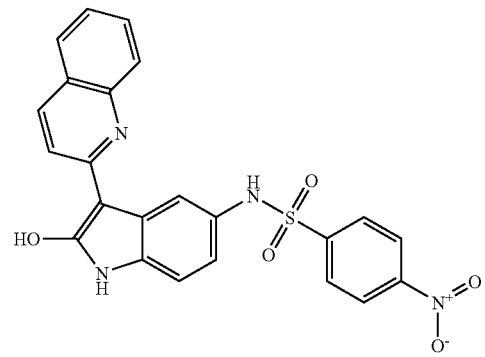

N-(2-Hydroxy-3-quinolin-2-yl-1H-indol-5-yl)-4-nitro-benzenesulfonamide: ESI-MS: 7 m/z 461.2 (M+H)$^+$

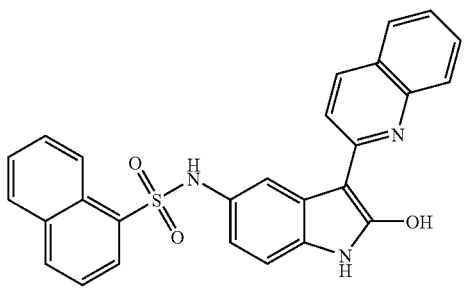

Naphthalene-1-sulfonic acid (2-hydroxy-3-quinolin-2-yl-1H-indol-5-yl)-amide: ESI-MS: m/z 466.2 (M+H)$^+$

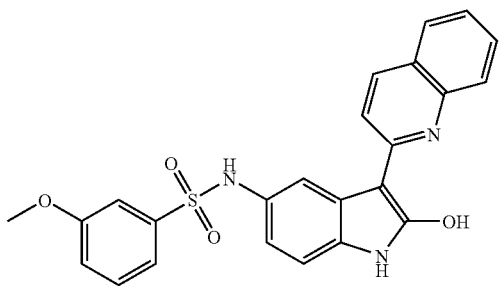

N-(2-Hydroxy-3-quinolin-2-yl-1H-indol-5-yl)-3-methoxy-benzenesulfonamide: ESI-MS: m/z 446.2 (M+H)$^+$

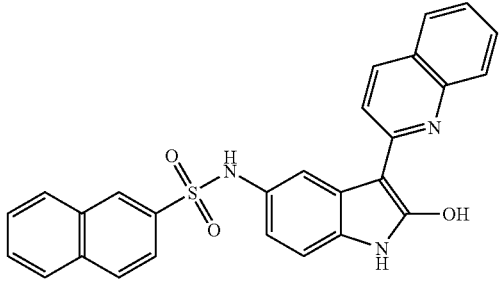

Naphthalene-2-sulfonic acid (2-hydroxy-3-quinolin-2-yl-1H-indol-5-yl)-amide: ESI-MS: m/z 466.2 (M+H)⁺

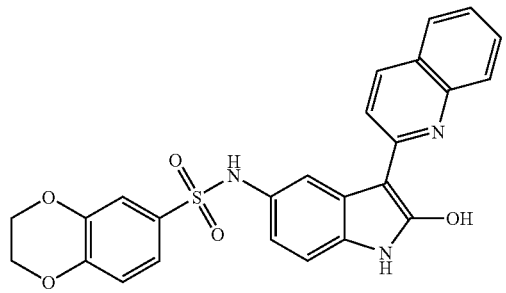

2,3-Dihydro-benzo[1,4]dioxine-6-sulfonic acid (2-hydroxy-3-quinolin-2-yl-1H-indol-5-yl)-amide: ESI-MS: m/z 474.2 (M+H)⁺

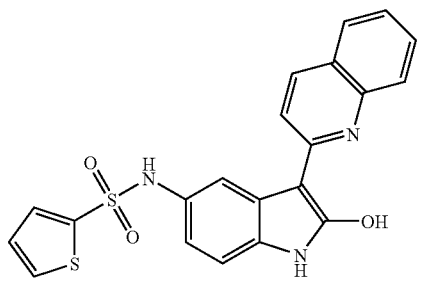

Thiophene-2-sulfonic acid (2-hydroxy-3-quinolin-2-yl-1H-indol-5-yl)-amide: ESI-MS: m/z 422.2 (M+H)⁺

N-(2-Hydroxy-3-quinolin-2-yl-1H-indol-5-yl)-3-methyl-benzenesulfonamide: ESI-MS: m/z 430.2 (M+H)⁺

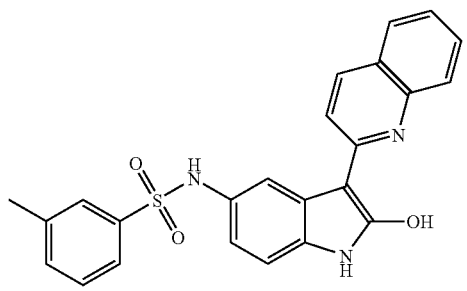

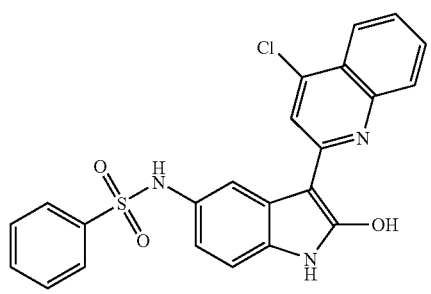

N-[3-(4-Chloro-quinolin-2-yl)-2-hydroxy-1H-indol-5-yl]-benzenesulfonamide: ESI-MS: m/z 450.1 (M+H)⁺

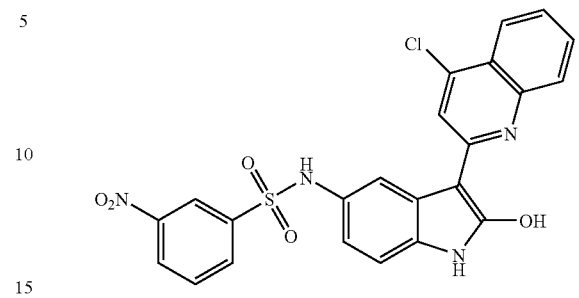

N-[3-(4-Chloro-quinolin-2-yl)-2-hydroxy-1H-indol-5-yl]-3-nitro-benzenesulfonamide: ESI-MS: m/z 495.1 (M+H)⁺

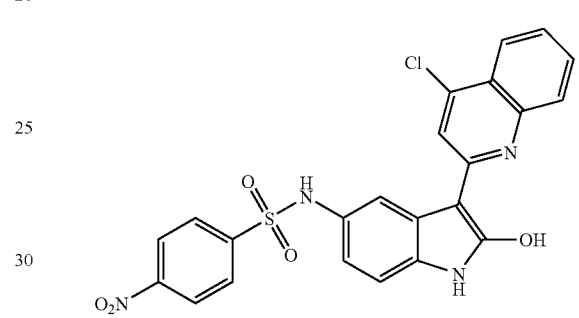

N-[3-(4-Chloro-quinolin-2-yl)-2-hydroxy-1H-indol-5-yl]-4-nitro-benzenesulfonamide: ESI-MS: m/z 495.1 (M+H)⁺

Naphthalene-1-sulfonic acid [3-(4-chloro-quinolin-2-yl)-2-hydroxy-1H-indol-5-yl]-amide: ESI-MS: m/z 500.1 (M+H)⁺

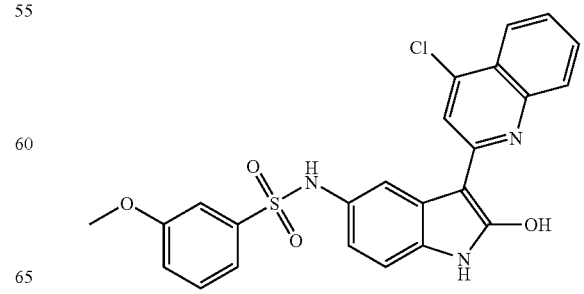

105

N-[3-(4-Chloro-quinolin-2-yl)-2-hydroxy-1H-indol-5-yl]-3-methoxy-benzenesulfonamide: ESI-MS: m/z 480.1 (M+H)+

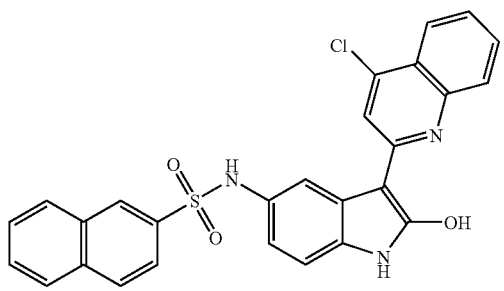

Naphthalene-2-sulfonic acid [3-(4-chloro-quinolin-2-yl)-2-hydroxy-1H-indol-5-yl]-amide: ESI-MS: m/z 500.1 (M+H)+

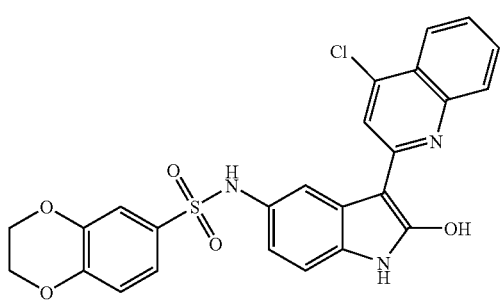

2,3-Dihydro-benzo[1,4]dioxine-6-sulfonic acid [3-(4-chloro-quinolin-2-yl)-2-hydroxy-1H-indol-5-yl]-amide: ESI-MS: m/z 508.1 (M+H)+ ESI-MS: m/z 464.1 (M+H)+

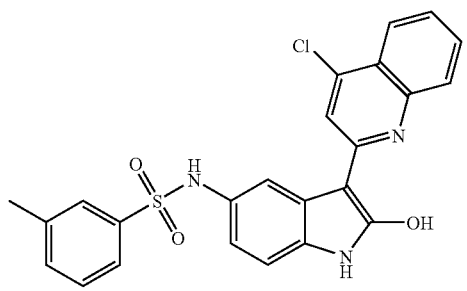

N-[3-(4-Chloro-quinolin-2-yl)-2-hydroxy-1H-indol-5-yl]-3-methyl-benzenesulfonamide: ESI-MS: m/z 464.1 (M+H)+

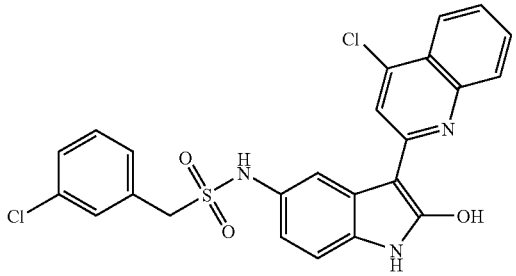

106

C—(3-Chloro-phenyl)-N-[3-(4-chloro-quinolin-2-yl)-2-hydroxy-1H-indol-5-yl]-methanesulfonamide: ESI-MS: m/z 498.1 (M+H)+

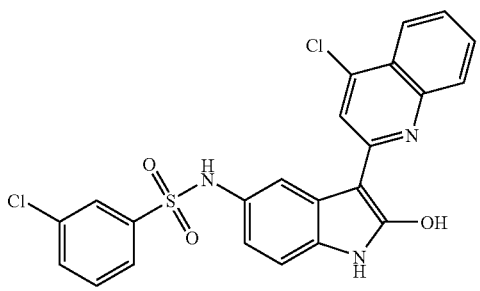

3-Chloro-N-[3-(4-chloro-quinolin-2-yl)-2-hydroxy-1H-indol-5-yl]-benzenesulfonamide: ESI-MS: m/z 484.1 (M+H)+

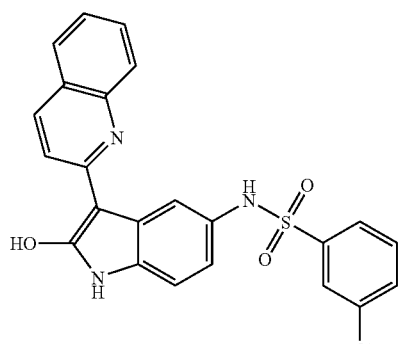

3-Chloro-N-(2-hydroxy-3-quinolin-2-yl-1H-indol-5-yl)-benzenesulfonamide: ESI-MS: m/z 450.1 (M+H)+

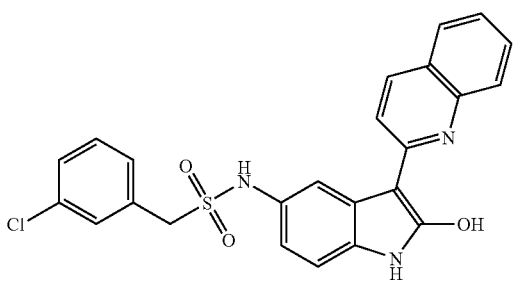

C—(3-Chloro-phenyl)-N-(2-hydroxy-3-quinolin-2-yl-1H-indol-5-yl)-methanesulfonamide-ESI-MS: m/z 464.1 (M+H)+

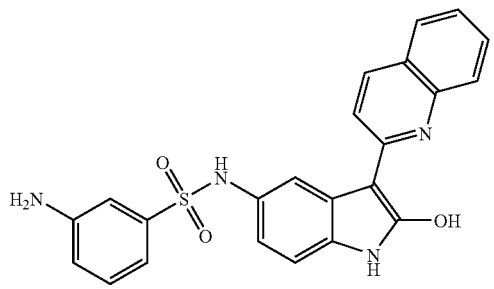

3-Amino-N-(2-hydroxy-3-quinolin-2-yl-1H-indol-5-yl)-benzenesulfonamide: ESI-MS: m/z 431.2 (M+H)+

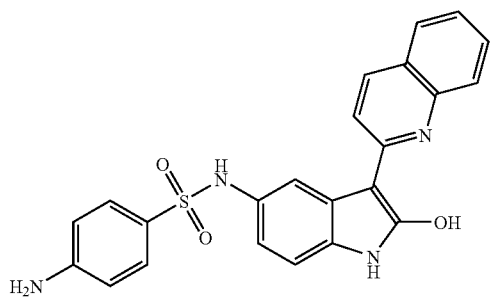

4-Amino-N-(2-hydroxy-3-quinolin-2-yl-1H-indol-5-yl)-benzenesulfonamide: ESI-MS: m/z 431.2 (M+H)+

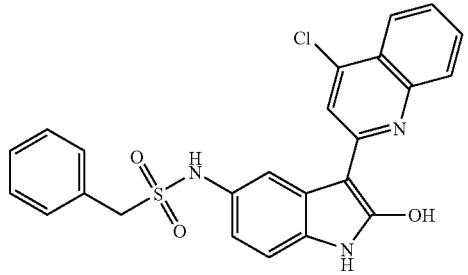

N-[3-(4-Chloro-quinolin-2-yl)-2-hydroxy-1H-indol-5-yl]-C-phenyl-methanesulfonamide: ESI-MS: m/z 464.1 (M+H)+

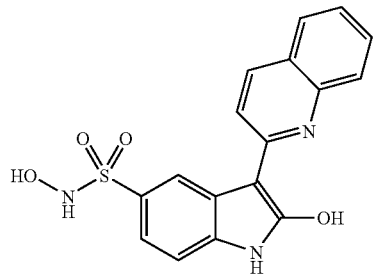

2-Hydroxy-3-quinolin-2-yl-1H-indole-5-sulfonic acid hydroxyamide: ESI-MS: m/z 356.2 (M+H)+

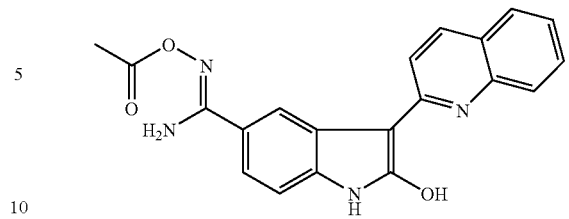

2,N-Dihydroxy-3-quinolin-2-yl-1H-indole-5-carboxamidine-O-acetyl: ESI-MS: m/z 301 (M+H)+

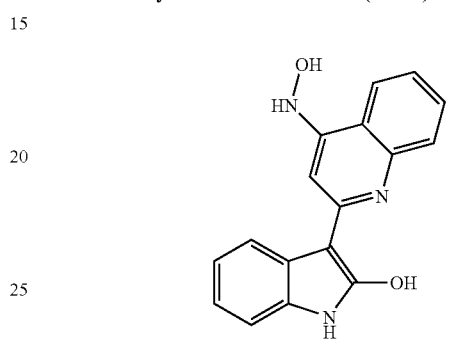

3-(4-Hydroxyamino-quinolin-2-yl)-1H-indol-2-ol: ESI-MS: m/z 292.4 (M+H)+

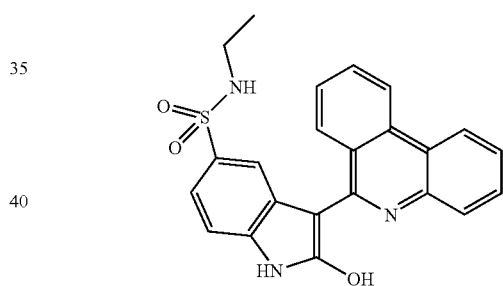

2-Hydroxy-3-phenanthridin-6-yl-1H-indole-5-sulfonic acid ethylamide: ESI-MS: m/z 418.2 (M+H)+

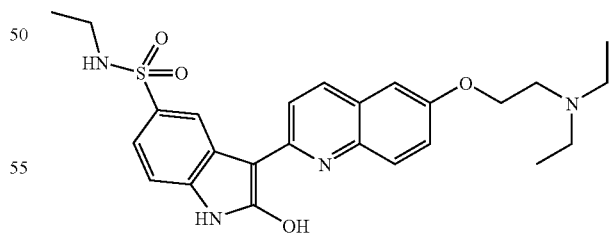

3-[6-(2-Diethylamino-ethoxy)-quinolin-2-yl]-2-hydroxy-1H-indole-5-sulfonic acid ethylamide: $^1$H NMR (400 MHz, DMSO-D6) δ ppm 0.98 (t, J=7.20 Hz, 3H) 1.25-(t, J=7.33 Hz, 6H) 2.75 (dt, J=13.07, 7.11 Hz, 2H) 3.59-3.60 (m, 2H) 4.38-4.46 (m, 2H) 7.05 (d, J=8.34 Hz, 1H) 7.25 (t, J=5.68 Hz, 1H) 7.36-7.44 (m, 2H) 7.47 (d, J=2.53 Hz, 1H) 7.67-7.78 (m, 2H) 7.94 (s, 1H) 8.23 (d, J=9.60 Hz, 1H) 9.28 (s, 1H) 10.97 (s, 1H) 14.56 (s, 1H); ESI-MS: m/z 483.3 (M+H)+

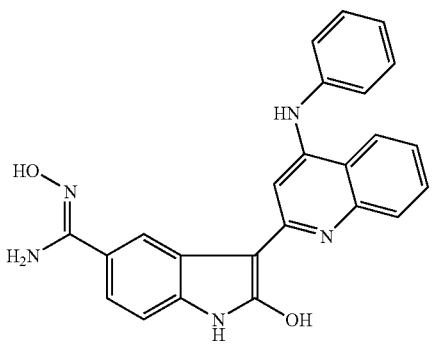

2,N-Dihydroxy-3-(4-phenylamino-quinolin-2-yl)-1H-indole-5-carboxamidine: ESI-MS: m/z 410.3 (M+H)$^+$

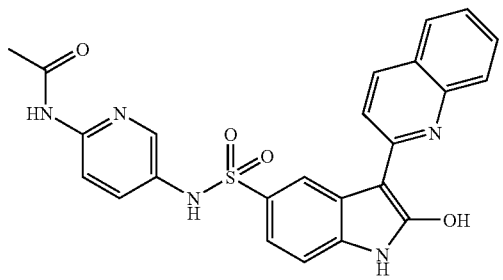

N-[5-(2-Hydroxy-3-quinolin-2-yl-1H-indole-5-sulfonylamino)-pyridin-2-yl]-acetamide: ESI-MS: m/z 474.5 (M+H)$^+$

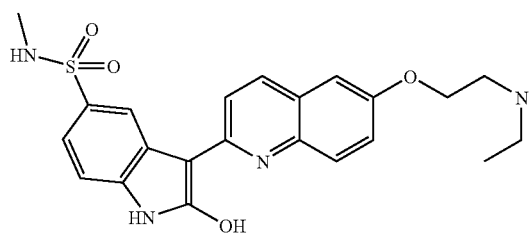

3-[6-(2-Diethylamino-ethoxy)-quinolin-2-yl]-2-hydroxy-1H-indole-5-sulfonic acid methylamide: $^1$H NMR (400 MHz, DMSO-D6) δ ppm 1.26 (t, J=7.20 Hz, 6H) 2.39 (d, J=4.04 Hz, 3H) 3.20-3.31 (m, 4H) 3.58 (q, J=4.63 Hz, 2H) 4.39-4.46 (m, 2H) 7.06 (d, J=8.08 Hz, 1H) 7.16 (d, J=4.80 Hz, 1H) 7.37-7.42 (m, 2H) 7.47 (d, J=2.53 Hz, 1H) 7.70 (d, J=8.84 Hz, 1 H) 7.75 (d, J=9.60 Hz, 1H) 7.92 (s, 1H) 8.22 (d, J=9.60 Hz, 1H) 9.43 (s, 1H) 10.98 (s, 1H) 14.55 (s, 1H); ESI-MS: m/z 469.3 (M+H)$^+$

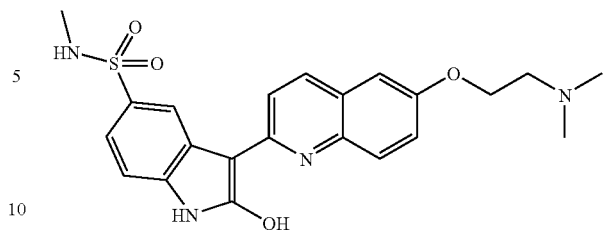

3-[6-(2-Dimethylamino-ethoxy)-quinolin-2-yl]-2-hydroxy-1H-indole-5-sulfonic acid methylamide: $^1$H NMR (400 MHz, DMSO-D6) δ ppm 2.39 (d, J=5.05 Hz, 3H) 2.89 (s, 6H) 3.53-3.61 (m, 2H)439-4.48(m, 2H)7.06(d, J=8.08 Hz, 1H) 4.39-4.48 (m, 2H) 7.06 (d, J=8.08 Hz, 1H)7.36-7.43 (m, 2H) 7.47 (d, J=2.78 Hz, 1H) 7.67-7.78 (m, 2H) 7.92 (s, 1H) 8.22 (d, J=9.35 Hz, 1H) 9.77 (s, 1H) 10.98 (s, 1H); ESI-MS: m/z 441.3 (M+H)$^+$

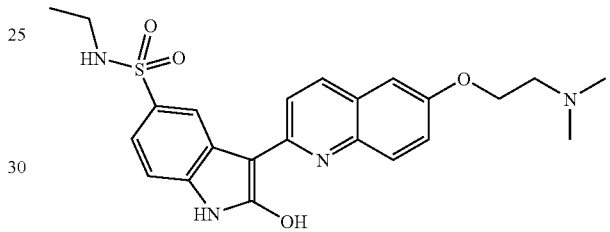

3-[6-(2-Dimethylamino-ethoxy)-quinolin-2-yl]-2-hydroxy-1H-indole-5-sulfonic acid ethylamide: $^1$H NMR (400 MHz, DMSO-D6) δ ppm 0.98 (t, J=7.20 Hz, 3H) 2.71-2.79 (m, 2H) 2.89 (s, 6H) 3.54-3.61 (m, 2H) 4.40-4.46 (m, 2H) 7.05 (d, J=8.08 Hz, 1H) 7.25 (t, J=5.81 Hz, 1H) 7.40 (td, J=8.27, 2.15 Hz, 2H) 7.47 (d, J=2.78 Hz, 1H) 7.67-7.78 (m, 2H) 7.94 (s, 1H) 8.22 (d, J=9.35 Hz, 1H) 9.73 (s, 1H) 10.97 (s, 1H); ESI-MS: m/z 455.3 (M+H)$^+$

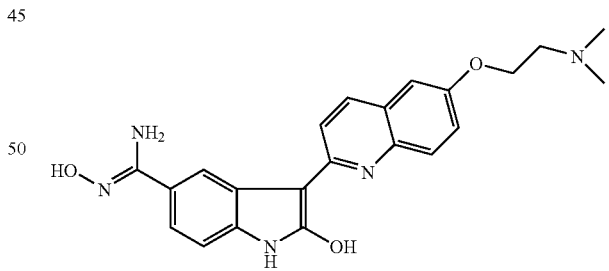

3-[6-(2-Dimethylamino-ethoxy)-quinolin-2-yl]-2,N-dihydroxy-1H-indole-5-carboxamidine: ESI-MS: m/z 406.3 (M+H)$^+$ It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:
1. A compound comprising the formula:

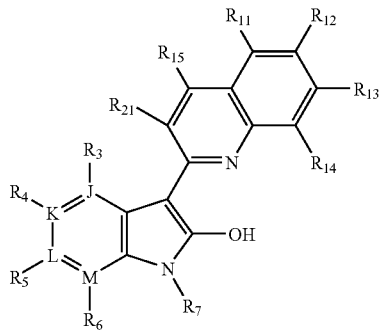

wherein:
- $R_3$, $R_4$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_4$, $R_5$, and $R_6$ are taken together to form a ring, with the proviso that $R_3$, $R_4$, $R_5$, and $R_6$ are absent where the ring atom to which $R_3$, $R_4$, $R_5$, and $R_6$ are bound is nitrogen;
- $R_7$ is hydrogen or a substituent convertible in vivo to hydrogen;
- $R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;
- J, K, L and M are each C;
- $R_{15}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted; and
- $R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{20}$ and $R_{15}$ are taken together to form a ring, with the proviso that at least one of $R_3$, $R_4$, $R_5$, and $R_6$ is selected from the group consisting of —$NH_2$, furanyl, quinolinyl, indolyl, pyridinyl, carboxamidinyl, aminosulfonyl, and arylalkyl, each unsubstituted or substituted, or a substituted sulfonamidyl, or $R_{15}$ is an N-linked moiety; or $R_{15}$ is an S-linked moiety.

2. The compound according to claim 1, wherein $R_{15}$ is an N-linked moiety.

3. The compound according to claim 1, wherein $R_{15}$ is an S-linked moiety.

4. The compound according to claim 1, wherein $R_{15}$ is an unsubstituted or substituted amino.

5. A compound comprising the formula:

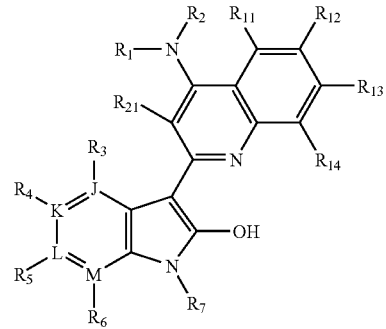

wherein:
- $R_1$ and $R_2$ are selected from the group consisting of hydrogen, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;
- $R_3$, $R_4$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_4$, $R_5$, and $R_6$ are taken together to form a ring, with the proviso that $R_3$, $R_4$, $R_5$, and $R_6$ are absent where the ring atom to which $R_3$, $R_4$, $R_5$, and $R_6$ are bound is nitrogen;
- $R_7$ is hydrogen or a substituent convertible in vivo to hydrogen;
- $R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

J, K, L and M are each C; and $R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{21}$ and $R_1$ are taken together to form a ring.

6. The compound according to claim 5, wherein at least one of $R_4$ and $R_5$ is not H.

7. The compound according to claim 5, wherein $R_{14}$ is hydrogen.

8. The compound according to claim 5, wherein two of J, K, L and M are taken together to form a further ring that is fused to the ring comprising J, K, L and M.

9. The compound according to claim 8, wherein the fused ring is a substituted or unsubstituted 5 or 6 membered aryl or heteroaryl ring.

10. The compound according to claim 8, wherein the fused ring is an alicyclic ring.

11. The compound according to claim 5, wherein $R_{21}$ is H.

12. The compound according to claim 5, wherein the ring formed by J, K, L and M comprises substituents that form a ring fused to the ring formed by J, K, L and M.

13. The compound according to claim 5, wherein $R_{11}$, $R_{12}$, $R_{13}$ and $R_{14}$ are each independently selected from the group consisting of hydrogen, F, Br, Cl, —$OCH_3$, —$SO_2Me$, —$SO_2NH_2$, —$SO_2NHMe$, —$SO_2NHCH_2CH_2OH$, —$SO_2NMe_2$, —$NHSO_2$(3-fluorophenyl), perhalo($C_{1-10}$) alkyl, —$OCF_3$, —$CF_3$, ($C_{1-10}$)alkyl, hydroxy-($C_{1-10}$)alkyl, aryl, aryl-($C_{1-10}$)alkyl, heteroaryl, aminosulfonyl, alkylsulfonyl, arylsulfonyl, heteroarylsulfonyl, hydroxy, aryloxy, heteroaryloxy, arylalkyl, heteroaryl($C_{1-10}$)alkyl, cycloalkyl, heterocycloalkyl, HS—, ($C_{1-6}$)alkylS-, cyano, nitro, cycloalkoxy, ($C_{1-12}$)alkoxy, —COOH, —$CO_2Me$, carboxamide, ($C_{1-12}$)alkylNHCO—, $R_9R_{10}N$—($C_{1-12}$)alkyl aminocarbonyl, $R_9R_{10}N$—($C_{1-12}$)alkoxycarbonyl, hetero-($C_{1-6}$)alkylaminocarbonyl, heterocycloalkyl-($C_{1-6}$)alkylCO—, heteroaryl-($C_{1-6}$)alkylCO—, heterocycloalkyl-($C_{1-6}$)alkylOCO—, heteroaryl-($C_{1-6}$)alkylOCO—, ($C_{1-6}$)alkylOCO—, diethoxyphosphorylmethyl, imino group, $R_9R_{10}N$—($C_{1-6}$) alkylsulfonyl, —$NH_2$, —$NHCH_3$, —$N(CH_3)_2$, —$NH(C_{1-3})$ alkyl, —$N(C_{1-3}$-alkyl$)_2$, $R_9R_{10}N$—($C_{1-12}$)alkyl aminocarbonylamino, $R_9R_{10}N$—($C_{1-6}$)alkyl alkoxycarbonylamino, heterocycloalkyl-($C_{1-6}$)alkyl aminocarbonylamino, heteroaryl-($C_{1-6}$)alkyl aminocarbonylamino, ($C_{3-12}$)heterocycloalkyl-($C_{1-6}$)alkoxycarbonylamino, heteroaryl-($C_{1-6}$) alkoxycarbonylamino, ($C_{1-6}$)alkyl carbonylamino, (($C_{1-6}$) alkyl carbonyl)($C_{1-6}$ alkyl)amino, $R_9R_{10}N$—($C_{1-6}$)alkyl carbonylamino, [$R_9R_{10}N$—($C_{1-6}$)alkylcarbonyl][($C_{1-6}$) alkyl]amino, $R_9R_{10}N$—($C_{1-6}$)alkyl sulfonylamino, [$R_9R_{10}N$—($C_{1-6}$)alkylsulfonyl][($C_{1-6}$)alkyl]amino, and —$NR_9R_{10}$ where $R_9$ and $R_{10}$ are independently selected from the group consisting of hydrogen, ($C_{1-6}$)alkyl, heterocycloalkyl, aryl and heteroaryl, each substituted or unsubstituted, or where $R_9$ and $R_{10}$ together are —$(CH_2)_{4-5}$— optionally interrupted by one O, S, NH or —N($C_{1-3}$)alkyl group, or where $R_9$ and $R_{10}$ together is selected from the group consisting of pyrrolidin-1-yl, morpholin-4-yl, and 4-methyl-piperazin-1-yl, each unsubstituted or substituted.

14. The compound according to claim 5, wherein $R_{11}$ and $R_{12}$, or $R_{12}$ and $R_{13}$, or $R_{13}$ and $R_{14}$ are taken together to form a substituted or unsubstituted fused ring.

15. The compound according to claim 14, wherein the fused ring is a substituted or unsubstituted 5 or 6 membered aryl or heteroaryl ring.

16. The compound according to claim 14, wherein the fused ring is a substituted or unsubstituted fused alicyclic ring.

17. The compound according to claim 5, wherein $R_4$ and $R_5$ are each independently selected from the group consisting of hydrogen, amino, cyano, ($C_{1-6}$)alkyl, ($C_{1-6}$)alkoxy, hydroxy-($C_{1-6}$)alkyl, ($C_{1-10}$)alkoxycarbonyl, aryl, heterocyclyl, heteroaryl, aminocarbonyl, ($C_{1-6}$)alkyl aminocarbonyl, halogen and hydroxy, each substituted or unsubstituted.

18. The compound according to claim 5, wherein $R_4$ is selected from the group consisting of 2-furanyl, 3-thienyl, Br, hydrogen, cyano, 4-acetamidophenyl, and phenyl.

19. The compound according to claim 5, wherein $R_3$ and $R_4$ are taken together to form a substituted or unsubstituted fused ring.

20. The compound according to claim 19, wherein $R_3$ and $R_4$ are together selected from the group consisting of —NH—CH=N—, —NH—N=N—, —S—CH=N—, and —CH=CH—CH=N—.

21. The compound according to claim 5, wherein $R_5$ is selected from the group consisting of hydrogen, amino, ($C_{1-6}$)alkyl, ($C_{1-6}$)alkenyl, and phenyl, each substituted or unsubstituted.

22. The compound according to claim 5, wherein $R_5$ is selected from the group consisting of methyl, 2-furanyl, 2-thienyl, CH=$CH_2$, hydrogen and phenyl.

23. A compound comprising the formula:

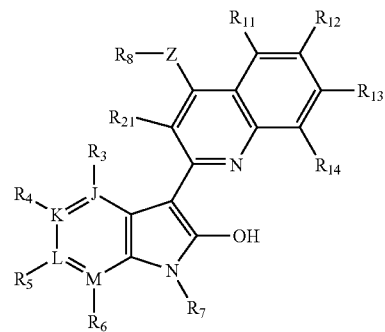

wherein:

$R_3$, $R_4$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$) alkyl, heteroaryl($C_{1-5}$)alkyl, ($C_{9-12}$)bicycloaryl, hetero ($C_{4-12}$)bicycloaryl, carbonyl($C_{1-3}$)alkyl, thiocarbonyl ($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_4$, $R_5$, and $R_6$ are taken together to form a ring, with the proviso that $R_3$, $R_4$, $R_5$, and $R_6$ are absent where the ring atom to which $R_3$, $R_4$, $R_5$, and $R_6$ are bound is nitrogen;

$R_7$ is hydrogen or a substituent convertible in vivo to hydrogen;

$R_8$ is selected from the group consisting of hydrogen, alkoxy, aryloxy, heteroaryloxy, carbonyl, amino, $(C_{1-10})$alkylamino, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{11}$, $R_{12}$, $R_{13}$, and $R_{14}$ are each independently selected from the group consisting of hydrogen, $(C_{1-12})$alkyl, alkoxy, thio, hydroxy, $(C_{3-12})$cycloalkyl, hetero$(C_{3-12})$cycloalkyl, hetero$(C_{3-12})$cycloalkoxy, $(C_{9-12})$bicycloaryl, hetero$(C_{8-12})$bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

J, K, L and M are C;

$R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_8$ are taken together to form a ring; and Z is selected from the group consisting of S, SO, and $SO_2$.

24. The compound according to claim 23, wherein at least one of $R_4$ and $R_5$ is not H.

25. The compound according to claim 23, wherein V is carbon and $R_{14}$ is hydrogen.

26. The compound according to claim 23, wherein two of J, K, L and M are taken together to form a further ring that is fused to the ring comprising J, K, L and M.

27. The compound according to claim 26, wherein the fused ring is a substituted or unsubstituted 5 or 6 membered aryl or heteroaryl ring.

28. The compound according to claim 26, wherein the fused ring is an alicyclic ring.

29. The compound according to claim 23, wherein $R_{21}$ is H.

30. The compound according to claim 23, wherein the ring formed by J, K, L and M comprises substituents that form a ring fused to the ring formed by J, K, L and M.

31. The compound according to claim 23, wherein $R_{11}$, $R_{12}$, $R_{13}$ and $R_{14}$ are each independently selected from the group consisting of hydrogen, F, Br, Cl, —$OCH_3$, —$SO_2Me$, —$SO_2NH_2$, —$SO_2NHMe$, —$SO_2NHCH_2CH_2OH$, —$SO_2NMe_2$, —$NHSO_2$(3-fluorophenyl), perhalo$(C_{1-10})$alkyl, —$OCF_3$, —$CF_3$, $(C_{1-10})$alkyl, hydroxy-$(C_{1-10})$alkyl, aryl, aryl-$(C_{1-10})$alkyl, heteroaryl, aminosulfonyl, alkylsulfonyl, arylsulfonyl, heteroarylsulfonyl, hydroxy, aryloxy, heteroaryloxy, arylalkyl, heteroaryl$(C_{1-10})$alkyl, cycloalkyl, heterocycloalkyl, HS—, $(C_{1-6})$alkylS-, cyano, nitro, cycloalkoxy, $(C_{1-12})$alkoxy, —COOH, —$CO_2Me$, carboxamide, $(C_{1-12})$alkylNHCO—, $R_9R_{10}N(C_{1-12})$alkyl aminocarbonyl, $R_9R_{10}N$—$(C_{1-12})$alkoxycarbonyl, hetero-$(C_{1-6})$alkylaminocarbonyl, heterocycloalkyl-$(C_{1-6})$alkylCO—, heteroaryl-$(C_{1-6})$alkylCO—, heterocycloalkyl-$(C_{1-6})$alkylOCO—, heteroaryl-$(C_{1-6})$alkylOCO—, $(C_{1-6})$alkylOCO—, diethoxyphosphorylmethyl, imino group, $R_9R_{10}N$—$(C_{1-6})$alkylsulfonyl, —$NH_2$, —$NHCH_3$, —$N(CH_3)_2$, —$NH(C_{1-3})$alkyl, —$N(C_{1-3}$-alkyl$)_2$, $R_9R_{10}N$—$(C_{1-12})$alkyl aminocarbonylamino, $R_9R_{10}N(C_{1-6})$alkyl alkoxycarbonylamino, heterocycloalkyl-$(C_{1-6})$alkyl aminocarbonylamino, heteroaryl-$(C_{1-6})$alkyl aminocarbonylamino, $(C_{3-12})$heterocycloalkyl-$(C_{1-6})$alkoxycarbonylamino, heteroaryl-$(C_{1-6})$alkoxycarbonylamino, $(C_{1-6})$alkyl carbonylamino, $((C_{1-6})$alkyl carbonyl)$(C_{1-6}$ alkyl)amino, $R_9R_{10}N$—$(C_{1-6})$alkyl carbonylamino, [$R_9R_{10}N$—$(C_{1-6})$alkylcarbonyl][$(C_{1-6})$alkyl]amino, $R_9R_{10}N$—$(C_{1-6})$alkyl sulfonylamino, [$R_9R_{10}N$—$(C_{1-6})$alkylsulfonyl][$(C_{1-6})$alkyl]amino, and —$R_9R_{10}$ where $R_9$ and $R_{10}$ are independently selected from the group consisting of hydrogen, $(C_{1-6})$alkyl, heterocycloalkyl, aryl and heteroaryl, each substituted or unsubstituted, or where $R_9$ and $R_{10}$ together are —$(CH_2)_{4-5}$— optionally interrupted by one O, S, NH or —$N(C_{1-3})$alkyl group, or where $R_9$ and $R_{10}$ together is selected from the group consisting of pyrrolidin-1-yl, morpholin-4-yl, and 4-methyl-piperazin-1-yl, each unsubstituted or substituted.

32. The compound according to claim 23, wherein $R_{11}$ and $R_{12}$, or $R_{12}$ and $R_{13}$, or $R_{13}$ and $R_{14}$ are taken together to form a substituted or unsubstituted fused ring.

33. The compound according to claim 32, wherein the fused ring is a substituted or unsubstituted 5 or 6 membered aryl or heteroaryl ring.

34. The compound according to claim 32, wherein the fused ring is a substituted or unsubstituted fused alicyclic ring.

35. The compound according to claim 23, wherein $R_4$ and $R_5$ are each independently selected from the group consisting of hydrogen, amino, cyano, $(C_{1-6})$alkyl, $(C_{1-6})$alkoxy, hydroxy-$(C_{1-6})$alkyl, $(C_{1-10})$alkoxycarbonyl, aryl, heterocyclyl, heteroaryl, aminocarbonyl, $(C_{1-6})$alkyl aminocarbonyl, halogen and hydroxy, each substituted or unsubstituted.

36. The compound according to claim 23, wherein $R_4$ is selected from the group consisting of 2-furanyl, 3-thienyl, Br, $CO_2Et$, hydrogen, cyano, 4-acetamidophenyl, and phenyl.

37. The compound according to claim 23, wherein $R_3$ and $R_4$ are taken together to form a substituted or unsubstituted fused ring.

38. The compound according to claim 37, wherein $R_3$ and $R_4$ are together selected from the group consisting of —NH—CH=N—, —NH—N=N—, —S—CH=N—, and —CH=CH—CH=N—.

39. The compound according to claim 23, wherein $R_5$ is selected from the group consisting of hydrogen, amino, $(C_{1-6})$alkyl, $(C_{1-6})$alkenyl, halo, phenyl, heteroaryl, heterocycloalkyl and $(C_{1-6})$alkoxy, each substituted or unsubstituted.

40. The compound according to claim 23, wherein $R_5$ is selected from the group consisting of Cl, methyl, 2-furanyl, 2-thienyl, Br, CH=$CH_2$, hydrogen and phenyl.

41. A compound comprising the formula:

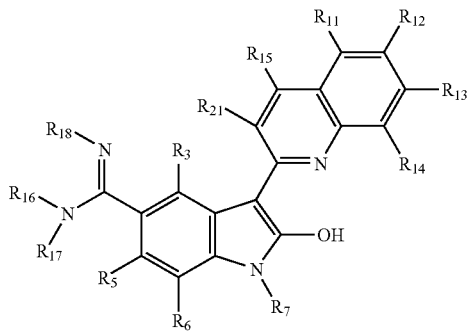

wherein:

$R_3$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{16}$ and $R_{17}$ are selected from the group consisting of hydrogen, hydroxy, alkoxy, aryloxy, heteroaryloxy, carbonyl, amino, sulfonamido, imino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{18}$ is selected from the group consisting of hydrogen, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{15}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted; and $R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{21}$ and $R_{15}$ are taken together to form a ring.

42. The compound according to claim 41, wherein $R_{14}$ is hydrogen.

43. The compound according to claim 41, wherein $R_{21}$ is H.

44. The compound according to claim 41, wherein $R_{15}$ is selected from the group consisting of hydrogen, amino, F, Br, Cl, —$OCH_3$, —$SO_2Me$, —$SO_2NH_2$, —$SO_2NHMe$, —$SO_2NHCH_2CH_2OH$, —$SO_2NMe_2$, —$NHSO_2$(3-fluorophenyl), perhalo($C_{1-10}$)alkyl, —$OCF_3$, —$CF_3$, ($C_{1-10}$)alkyl, hydroxy-($C_{1-10}$)alkyl, aryl, aryl-($C_{1-10}$)alkyl, heteroaryl, aminosulfonyl, alkylsulfonyl, arylsulfonyl, heteroarylsulfonyl, hydroxy, aryloxy, heteroaryloxy, arylalkyl, heteroaryl($C_{1-10}$)alkyl, cycloalkyl, heterocycloalkyl, HS—, ($C_{1-6}$)alkylS-, cyano, nitro, cycloalkoxy, ($C_{1-12}$)alkoxy, —COOH, —$CO_2Me$, carboxamide, ($C_{1-12}$)alkylN-HCO—, $R_9R_{10}N$—($C_{1-12}$)alkyl aminocarbonyl, $R_9R_{10}N$—($C_{1-12}$)alkoxycarbonyl, hetero-($C_{1-6}$)alkylaminocarbonyl, heterocycloalkyl-($C_{1-6}$)alkylCO—, heteroaryl-($C_{1-6}$)alkylCO—, heterocycloalkyl-($C_{1-6}$)alkylOCO—, heteroaryl-($C_{1-6}$)alkylOCO—, ($C_{1-6}$)alkylOCO—, diethoxyphosphorylmethyl, imino group, $R_9R_{10}N$—($C_{1-6}$)alkylsulfonyl, —$NH_2$, —$NHCH_3$, —$N(CH_3)_2$, —$NH(C_{1-3})$alkyl, —$N(C_{1-3}$-alkyl$)_2$, $R_9R_{10}N$—($C_{1-12}$)alkyl aminocarbonylamino, $R_9R_{10}N$—($C_{1-6}$)alkyl alkoxycarbonylamino, heterocycloalkyl-($C_{1-6}$)alkyl aminocarbonylamino, heteroaryl-($C_{1-6}$)alkyl aminocarbonylamino, ($C_{3-12}$)heterocycloalkyl-($C_{1-6}$)alkoxycarbonylamino, heteroaryl-($C_{1-6}$)alkoxycarbonylamino, ($C_{1-6}$)alkyl carbonylamino, (($C_{1-6}$)alkyl carbonyl)($C_{1-6}$)alkyl)amino, $R_9R_{10}N$—($C_{1-6}$)alkyl carbonylamino, [$R_9R_{10}N$—($C_{1-6}$)alkylcarbonyl][($C_{1-6}$)alkyl]amino, $R_9R_{10}N$—($C_{1-6}$)alkyl sulfonylamino, [$R_9R_{10}N$—($C_{1-6}$)alkylsulfonyl][($C_{1-6}$)alkyl]amino, and —$R_9R_{10}$ where $R_9$ and $R_{10}$ are independently selected from the group consisting of hydrogen, ($C_{1-6}$)alkyl, heterocycloalkyl, and heteroaryl, each substituted or unsubstituted, or where $R_9$ and $R_{10}$ together are —$(CH_2)_{4-5}$— optionally interrupted by one O, S, NH or —N($C_{1-3}$)alkyl group, or where $R_9$ and $R_{10}$ together is selected from the group consisting of pyrrolidin-1-yl, morpholin-4-yl, and 4-methyl-piperazin-1-yl, each unsubstituted or substituted.

45. The compound according to claim 41, wherein $R_{15}$ is selected from the group consisting of amino, —$SO_2Me$, —$SO_2NH_2$, —$SO_2NHMe$, —$SO_2NHCH_2CH_2OH$, —$SO_2NMe_2$, —$NHSO_2$(3-fluorophenyl), aminosulfonyl, alkylsulfonyl, arylsulfonyl, heteroarylsulfonyl, HS—, ($C_{1-6}$)alkylS-, carboxamide, imino group, $R_9R_{10}N$—($C_{1-6}$)alkylsulfonyl, —$NH_2$, —$NHCH_3$, —$N(CH_3)_2$, —$NH(C_{1-3})$alkyl, —$N(C_{1-3}$-alkyl$)_2$, $R_9R_{10}N$—($C_{1-12}$)alkyl aminocarbonylamino, $R_9R_{10}N$—($C_{1-6}$)alkyl alkoxycarbonylamino, heterocycloalkyl-($C_{1-6}$)alkyl aminocarbonylamino, heteroaryl-($C_{1-6}$)alkyl aminocarbonylamino, ($C_{3-12}$)heterocycloalkyl-($C_{1-6}$)alkoxycarbonylamino, heteroaryl-($C_{1-6}$)alkoxycarbonylamino, ($C_{1-6}$)alkyl carbonylamino, (($C_{1-6}$)alkyl carbonyl)($C_{1-6}$)alkyl)amino, $R_9R_{10}N$—($C_{1-6}$)alkyl carbonylamino, [$R_9R_{10}N$—($C_{1-6}$)alkylcarbonyl][($C_{1-6}$)alkyl]amino, $R_9R_{10}N$—($C_{1-6}$)alkyl sulfonylamino, [$R_9R_{10}N$—($C_{1-6}$)alkylsulfonyl][($C_{1-6}$)alkyl]amino, and —$R_9R_{10}$ where $R_9$ and $R_{10}$ are independently selected from the group consisting of hydrogen, ($C_{1-6}$)alkyl, heterocycloalkyl, and heteroaryl, each substituted or unsubstituted, or where $R_9$ and $R_{10}$ together are —$(CH_2)_{4-5}$— optionally interrupted by one O, S, NH or —$N(C_{1-3})$alkyl group, or where $R_9$ and $R_{10}$ together is selected from the group consisting of pyrrolidin-1-yl, morpholin-4-yl, and 4-methyl-piperazin-1-yl, each unsubstituted or substituted.

46. The compound according to claim 41, wherein $R_{15}$ is selected from the group consisting of hydrogen, F, Br, Cl, —$OCH_3$, —$SO_2Me$, —$SO_2NH_2$, —$SO_2NHMe$, —$SO_2NHCH_2CH_2OH$, —$SO_2NMe_2$, —$NHSO_2$(3-fluorophenyl), perhalo($C_{1-10}$)alkyl, —$OCF_3$, —$CF_3$, ($C_{1-10}$) alkyl, hydroxy-($C_{1-10}$)alkyl, aryl, aryl-($C_{1-10}$)alkyl, heteroaryl, aminosulfonyl, alkylsulfonyl, arylsulfonyl, heteroarylsulfonyl, hydroxy, aryloxy, heteroaryloxy, arylalkyl, heteroaryl($C_{1-10}$)alkyl, cycloalkyl, heterocycloalkyl, HS—, ($C_{1-6}$)alkylS-, cyano, nitro, cycloalkoxy, ($C_{1-12}$) alkoxy, —COOH, —$CO_2Me$, carboxamide, ($C_{1-12}$)alkylNHCO—, $R_9R_{10}N$—($C_{1-12}$)alkyl aminocarbonyl, $R_9R_{10}$—($C_{1-12}$)alkoxycarbonyl, hetero-($C_{1-6}$)alkylaminocarbonyl, heterocycloalkyl-($C_{1-6}$)alkylCO—, heteroaryl-($C_{1-6}$)alkylCO—, heterocycloalkyl-($C_{1-6}$)alkylOCO—, heteroaryl-($C_{1-6}$)alkylOCO—, ($C_{1-6}$)alkylOCO—, diethoxyphosphorylmethyl, imino group, $R_9R_{10}N$—($C_{1-6}$)alkylsulfonyl, —$NH_2$, —$NHCH_3$, —$N(CH_3)_2$, —$NH(C_{1-3})$alkyl, —$N(C_{1-3}$-alkyl$)_2$, $R_9R_{10}N$—($C_{1-12}$)alkyl aminocarbonylamino, $R_9R_{10}N$—($C_{1-6}$)alkyl alkoxycarbonylamino, heterocycloalkyl-($C_{1-6}$)alkyl aminocarbonylamino, heteroaryl-($C_{1-6}$)alkyl aminocarbonylamino, ($C_{3-12}$)heterocycloalkyl-($C_{1-6}$)alkoxycarbonylamino, heteroaryl-($C_{1-6}$)alkoxycarbonylamino, ($C_{1-6}$)alkyl carbonylamino, (($C_{1-6}$)alkyl carbonyl)($C_{1-6}$ alkyl)amino, $R_9R_{10}N$—($C_{1-6}$)alkyl carbonylamino, [$R_9R_{10}N$—($C_{1-6}$)alkylcarbonyl][($C_{1-6}$)alkyl]amino, $R_9R_{10}N$—($C_{1-6}$)alkyl sulfonylamino, [$R_9R_{10}N$—($C_{1-6}$)alkylsulfonyl][($C_{1-6}$)alkyl]amino, and —$R_9R_{10}$ where $R_9$ and $R_{10}$ are independently selected from the group consisting of hydrogen, ($C_{1-6}$)alkyl, heterocycloalkyl, and heteroaryl, each substituted or unsubstituted, or where $R_9$ and $R_{10}$ together are —$(CH_2)_{4-5}$— optionally interrupted by one O, S, NH or —$N(C_{1-3})$alkyl group, or where $R_9$ and $R_{10}$ together is selected from the group consisting of pyrrolidin-1-yl, morpholin-4-yl, and 4-methyl-piperazin-1-yl, each unsubstituted or substituted.

47. The compound according to claim 41, wherein $R_{11}$, $R_{12}$, $R_{13}$ and $R_{14}$ are each independently selected from the group consisting of hydrogen, F, Br, Cl, —$OCH_3$, —$SO_2Me$, —$SO_2NH_2$, —$SO_2NHMe$, —$SO_2NHCH_2CH_2OH$, —$SO_2NMe_2$, —$NHSO_2$(3-fluorophenyl), perhalo($C_{1-10}$) alkyl, —$OCF_3$, —$CF_3$, ($C_{1-10}$)alkyl, hydroxy-($C_{1-10}$)alkyl, aryl, aryl-($C_{1-10}$)alkyl, heteroaryl, aminosulfonyl, alkylsulfonyl, arylsulfonyl, heteroarylsulfonyl, hydroxy, aryloxy, heteroaryloxy, arylalkyl, heteroaryl($C_{1-10}$)alkyl, cycloalkyl, heterocycloalkyl, HS—, ($C_{1-6}$)alkylS—, cyano, nitro, cycloalkoxy, ($C_{1-12}$)alkoxy, —COOH, —$CO_2Me$, carboxamide, ($C_{1-12}$)alkylNHCO—, $R_9R_{10}N$—($C_{1-12}$)alkyl aminocarbonyl, $R_9R_{10}N$—($C_{1-12}$)alkoxycarbonyl, hetero-($C_{1-6}$)alkylaminocarbonyl, heterocycloalkyl-($C_{1-6}$)alkylCO—, heteroaryl-($C_{1-6}$)alkylCO—, heterocycloalkyl-($C_{1-6}$)alkylOCO—, heteroaryl-($C_{1-6}$)alkylOCO—, ($C_{1-6}$)alkylOCO—, diethoxyphosphorylmethyl, imino group, $R_9R_{10}N$—($C_{1-6}$) alkylsulfonyl, —$NH_2$, —$NHCH_3$, —$N(CH_3)_2$, —$NH(C_{1-3})$ alkyl, —$N(C_{1-3}$-alkyl$)_2$, $R_9R_{10}N$—($C_{-12}$)alkyl aminocarbonylamino, $R_9R_{10}N$—($C_{1-6}$)alkyl alkoxycarbonylamino, heterocycloalkyl-($C_{1-6}$)alkyl aminocarbonylamino, heteroaryl-($C_{1-6}$)alkyl aminocarbonylamino, ($C_{3-12}$)heterocycloalkyl-($C_{1-6}$)alkoxycarbonylamino, heteroaryl-($C_{1-6}$) alkoxycarbonylamino, ($C_{1-6}$)alkyl carbonylamino, (($C_{1-6}$) alkyl carbonyl)($C_{1-6}$ alkyl)amino, $R_9R_{10}N$—($C_{1-6}$)alkyl carbonylamino, [$R_9R_{10}N$—($C_{1-6}$)alkylcarbonyl][($C_{1-6}$) alkyl]amino, $R_9R_{10}N$—($C_{1-6}$)alkyl sulfonylamino, [$R_9R_{10}N$—($C_{1-6}$)alkylsulfonyl][($C_{1-6}$)alkyl]amino, and —$R_9R_{10}$ where $R_9$ and $R_{10}$ are independently selected from the group consisting of hydrogen, ($C_{1-6}$)alkyl, heterocycloalkyl, aryl and heteroaryl, each substituted or unsubstituted, or where $R_9$ and $R_{10}$ together are —$(CH_2)_{4-5}$— optionally interrupted by one O, S, NH or —$N(C_{1-3})$alkyl group, or where $R_9$ and $R_{10}$ together is selected from the group consisting of pyrrolidin-1-yl, morpholin-4-yl, and 4-methyl-piperazin-1-yl, each unsubstituted or substituted.

48. The compound according to claim 41, wherein $R_{11}$ and $R_{12}$, or $R_{12}$ and $R_{13}$, or $R_{13}$ and $R_{14}$ are taken together to form a substituted or unsubstituted fused ring.

49. The compound according to claim 48, wherein the fused ring is a substituted or unsubstituted 5 or 6 membered aryl or heteroaryl ring.

50. The compound according to claim 48, wherein the fused ring is a substituted or unsubstituted fused alicyclic ring.

51. The compound according to claim 41, wherein $R_5$ is selected from the group consisting of hydrogen, amino, ($C_{1-6}$)alkyl, ($C_{1-6}$)alkenyl, halo, phenyl, heteroaryl, heterocycloalkyl and ($C_{1-6}$)alkoxy, each substituted or unsubstituted.

52. The compound according to claim 41, wherein $R_5$ is selected from the group consisting of Cl, methyl, 2-furanyl, 2-thienyl, Br, CH=$CH_2$, hydrogen and phenyl.

53. A compound comprising the formula:

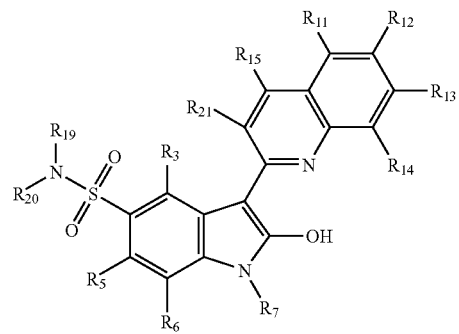

wherein:

$R_3$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{19}$ and $R_{20}$ are selected from the group consisting of hydrogen, hydroxy, alkoxy, aryloxy, heteroaryloxy, carbonyl, amino, imino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{15}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted; and $R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{21}$ and $R_{15}$ are taken together to form a ring.

54. The compound according to claim 53, wherein $R_{14}$ is hydrogen.

55. The compound according to claim 53, wherein $R_{21}$ is H.

56. The compound according to claim 53, wherein $R_{15}$ is selected from the group consisting of hydrogen, amino, F, Br, Cl, —OCH$_3$, —SO$_2$Me, —SO$_2$NH$_2$, —SO$_2$NHMe, —SO$_2$NHCH$_2$CH$_2$OH, —SO$_2$NMe$_2$, —NHSO$_2$(3-fluorophenyl), perhalo($C_{1-10}$)alkyl, —OCF$_3$, —CF$_3$, ($C_{1-10}$)alkyl, hydroxy-($C_{1-10}$)alkyl, aryl, aryl-($C_{1-10}$)alkyl, heteroaryl, aminosulfonyl, alkylsulfonyl, arylsulfonyl, heteroarylsulfonyl, hydroxy, aryloxy, heteroaryloxy, arylalkyl, heteroaryl($C_{1-10}$)alkyl, cycloalkyl, heterocycloalkyl, HS—, ($C_{1-6}$)alkylS-, cyano, nitro, cycloalkoxy, ($C_{1-12}$)alkoxy, —COOH, —CO$_2$Me, carboxamide, ($C_{1-12}$)alkylNHCO—, $R_9R_{10}$N—($C_{1-12}$)alkyl aminocarbonyl, $R_9R_{10}$N—($C_{1-12}$)alkoxycarbonyl, hetero-($C_{1-6}$)alkylaminocarbonyl, heterocycloalkyl-($C_{1-6}$)alkylCO—, heteroaryl-($C_{1-6}$)alkylCO—, heterocycloalkyl-($C_{1-6}$)alkylOCO—, heteroaryl-($C_{1-6}$)alkylOCO—, ($C_{1-6}$)alkylOCO—, diethoxyphosphorylmethyl, imino group, $R_9R_{10}$N—($C_{1-6}$)alkylsulfonyl, —NH$_2$, —NHCH$_3$, —N(CH$_3$)$_2$, —NH($C_{1-3}$)alkyl, —N($C_{1-3}$-alkyl)$_2$, $R_9R_{10}$N—($C_{1-12}$)alkyl aminocarbonylamino, $R_9R_{10}$N—($C_{1-6}$)alkyl alkoxycarbonylamino, heterocycloalkyl-($C_{1-6}$)alkyl aminocarbonylamino, heteroaryl-($C_{1-6}$)alkyl aminocarbonylamino, ($C_{3-12}$)heterocycloalkyl-($C_{1-6}$)alkoxycarbonylamino, heteroaryl-($C_{1-6}$)alkoxycarbonylamino, ($C_{1-6}$)alkyl carbonylamino, (($C_{1-6}$)alkyl carbonyl)($C_{1-6}$)alkyl)amino, $R_9R_{10}$N—($C_{1-6}$)alkyl carbonylamino, [$R_9R_{10}$N—($C_{1-6}$)alkylcarbonyl][($C_{1-6}$)alkyl]amino, $R_9R_{10}$N—($C_{1-6}$)alkyl sulfonylamino, [$R_9R_{10}$N—($C_{1-6}$)alkylsulfonyl][($C_{1-6}$)alkyl]amino, and —$R_9R_{10}$ where $R_9$ and $R_{10}$ are independently selected from the group consisting of hydrogen, ($C_{1-6}$)alkyl, heterocycloalkyl, and heteroaryl, each substituted or unsubstituted, or where $R_9$ and $R_{10}$ together are —(CH$_2$)$_{4-5}$— optionally interrupted by one O, S, NH or —N($C_{1-3}$)alkyl group, or where $R_9$ and $R_{10}$ together is selected from the group consisting of pyrrolidin-1-yl, morpholin-4-yl, and 4-methyl-piperazin-1-yl, each unsubstituted or substituted.

57. The compound according to claim 53, wherein $R_{15}$ is selected from the group consisting of amino, —SO$_2$Me, —SO$_2$NH$_2$, —SO$_2$NHMe, —SO$_2$NHCH$_2$CH$_2$OH, —SO$_2$NMe$_2$, —NHSO$_2$(3-fluorophenyl), aminosulfonyl, alkylsulfonyl, arylsulfonyl, heteroarylsulfonyl, HS—, ($C_{1-6}$)alkylS-, carboxamide, imino group, $R_9R_{10}$N—($C_{1-6}$)alkylsulfonyl, —NH$_2$, —NHCH$_3$, —N(CH$_3$)$_2$, —NH($C_{1-3}$)alkyl, —N($C_{1-3}$-alkyl)$_2$, $R_9R_{10}$N—($C_{1-12}$)alkyl aminocarbonylamino, $R_9R_{10}$N—($C_{1-6}$)alkyl alkoxycarbonylamino, heterocycloalkyl-($C_{1-6}$)alkyl aminocarbonylamino, heteroaryl-($C_{1-6}$)alkyl aminocarbonylamino, ($C_{3-12}$)heterocycloalkyl-($C_{1-6}$)alkoxycarbonylamino, heteroaryl-($C_{1-6}$)alkoxycarbonylamino, ($C_{1-6}$)alkyl carbonylamino, (($C_{1-6}$)alkyl carbonyl)($C_{1-6}$)alkyl)amino, $R_9R_{10}$N—($C_{1-6}$)alkyl carbonylamino, [$R_9R_{10}$N—($C_{1-6}$)alkylcarbonyl][($C_{1-6}$)alkyl]amino, $R_9R_{10}$N—($C_{1-6}$)alkyl sulfonylamino, [$R_9R_{10}$N—($C_{1-6}$)alkylsulfonyl][($C_{1-6}$)alkyl]amino, and —$R_9R_{10}$ where $R_9$ and $R_{10}$ are independently selected from the group consisting of hydrogen, ($C_{1-6}$)alkyl, heterocycloalkyl, and heteroaryl, each substituted or unsubstituted, or where $R_9$ and $R_{10}$ together are —(CH$_2$)$_{4-5}$— optionally interrupted by one O, S, NH or —N($C_{1-3}$)alkyl group, or where $R_9$ and $R_{10}$ together is selected from the group consisting of pyrrolidin-1-yl, morpholin-4-yl, and 4-methyl-piperazin-1-yl, each unsubstituted or substituted.

58. The compound according to claim 53, wherein $R_{15}$ is selected from the group consisting of hydrogen, F, Br, Cl, —OCH$_3$, —SO$_2$Me, —SO$_2$NH$_2$, —SO$_2$NHMe, —SO$_2$NHCH$_2$CH$_2$OH, —SO$_2$NMe$_2$, —NHSO$_2$(3-fluorophenyl), perhalo($C_{1-10}$)alkyl, —OCF$_3$, —CF$_3$, ($C_{1-10}$)alkyl, hydroxy-($C_{1-10}$)alkyl, aryl, aryl-($C_{1-10}$)alkyl, heteroaryl, aminosulfonyl, alkylsulfonyl, arylsulfonyl, heteroarylsulfonyl, hydroxy, aryloxy, heteroaryloxy, arylalkyl, heteroaryl($C_{1-10}$)alkyl, cycloalkyl, heterocycloalkyl, HS—, ($C_{1-6}$)alkylS-, cyano, nitro, cycloalkoxy, ($C_{1-12}$)

alkoxy, —COOH, —CO$_2$Me, carboxamide, (C$_{1-12}$)alkylN-HCO—, R$_9$R$_{10}$N—(C$_{1-12}$)alkyl aminocarbonyl, R$_9$R$_{10}$N—(C$_{1-12}$)alkoxycarbonyl, hetero-(C$_{1-6}$)alkylaminocarbonyl, heterocycloalkyl-(C$_{1-6}$)alkylCO—, heteroaryl-(C$_{1-6}$)alkylCO—, heterocycloalkyl-(C$_{1-6}$)alkylOCO—, heteroaryl-(C$_{1-6}$)alkylOCO—, (C$_{1-6}$)alkylOCO—, diethoxyphosphorylmethyl, imino group, R$_9$R$_{10}$N—(C$_{1-6}$)alkylsulfonyl, —NH$_2$, —NHCH$_3$, —N(CH$_3$)$_2$, —NH(C$_{1-3}$)alkyl, —N(C$_{1-3}$-alkyl)$_2$, R$_9$R$_{10}$N—(C$_{1-12}$)alkyl aminocarbonylamino, R$_9$R$_{10}$N—(C$_{1-6}$)alkyl alkoxycarbonylamino, heterocycloalkyl-(C$_{1-6}$)alkyl aminocarbonylamino, heteroaryl-(C$_{1-6}$)alkyl aminocarbonylamino, (C$_{3-12}$)heterocycloalkyl-(C$_{1-6}$)alkoxycarbonylamino, heteroaryl-(C$_{1-6}$)alkoxycarbonylamino, (C$_{1-6}$)alkyl carbonylamino, ((C$_{1-6}$)alkyl carbonyl)(C$_{1-6}$)alkyl)amino, R$_9$R$_{10}$N—(C$_{1-6}$)alkyl carbonylamino, [R$_9$R$_{10}$N—(C$_{1-6}$)alkylcarbonyl][(C$_{1-6}$)alkyl]amino, R$_9$R$_{10}$N—(C$_{1-6}$)alkyl sulfonylamino, [R$_9$R$_{10}$N—(C$_{1-6}$)alkylsulfonyl][(C$_{1-6}$)alkyl]amino, and —R$_9$R$_{10}$ where R$_9$ and R$_{10}$ are independently selected from the group consisting of hydrogen, (C$_{1-6}$)alkyl, heterocycloalkyl, and heteroaryl, each substituted or unsubstituted, or where R$_9$ and R$_{10}$ together are —(CH$_2$)$_{4-5}$— optionally interrupted by one O, S, NH or —N(C$_{1-3}$)alkyl group, or where R$_9$ and R$_{10}$ together is selected from the group consisting of pyrrolidin-1-yl, morpholin-4-yl, and 4-methyl-piperazin-1-yl, each unsubstituted or substituted.

59. The compound according to claim 53, wherein R$_{11}$, R$_{12}$, R$_{13}$ and R$_{14}$ are each independently selected from the group consisting of hydrogen, F, Br, Cl, —OCH$_3$, —SO$_2$Me, —SO$_2$NH$_2$, —SO$_2$NHMe, —SO$_2$NHCH$_2$CH$_2$OH, —SO$_2$NMe$_2$, —NHSO$_2$(3-fluorophenyl), perhalo(C$_{1-10}$)alkyl, —OCF$_3$, —CF$_3$, (C$_{1-10}$)alkyl, hydroxy-(C$_{1-10}$)alkyl, aryl, aryl-(C$_{1-10}$)alkyl, heteroaryl, aminosulfonyl, alkylsulfonyl, arylsulfonyl, heteroarylsulfonyl, hydroxy, aryloxy, heteroaryloxy, arylalkyl, heteroaryl(C$_{1-10}$)alkyl, cycloalkyl, heterocycloalkyl, HS—, (C$_{1-6}$)alkylS-, cyano, nitro, cycloalkoxy, (C$_{1-12}$)alkoxy, —COOH, —CO$_2$Me, carboxamide, (C$_{1-12}$)alkylNHCO—, R$_9$R$_{10}$N—(C$_{1-12}$)alkyl aminocarbonyl, R$_9$R$_{10}$N—(C$_{1-6}$)alkoxycarbonyl, hetero-(C$_{1-6}$)alkylaminocarbonyl, heterocycloalkyl-(C$_{1-6}$)alkylCO—, heteroaryl-(C$_{1-6}$)alkylCO—, heterocycloalkyl-(C$_{1-6}$)alkylOCO—, heteroaryl-(C$_{1-6}$)alkylOCO—, (C$_{1-6}$)alkylOCO—, diethoxyphosphorylmethyl, imino group, R$_9$R$_{10}$N—(C$_{1-6}$)alkylsulfonyl, —NH$_2$, —NHCH$_3$, —N(CH$_3$)$_2$, —NH(C$_{1-3}$)alkyl, —N(C$_{1-3}$-alkyl)$_2$, R$_9$R$_{10}$N—(C$_{1-12}$)alkyl aminocarbonylamino, R$_9$R$_{10}$N—(C$_{1-6}$)alkyl alkoxycarbonylamino, heterocycloalkyl-(C$_{1-6}$)alkyl aminocarbonylamino, heteroaryl-(C$_{1-6}$)alkyl aminocarbonylamino, (C$_{3-12}$)heterocycloalkyl-(C$_{1-6}$)alkoxycarbonylamino, heteroaryl-(C$_{1-6}$)alkoxycarbonylamino, (C$_{1-6}$)alkyl carbonylamino, ((C$_{1-6}$)alkyl carbonyl)(C$_{1-6}$ alkyl)amino, R$_g$R$_{10}$N—(C$_{1-6}$)alkyl carbonylamino, [R$_9$R$_{10}$N—(C$_{1-6}$)alkylcarbonyl][(C$_{1-6}$)alkyl]amino, R$_9$R$_{10}$N—(C$_{1-6}$)alkyl sulfonylamino, [R$_9$R$_{10}$N—(C$_{1-6}$)alkylsulfonyl][(C$_{1-6}$)alkyl]amino, and —R$_9$R$_{10}$ where R$_9$ and R$_{10}$ are independently selected from the group consisting of hydrogen, (C$_{1-6}$)alkyl, heterocycloalkyl, aryl and heteroaryl, each substituted or unsubstituted, or where R$_9$ and R$_{10}$ together are —(CH$_2$)$_{4-5}$— optionally interrupted by one O, S, NH or —N(C$_{1-3}$)alkyl group, or where R$_9$ and R$_{10}$ together is selected from the group consisting of pyrrolidin-1-yl, morpholin-4-yl, and 4-methyl-piperazin-1-yl, each unsubstituted or substituted.

60. The compound according to claim 53, wherein R$_{11}$, and R$_{12}$, or R$_{12}$ and R$_{13}$, or R$_{13}$ and R$_{14}$ are taken together to form a substituted or unsubstituted fused ring.

61. The compound according to claim 60, wherein the fused ring is a substituted or unsubstituted 5 or 6 membered aryl or heteroaryl ring.

62. The compound according to claim 60, wherein the fused ring is a substituted or unsubstituted fused alicyclic ring.

63. The compound according to claim 53, wherein R$_5$ is selected from the group consisting of hydrogen, amino, (C$_{1-6}$)alkyl, (C$_{1-6}$)alkenyl, halo, phenyl, heteroaryl, heterocycloalkyl and (C$_{1-6}$)alkoxy, each substituted or unsubstituted.

64. The compound according to claim 53, wherein R$_5$ is selected from the group consisting of Cl, methyl, 2-furanyl, 2-thienyl, Br, CH═CH$_2$, hydrogen and phenyl.

65. A compound comprising the formula:

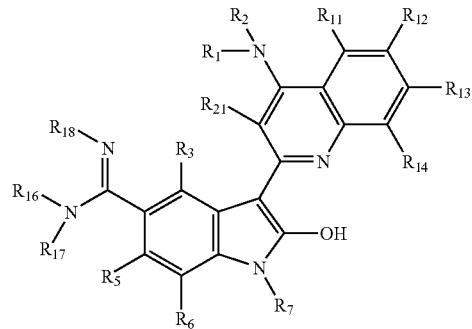

wherein:
R$_1$ and R$_2$ are selected from the group consisting of hydrogen, hydroxy, alkoxy, aryloxy, heteroaryloxy, carbonyl, amino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted;

R$_3$, R$_5$, and R$_6$ are each independently selected from the group consisting of hydrogen, halo, perhalo(C$_{1-10}$)alkyl, amino, nitro, cyano, thio, sulfonamide, (C$_{1-10}$)alkyl, (C$_{3-12}$)cycloalkyl, hetero(C$_{3-12}$)cycloalkyl, aryl(C$_{1-10}$)alkyl, heteroaryl(C$_{1-5}$)alkyl, (C$_{9-12}$)bicycloaryl, hetero(C$_{4-12}$)bicycloaryl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of R$_3$, R$_5$, and R$_6$ are taken together to form a ring, with the proviso that R$_3$, R$_5$, and R$_6$ are absent where the ring atom to which R$_3$, R$_5$, and R$_6$ are bound is nitrogen;

R$_7$ is hydrogen or a substituent convertible in vivo to hydrogen;

R$_{11}$, R$_{12}$, R$_{13}$, and R$_{14}$ are each independently selected from the group consisting of hydrogen, (C$_{1-12}$)alkyl, alkoxy, thio, hydroxy, (C$_{3-12}$)cycloalkyl, hetero(C$_{3-12}$)cycloalkyl, hetero(C$_{3-12}$)cycloalkoxy, (C$_{9-12}$)bicycloaryl, hetero(C$_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of R$_{11}$, R$_{12}$, R$_{13}$, and R$_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{16}$ and $R_{17}$ are selected from the group consisting of hydrogen, hydroxy, alkoxy, aryloxy, heteroaryloxy, carbonyl, amino, sulfonamido, imino, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{18}$ is selected from the group consisting of hydrogen, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_1$ are taken together to form a ring.

66. A compound comprising the formula:

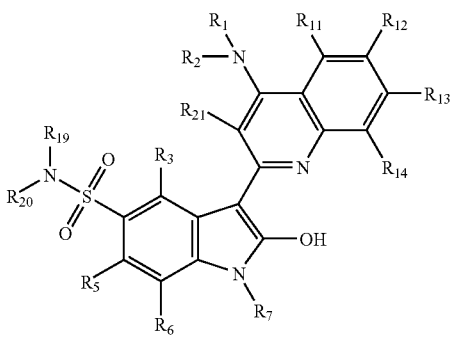

wherein:

$R_1$ and $R_2$ are selected from the group consisting of hydrogen, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_3$, $R_5$, and $R_6$ are each independently selected from the group consisting of hydrogen, halo, perhalo$(C_{1-10})$alkyl, amino, nitro, cyano, thio, sulfonamide, $(C_{1-10})$alkyl, $(C_{3-12})$cycloalkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, $(C_{1-12})$alkyl, alkoxy, thio, hydroxy, $(C_{3-12})$cycloalkyl, hetero$(C_{3-12})$cycloalkyl, hetero$(C_{3-12})$cycloalkoxy, $(C_{9-12})$bicycloaryl, hetero$(C_{8-12})$bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{19}$ and $R_{20}$ are selected from the group consisting of hydrogen, hydroxy, alkoxy, aryloxy, heteroaryloxy, carbonyl, amino, imino, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{21}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{21}$ and $R_1$ are taken together to form a ring.

67. A compound comprising the formula:

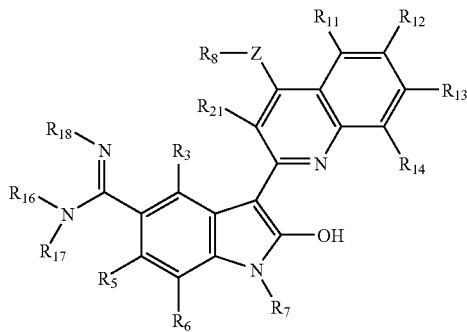

wherein:

$R_3$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_8$ is selected from the group consisting of hydrogen, alkoxy, aryloxy, heteroaryloxy, carbonyl, amino, ($C_{1-10}$)alkylamino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{16}$ and $R_{17}$ are selected from the group consisting of hydrogen, hydroxy, alkoxy, aryloxy, heteroaryloxy, carbonyl, amino, sulfonamido, imino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{18}$ is selected from the group consisting of hydrogen, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{21}$ and $R_8$ are taken together to form a ring; and Z is selected from the group consisting of S, SO, and $SO_2$.

68. A compound comprising the formula:

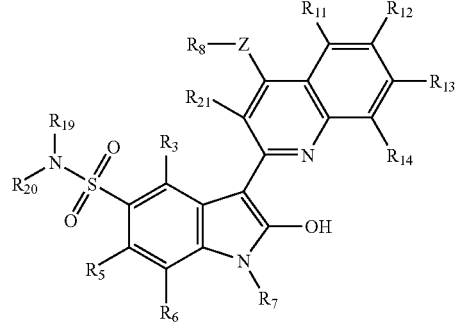

wherein:

$R_3$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_8$ is selected from the group consisting of hydrogen, alkoxy, aryloxy, heteroaryloxy, carbonyl, amino, ($C_{1-10}$)alkylamino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{16}$ and $R_{17}$ are selected from the group consisting of hydrogen, hydroxy, alkoxy, aryloxy, heteroaryloxy, carbonyl, amino, sulfonamido, imino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{18}$ is selected from the group consisting of hydrogen, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{19}$ and $R_{20}$ are selected from the group consisting of hydrogen, hydroxy, alkoxy, aryloxy, heteroaryloxy, carbonyl, amino, imino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{21}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_{21}$ and $R_8$ are taken together to form a ring; and Z is selected from the group consisting of S, SO, and $SO_2$.

69. A compound comprising the formula:

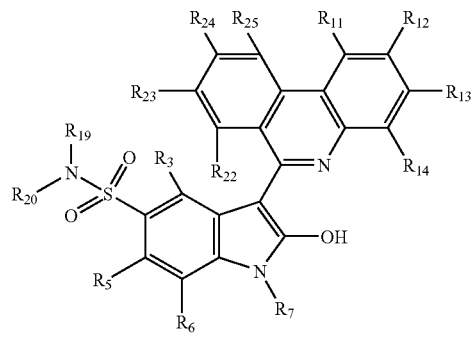

wherein:

$R_3$, $R_5$, and $R_6$ are each independently selected from the group consisting of hydrogen, halo, perhalo($C_{1-10}$)alkyl, amino, nitro, cyano, thio, sulfonamide, ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or two of $R_3$, $R_5$, and $R_6$ are taken together to form a ring, with the proviso that $R_3$, $R_5$, and $R_6$ are absent where the ring atom to which $R_3$, $R_5$, and $R_6$ are bound is nitrogen;

$R_7$ is hydrogen or a substituent convertible in vivo to hydrogen;

$R_{11}$, $R_{12}$, $R_{13}$, and $R_{14}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{11}$, $R_{12}$, $R_{13}$, and $R_{14}$ are taken together to form a ring, with the proviso that $R_{11}$, $R_{12}$, $R_{13}$ and $R_{14}$ are absent when the ring atom to which $R_{11}$, $R_{12}$, $R_{13}$ and $R_{14}$ are bound is nitrogen;

$R_{19}$ and $R_{20}$ are selected from the group consisting of hydrogen, hydroxy, alkoxy, aryloxy, heteroaryloxy, carbonyl, amino, imino, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted; and $R_{22}$, $R_{23}$, $R_{24}$, and $R_{25}$ are each independently selected from the group consisting of hydrogen, ($C_{1-12}$)alkyl, alkoxy, thio, hydroxy, ($C_{3-12}$)cycloalkyl, hetero($C_{3-12}$)cycloalkyl, hetero($C_{3-12}$)cycloalkoxy, ($C_{9-12}$)bicycloaryl, hetero($C_{8-12}$)bicycloaryl, aryl, heteroaryl, heteroaryloxy, aryloxy, amino, carbonyl group, imino group, sulfonyl group and sulfinyl group, halo, cyano, nitro, and trifluoromethoxy, each substituted or unsubstituted, or any two of $R_{22}$, $R_{23}$, $R_{24}$, and $R_{25}$ are taken together to form a ring, or $R_{25}$ and $R_1$ are taken together to form a ring.

70. A compound selected from the group consisting of:
5-Amino-3-quinolin-2-yl-1H-indol-2-ol;
8-Quinolin-2-yl-6,8-dihydro-thiazolo[5,4-e]indol-7-one;
5-(3-Fluoro-phenyl)-3-quinolin-2-yl-1H-indol-2-ol;
5-Biphenyl-4-yl-3-quinolin-2-yl-1H-indol-2-ol;
5-(4-Methyl-phenyl)-3-quinolin-2-yl-1H-indol-2-ol;
5-(4-Phenoxy-phenyl)-3-quinolin-2-yl-1H-indol-2-ol;
5-(4-Fluoro-phenyl)-3-quinolin-2-yl-1H-indol-2-ol;
5-(4-Methoxy-phenyl)-3-quinolin-2-yl-1H-indol-2-ol;
5-(4-Methanesulfonyl-phenyl)-3-quinolin-2-yl-1H-indol-2-ol;
5-(4-Nitrile-phenyl)-3-quinolin-2-yl-1H-indol-2-ol;
5-(2-Phenylvinyl)-3-quinolin-2-yl-1H-indol-2-ol;
5-(4-Hydroxymethyl -phenyl)-3-quinolin-2-yl-1H-indol-2-ol;
5-(4-Hydroxy-phenyl)-3-quinolin-2-yl-1H-indol-2-ol;
5-(2-(4-Fluorophenyl)-vinyl)-3-quinolin-2-yl-1H-indol-2-ol;
5-(3-Amino-phenyl)-3-quinolin-2-yl-1H-indol-2-ol;
5-(3-Furan)-3-quinolin-2-yl-1H-indol-2-ol;
5-(2-Fluoro-phenyl)-3-quinolin-2-yl-1H-indol-2-ol;
5-(2-Methoxy-phenyl)-3-quinolin-2-yl-1H-indol-2-ol;
5-(2-Trifluoromethyl-phenyl)-3-quinolin-2-yl-1H-indol-2-ol;
5-(2-Hydroxy-phenyl)-3-quinolin-2-yl-1H-indol-2-ol;
6-(2-Fluoro-phenyl)-3-quinolin-2-yl-1H-indol-2-ol;
6-(3-Amino-phenyl)-3-quinolin-2-yl-1H-indol-2-ol;
5-(2-Chloro-phenyl)-3-quinolin-2-yl-1H-indol-2-ol;
6-(4-Fluoro-phenyl)-3-quinolin-2-yl-1H-indol-2-ol;
6-(Phenyl)-3-quinolin-2-yl-1H-indol-2-ol;
6-(3-Methanesulfonyl-phenyl)-3-quinolin-2-yl-1H-indol-2-ol;
5-(3-Methanesulfonyl-amino-phenyl)-3-quinolin-2-yl-1H-indol-2-ol;
5-(3-Acetamide-phenyl)-3-quinolin-2-yl-1H-indol-2-ol;
5-(2-Hydroxymethyl -phenyl)-3-quinolin-2-yl-1H-indol-2-ol;
5-(4-Amino-phenyl)-3-quinolin-2-yl-1H-indol-2-ol;
5-(4-Carbamic acid benzyl ester)-3-quinolin-2-yl-1H-indol-2-ol;
5-(3-Ethoxy-phenyl)-3-quinolin-2-yl-1H-indol-2-ol;
5-(3-Ethanesulfonyl-phenyl)-3-quinolin-2-yl-1H-indol-2-ol;
1-Benzenesulfonyl-3'-quinolin-2-yl-1H, 1'H-[2,5']biindolyl-2'-01;
5-(3-Amino-5-carboxy -phenyl)-3-quinolin-2-yl-1H-indol-2-ol;
5-(2-Pyrrole)-3-quinolin-2-yl-1H-indol-2-ol;
5-(2-Indol)-3-quinolin-2-yl-1H-indol-2-ol;
5-Pyridin-4-yl-3-quinolin-2-yl-1H-indol-2-ol;
5(3-Aminomethyl-phenyl)-3-quinolin-2-yl-1H-indol-2-ol;
5-(3-Hydroxymethyl-phenyl)-3-quinolin-2-yl-1H-indol-2-ol;
5-(4-Aminomethyl-phenyl)-3-quinolin-2-yl-1H-indol-2-ol;
3-(4-Phenethylamino-quinolin-2-yl)-1H-indol-2-ol;
3-(4-Piperidinylamino-quinolin-2-yl)-1H-indol-2-ol;
3-(4-Benzylamino-quinolin-2-yl)-1H-indol-2-ol;
3-[4-(2-Diethylamino-ethylamino)-quinolin-2-yl]-1H-indol-2-ol;
3-(4-Phenylamino-qunolin-2-yl)-1H-indol-2-ol;
3-[4-(2-Piperazin-1-yl-ethylamino)-quinolin-2-yl]-1H-indol-2-ol;
3-(4-Methylamino-quinolin-2-yl)-1H-indol-2-ol;
3-(4-Ethylamino-quinolin-2-yl)-1H-indol-2-ol;
3-(4-Diethylamino-quinolin-2-yl)-1H-indol-2-ol;
3-(4-Isopropylamino-quinolin-2-yl)-1H-indol-2-ol;
3-(4-Cyclohexylamino-quinolin-2-yl)-1H-indol-2-ol;
3-(4-Cyclopentylamino-quinolin-2-yl)-1H-indol-2-ol;
3-(4-Dimethylamino-quinolin-2-yl)-1H-indol-2-ol;
3-(4-tert-Butylamino-quinolin-2-yl)-1H-indol-2-ol;
3-[4-(Methyl-phenyl-amino)-quinolin-2-yl]-1H-indol-2-ol;
3-(4-Morpholin-4-yl-quinolin-2-yl)-1H-indol-2-ol;
3-[4-(4-Methyl-piperazin-1-yl)-quinolin-2-yl]-1H-indol-2-ol;
3-[-4-(Biphenyl-4-ylamino)-quinolin-2-yl]-1H-indol-2-ol;
3-(4-[2-(4-Hydroxy-phenyl)-ethylamino]-quinolin-2-yl 1-1H-indol-2-ol;
3-[4-(3-Morpholin-4-yl-propylamino)-quinolin-2-yl]-1H-indol-2-ol;
3-[4-(4-Phenoxy-phenylamino)-quinolin-2-yl]-1H-indol-2-ol;
3-[4-(Methyl-pyridin-3-yl-amino)-quinolin-2-yl]-1H-indol-2-ol;
3-[4-(Methyl-pyridin-4-yl-amino)-quinolin-2-yl]-1H-indol-2-ol;
3-[4-(3-Fluoro-phenylamino)-quinolin-2-yl]-1H-indol-2-ol;
3-[4-(Pyridin-3-ylamino)-quinolin-2-yl]-1H-indol-2-ol;
3-[4-(2-Morpholin-4-yl-ethylamino)-quinolin-2-ylII-1H-indol-2-ol;
3-(4-Phenylsulfanyl-quinolin-2-yl)-1H-indol-2-ol;
N-{4-[2-(2-Hydroxy-1H-indol-3-yl)-quinolin-4-yl-sulfanyl]-phenyl}-acetamide;
3-(4-Amino-quinolin-2-yl)-1H-indol-2-ol;
3-(4-Ethylsulfanyl-quinolin-2-yl)-1H-indol-2-ol;
1-[2-Hydroxy-3-(8-hydroxy-quinolin-2-yl)-indol-1-yl]-ethanone;
3-[4-(4-Amino-phenylamino)-quinolin-2-yl]-1H-indol-2-ol;
N-{4-[2-(2-Hydroxy-1H-indol-3-yl)-quinolin-4-ylamino]-phenyl}-acetamide;
3-[4-(6-Amino-pyridin-3-ylamino)-quinolin-2-yl]-1H-indol-2-ol;
N-{4-[3-(4-Chloro-quinolin-2-yl)-2-hydroxy-1H-indol-5-yl]-phenyl}-acetamide;
2,N-Dihydroxy-3-quinolin-2-yl-1H-indole-5-carboxamidine;
2-Hydroxy-3-quinolin-2-yl-1H-indole-5-carboxamidine;
N-{4-[3-(3-Methyl-quinolin-2-yl)-2-oxo-2,3-dihydro-1H-indol-5-yl]-phenyl}-acetamide;
Ethanesulfonic acid (2-hydroxy-3-quinolin-2-yl-1H-indol-5-yl)-amide;
Ethanesulfonic acid [3-(4-chloro-quinolin-2-yl)-2-hydroxy-1H-indol-5-yl]-amide;
2-Hydroxy-3-quinolin-2-yl-1H-indole-5-carboximidic acid ethyl ester;
N-(2-Dimethylamino-ethyl)-2-hydroxy-3-quinolin-2-yl-1H-indole-5-carboxamidine;
2-Hydroxy-3-(4-phenylamino-quinolin-2-yl)-1H-indole-5-carbonitrile;
3-[4-(4-Amino-phenylamino)-quinolin-2-yl]-2-hydroxy-1H-indole-5-carbonitrile;
2-Hydroxy-3-{4-[(pyridin-2-ylmethyl)-amino]-quinolin-2-yl}-1H-indole-5-carbonitrile;
2-Hydroxy-3-{4-[(pyridin-3-ylmethyl)-amino]-quinolin-2-yl}-1H-indole-5-carbonitrile;
2-Hydroxy-3-{4-[(pyridin-4-ylmethyl)-amino]-quinolin-2-yl}-1H-indole-5-carbonitrile;
N-(3-Dimethylamino-propyl)-2-hydroxy-3-quinolin-2-yl-1H-indole-5-carboxamidine;

3-[4-(6-Amino-pyridin-3-ylamino)-quinolin-2-yl]-2-hydroxy-1H-indole-5-carbonitrile;
3-[4-(6-Amino-pyridin-3-ylamino)-quinolin-2-yl]-5-nitro-1H-indol-2-ol;
Ethanesulfonic acid {3-[4-(4-amino-phenylamino)-quinolin-2-yl]-2-hydroxy-1H-indol-5-yl}-amide;
N-{4-[3-(3-Methyl-quinolin-2-yl)-2-oxo-2,3-dihydro-1H-indol-5-yl]-phenyl}-methanesulfonamide;
N-{3-[3-(3-Methyl-quinolin-2-yl)-2-oxo-2,3-dihydro-1H-indol-5-yl]-phenyl}-methanesulfonamide;
Ethanesulfonic acid (2-hydroxy-3-{4-[(pyridin-2-ylmethyl)-amino]-quinolin-2-yl}1-1H-indol-5-yl)-amide;
2-Hydroxy-N-methyl-3-quinolin-2-yl-1H-indole-5-carboxamidine;
N-Hydroxy-3-(3-methyl-quinolin-2-yl)-2-oxo-2,3-dihydro-1H-indole-5-carboxamidine;
N-{4-[2-(5-Cyano-2-hydroxy-1H-indol-3-yl)-quinolin-4-ylsulfanyl]-phenyl}-acetamide;
N-{4-[2-(5-Cyano-2-hydroxy-1H-indol-3-yl)-quinolin-4-ylamino]-phenyl}-acetamide;
Ethanesulfonic acid (2-hydroxy-3-{4-[(pyridin-3-ylmethyl)-amino]-quinolin-2-yl}-1H-indol-5-yl)-amide;
Ethanesulfonic acid (2-hydroxy-3-{4-[(pyridin-4-ylmethyl)-amino]-quinolin-2-yl}-1H-indol-5-yl)-amide;
2-Hydroxy-N-(2-morpholin-4-yl-ethyl)-3-quinolin-2-yl-1H-indole-5-carboxamidine;
2-Hydroxy-N-(3-morpholin-4-yl-propyl)-3-quinolin-2-yl-1H-indole-5-carboxamidine;
2-Hydroxy-3-quinolin-2-yl-N-(2-thiomorpholin-4-yl-ethyl)-1H-indole-5-carboxamidine;
2-Hydroxy-N-(2-piperidin-1-yl-ethyl)-3-quinolin-2-yl-1H-indole-5-carboxamidine;
2-Hydroxy-N-[3-(4-methyl-piperazin-1-yl)-propyl]-3-quinolin-2-yl-1H-indole-5-carboxamidine;
2-Hydroxy-N-pyridin-4-ylmethyl-3-quinolin-2-yl-1H-indole-5-carboxamidine;
2-Hydroxy-3-quinolin-2-yl-1H-indole-5-sulfonic acid ethylamide;
2-Hydroxy-3-quinolin-2-yl-1H-indole-5-sulfonic acid pyridin-3-ylamide;
2N-Dihydroxy-3-{4-[(pyridin-3-ylmethyl)-amino]-quinolin-2-yl}1-1H-indole-5-carboxamidine;
3-[4-(4-Amino-phenylamino)-quinolin-2-yl]-2,N-dihydroxy-1H-indole-5-carboxamidine;
2,N-Dihydroxy-3-{4-[(pyridin-2-ylmethyl)-amino]-quinolin-2-yl}-1H-indole-5-carboxamidine;
2,N-Dihydroxy-3-{4-[(pyridin-4-ylmethyl)-amino]-quinolin-2-yl}-1H-indole-5-carboxamidine;
3-[4-(6-Amino-pyridin-3-ylamino)-quinolin-2-yl]-2,N-dihydroxy-1H-indole-5-carboxamidine;
3-[6-(2-Diethylamino-ethoxy)-quinolin-2-yl]-2,N-dihydroxy-1H-indole-5-carboxamidine;
2,N-Dihydroxy-3-[6-(2-morpholin-4-yl-ethoxy)-quinolin-2-yl]-1H-indole-5-carboxamidine;
N-(2-Hydroxy-3-quinolin-2-yl-1H-indol-5-yl)-benzenesulfonamide;
N-(2-Hydroxy-3-quinolin-2-yl-1H-indol-5-yl)-3-nitro-benzenesulfonamide;
N-(2-Hydroxy-3-quinolin-2-yl-1H-indol-5-yl)-4-nitro-benzenesulfonamide;
Naphthalene-1-sulfonic acid (2-hydroxy-3-quinolin-2-yl-1H-indol-5-yl)-amide;
N-(2-Hydroxy-3-quinolin-2-yl-1H-indol-5-yl)-3-methoxy-benzenesulfonamide;
Naphthalene-2-sulfonic acid (2-hydroxy-3-quinolin-2-yl-1H-indol-5-yl)-amide;
2,3-Dihydro-benzo[1,4]dioxine-6-sulfonic acid (2-hydroxy-3-quinolin-2-yl-1H-indol-5-yl)-amide;
Thiophene-2-sulfonic acid (2-hydroxy-3-quinolin-2-yl-1H-indol-5-yl)-amide;
N-(2-Hydroxy-3-quinolin-2-yl-1H-indol-5-yl)-3-methyl-benzenesulfonamide;
N-[3-(4-Chloro-quinolin-2-yl)-2-hydroxy-1H-indol-5-yl]-benzenesulfonamide;
N-[3-(4-Chloro-quinolin-2-yl)-2-hydroxy-1H-indol-5-yl]-3-nitro-benzenesulfonamide;
N-[3-(4-Chloro-quinolin-2-yl)-2-hydroxy-1H-indol-5-yl]-4-nitro-benzenesulfonamide;
Naphthalene-1-sulfonic acid [3-(4-chloro-quinolin-2-yl)-2-hydroxy-1H-indol-5-yl]-amide;
N-[3-(4-Chloro-quinolin-2-yl)-2-hydroxy-1H-indol-5-yl]-3-methoxy-benzenesulfonamide;
Naphthalene-2-sulfonic acid [3-(4-chloro-quinolin-2-yl)-2-hydroxy-1H-indol-5-yl]-amide;
2,3-Dihydro-benzo[1,4]dioxine-6-sulfonic acid [3-(4-chloro-quinolin-2-yl)-2-hydroxy-1H-indol-5-yl]-amide;
N-[3-(4-Chloro-quinolin-2-yl)-2-hydroxy-1H-indol-5-yl]-3-methyl-benzenesulfonamide;
C-(3-Chloro-phenyl)-N-[3-(4-chloro-quinolin-2-yl)-2-hydroxy-1H-indol-5-yl]-methanesulfonamide;
3-Chloro-N-[3-(4-chloro-quinolin-2-yl)-2-hydroxy-1H-indol-5-yl]-benzenesulfonamide;
3-Chloro-N-(2-hydroxy-3-quinolin-2-yl-1H-indol-5-yl)-benzenesulfonamide;
C-(3-Chloro-phenyl)-N-(2-hydroxy-3-quinolin-2-yl-1H-indol-5-yl)-methanesulfonamide;
3-Amino-N-(2-hydroxy-3-quinolin-2-yl-1H-indol-5-yl)-benzenesulfonamide;
4-Amino-N-(2-hydroxy-3-quinolin-2-yl-1H-indol-5-yl)-benzenesulfonamide;
N-[3-(4-Chloro-quinolin-2-yl)-2-hydroxy-1H-indol-5-yl]-C-phenyl-methanesulfonamide;
2-Hydroxy-3-quinolin-2-yl-1H-indole-5-sulfonic acid hydroxyamide;
2,N-Dihydroxy-3-quinolin-2-yl-1H-indole-5-carboxamidine-O-acetyl;
3-(4-Hydroxyamino-quinolin-2-yl)-1H-indol-2-ol;
2-Hydroxy-3-phenanthridin-6-yl-1H-indole-5-sulfonic acid ethylamide;
3-[6-(2-Diethylamino-ethoxy)-quinolin-2-yl]-2-hydroxy-1H-indole-5-sulfonic acid ethylamide;
2,N-Dihydroxy-3-(4-phenylamino-quinolin-2-yl)-1H-indole-5-carboxamidine;
N-[5-(2-Hydroxy-3-quinolin-2-yl-1H-indole-5-sulfonylamino)-pyridin-2-yl]-acetamide;
3-[6-(2-Diethylamino-ethoxy)-quinolin-2-yl]-2-hydroxy-1H-indole-5-sulfonic acid methylamide;
3-[6-(2-Dimethylamino-ethoxy)-quinolin-2-yl]-2-hydroxy-1H-indole-5-sulfonic acid methylamide;
3-[6-(2-Dimethylamino-ethoxy)-quinolin-2-yl]-2-hydroxy-1H-indole-5-sulfonic acid ethylamide; and
3-[6-(2-Dimethylamino-ethoxy)-quinolin-2-yl]-2,N-dihydroxy-1H-indole-5-carboxamidine.

71. The compound according to claim 1, wherein the compound is in the form of a pharmaceutically acceptable salt, biohydrolyzable ester, biohydrolyzable amide, biohydrolyzable carbamate, solvate, hydrate or prodrug thereof.

72. The compound according to claim 1, wherein the compound in its active state is in the enol tautomer.

73. The compound according to claim 1, wherein the compound is present in a mixture of stereoisomers.

74. The compound according to claim 1, wherein the compound comprises a single stereoisomer.

75. A pharmaceutical composition comprising, as an active ingredient, a compound according to claim 1.

76. The pharmaceutical composition according to claim 75, wherein the composition is a solid formulation adapted for oral administration.

77. A pharmaceutical composition according to claim 75, wherein the composition is a liquidformulation adapted for oral administration.

78. A pharmaceutical composition according to claim 75, wherein the composition is a tablet.

79. A pharmaceutical composition according to claim 75, wherein the composition is a liquid formulation adapted for parenteral administration.

80. A pharmaceutical composition comprising a compound according to claim 1, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, and intrathecally.

81. A kit comprising:
a compound according to claim 1; and
instructions which comprise one or more forms of information selected from the group consisting of indicating a disease state for which the compound is to be administered, storage information for the compound, dosing information and instructions regarding how to administer the compound.

82. The kit of claim 81, wherein the kit comprises the compound in a multiple dose form.

83. A method of inhibiting kinase comprising: contacting kinase with a compound according to claim 1;

84. The method according to claim 83, wherein the inhibition arises from a favorable conformation adopted by the compound in its enol form, and wherein the conformation arises from an intramolecular hydrogen bonding of the enol hydrogen and an adjacent nitrogen atom of the compound.

85. The method according to claim 83, wherein the inhibition arises from a favorable conformation adopted by the compound in its enol form, and said inhibition arises from a hydrogen bonding interaction between the enol tautomer and an active site residue of the kinase.

86. A method of inhibiting kinase comprising: causing a compound according to claim 1 to be present in a subject in order to inhibit kinase in vivo.

* * * * *